US012233135B2

(12) United States Patent
Ullman et al.

(10) Patent No.: US 12,233,135 B2
(45) Date of Patent: Feb. 25, 2025

(54) THERAPEUTIC CONSTRUCTS FOR TREATING CANCER

(71) Applicant: PRECISION MOLECULAR INC., Gaithersburg, MD (US)

(72) Inventors: Christopher Ullman, Hertfordshire (GB); Christine Anne Carrington, Cambridgeshire (GB)

(73) Assignee: PRECISION MOLECULAR INC., Gaithersburg, MD (US)

( * ) Notice: Subject to any disclaimer, the term of this patent is extended or adjusted under 35 U.S.C. 154(b) by 1070 days.

(21) Appl. No.: 17/047,011

(22) PCT Filed: Apr. 10, 2019

(86) PCT No.: PCT/US2019/026849

§ 371 (c)(1), (2) Date: Oct. 12, 2020

(87) PCT Pub. No.: WO2019/200013

PCT Pub. Date: Oct. 17, 2019

(65) Prior Publication Data

US 2021/0154328 A1 May 27, 2021

Related U.S. Application Data

(60) Provisional application No. 62/655,926, filed on Apr. 11, 2018.

(51) Int. Cl.

| | |
|---|---|
| ***A61K 48/00*** | (2006.01) |
| ***A61K 9/19*** | (2006.01) |
| ***A61K 38/17*** | (2006.01) |
| ***A61K 38/20*** | (2006.01) |
| ***A61K 38/45*** | (2006.01) |
| ***A61K 39/00*** | (2006.01) |
| ***A61K 39/395*** | (2006.01) |
| ***A61K 47/59*** | (2017.01) |
| ***A61P 35/00*** | (2006.01) |

(52) U.S. Cl.

CPC ............ *A61K 48/0058* (2013.01); *A61K 9/19* (2013.01); *A61K 38/1774* (2013.01); *A61K 38/208* (2013.01); *A61K 38/45* (2013.01); *A61K 39/3955* (2013.01); *A61K 39/4611* (2023.05); *A61K 39/4631* (2023.05); *A61K 39/464401* (2023.05); *A61K 39/464404* (2023.05); *A61K 39/464406* (2023.05); *A61K 47/59* (2017.08); *A61P 35/00* (2018.01); *A61K 2239/31* (2023.05); *A61K 2239/38* (2023.05); *A61K 2239/55* (2023.05)

(58) Field of Classification Search

CPC .............. A61K 48/0058; A61K 38/208; A61K 39/00119; A61P 35/00; C07K 16/32; C12N 2830/0008

USPC ..................... 435/6.1, 91.1, 91.31, 455, 458; 514/44 A, 44 R; 530/300, 350; 536/23.1, 536/24.5

See application file for complete search history.

(56) References Cited

U.S. PATENT DOCUMENTS

| | | | | |
|---|---|---|---|---|
| 4,405,712 | A | 9/1983 | Vande Woude | |
| 4,650,764 | A | 3/1987 | Temin | |
| 5,252,479 | A | 10/1993 | Srivastava | |
| 5,629,204 | A | 5/1997 | Honjo | |
| 5,698,520 | A | 12/1997 | Honjo | |
| 5,846,767 | A | 12/1998 | Halpin | |
| 5,994,104 | A | 11/1999 | Anderson | |
| 6,451,571 | B1 | 9/2002 | Loeb | |
| 6,737,523 | B1 | 5/2004 | Fisher | |
| 6,897,024 | B2 | 5/2005 | Bussemakers | |
| 7,247,297 | B2 | 7/2007 | Weichselbaum | |
| 7,321,030 | B2 | 1/2008 | Hamada | |
| 7,364,727 | B2 | 4/2008 | Li | |
| 7,507,792 | B2 | 3/2009 | Fisher | |
| 7,816,131 | B2 | 10/2010 | Hung | |
| 8,034,914 | B2 | 10/2011 | Hochberg | |
| 8,163,528 | B2 | 4/2012 | Black | |
| 2001/0011112 | A1 | 8/2001 | Langford | |
| 2004/0132101 | A1 | 7/2004 | Lazar | |
| 2008/0213220 | A1 | 9/2008 | Fisher | |
| 2008/0227958 | A1 | 9/2008 | Thompson | |
| 2009/0006520 | A1 | 1/2009 | Abib | |
| 2009/0311664 | A1 | 12/2009 | Fong | |
| 2011/0136221 | A1 | 6/2011 | Black | |
| 2013/0263296 | A1 | 10/2013 | Pomper | |
| 2014/0227182 | A1* | 8/2014 | Pomper | A61K 49/0054 424/1.73 |
| 2017/0042829 | A1 | 2/2017 | Mao | |

FOREIGN PATENT DOCUMENTS

| | | | |
|---|---|---|---|
| WO | 8905345 | 6/1989 | |
| WO | 9006997 | 6/1990 | |
| WO | 9205266 | 4/1992 | |
| WO | 9207573 | 5/1992 | |
| WO | 9214829 | 9/1992 | |
| WO | 2007041635 | 4/2007 | |
| WO | WO-2011097456 A2 * | 8/2011 | A61K 31/69 |
| WO | 2012127464 | 9/2012 | |
| WO | WO-2012127464 A2 * | 9/2012 | A61K 35/17 |
| WO | 2015080631 | 6/2015 | |

(Continued)

OTHER PUBLICATIONS

Yu et al (J. of Cancer, vol. 7, No. 7, pp. 872-882 (2016)) (Year: 2016).*

Kim et al (PLOS One, vol. 6, No. 4: e18556, pp. 1-12 (2011)) (Year: 2011).*

(Continued)

*Primary Examiner* — Jane J Zara

(74) *Attorney, Agent, or Firm* — PABST PATENT GROUP LLP

(57) ABSTRACT

The present disclosure provides nucleic acid constructs for the treatment of cancer, comprising a cancer-specific promoter and one or more therapeutic genes.

20 Claims, 17 Drawing Sheets

Specification includes a Sequence Listing.

(56) References Cited

FOREIGN PATENT DOCUMENTS

| | | | |
|---|---|---|---|
| WO | 2016170039 | 10/2016 | |
| WO | 2017049132 | 3/2017 | |
| WO | WO-2017049132 A1 * | 3/2017 | ............ A61K 31/19 |
| WO | 2018049261 | 3/2018 | |
| WO | WO-2018041838 A1 * | 3/2018 | .......... A61K 35/761 |

OTHER PUBLICATIONS

Ahn, et al., "Nanoparticle-mediated tumor cell expression of mll-12 via systemic gene delivery treats syngeneic models of murine lung cancers", Scientific Reports, 11(97331): 1-13 (2021).
Al-Madhoun, et al., "Evaluation of Human Thymidine Kinase 1 Substrates as New Candidates for Boron Neutron Capture Therapy", Cancer Res., 64(17):6280-6 (2004).
Amancha, et al., "In vivo blockade of the PD-1 pathway using soluble rPD-1-Fc enhances CD4+ and CD8+ T cell responses but has limited clinical benefit", J Immunol., 191(12):6060-70 (2013).
Anderson, et al., "Construction and biological characterization of an interleukin-12 fusion protein (Flexi-12): delivery to acute myeloid leukemic blasts using adeno-associated virus", Human Gene Therapy, 8(9):1125-1135 (1997).
Apostolovic, et al., "Coiled coils: attractive protein folding motifs for the fabrication of self-assembled, responsive and bioactive materials", Chem. Soc. Rev., 39(9):3541-75 (2010).
Bartlett, et al., "Oncolytic viruses as therapeutic cancer vaccines", Molecular Cancer, 12(103):1-16 (2013).
Berkner, "Development of adenovirus vectors for the expression of heterologous genes", Biotechniques, 6(7):616-626 (1988).
Blaese, et al., "T Lymphocyte-Directed Gene Therapy for ADA—SCID: Initial Trial Results After 4 Years", Science, 270(5235):475-480 (1995).
Bode, et al., "CpG DNA as a vaccine adjuvant", Expert Rev. Vaccines, 10(4):499-511 (2011).
Boudko, et al., "The NC2 Domain of Type IX Collagen Determines the Chain Register of the Triple Helix", J. Biol. Chem., 287:44536-45 (2012).
Car, et al., "The toxicology of interleukin-12: a review", Tox. Pathology, 27(1):58-63 (1999).
Cheever, et al., "The prioritization of cancer antigens: a national cancer institute pilot project for the acceleration of translational research", Clin. Cancer Res., 15(17):5323-3 (2009).
Chen, et al., "Minicircle DNA vectors devoid of bacterial DNA result in persistent and high-level transgene expression in vivo", Molecular Therapy, 8(3): 495-500 (2003).
Chen, et al., "SP1-induced IncRNA-ZFAS1 contributes to colorectal cancer progression via the miR-150-5p/VEGFA axis", Cell Death and Disease, 9(10):982, 18 pages (2018).
Cheng, et al., "Structure and interactions of the human programmed cell death 1 receptor", J. Biol. Chem., 288(17): 11771-11785 (2013).
Cho, et al., "Programmed death-1 receptor negatively regulates LPS-mediated IL-12 production and differentiation of murine macrophage RAW264.7 cells", Immunology Letters, 127(1):39-47 (2009).
Choi, et al., "AAV hybrid serotypes: improved vectors for gene delivery", Curr Gene Ther., 5(3):299-310 (2005).
Cotten, et al., "High-efficiency receptor-mediated delivery of small and large (48 kilobase gene constructs using the endosome-disruption activity of defective or chemically inactivated adenovirus particles", Proc. Natl. Acad. Sci. USA, 89(13):6094-6098 (1992).
Danos, et al., "Safe and efficient generation of recombinant retroviruses with amphotropic and ecotropic host ranges", Proc. Natl. Acad. Sci. USA, 85(17):6460-6464 (1988).
Das, et al., "Gene Therapies for Cancer: Strategies, Challenges and Successes", Journal of Cellular Physiology, 230(2): 259-271 (2014).
Dash, et al., "Apogossypol derivative BI-97C1 (Sabutoclax) targeting Mcl-1 sensitizes prostate cancer cells to mda-7/IL-24-mediated toxicity", Proc. Natl. Acad. Sci. USA, 108(21):8785-90 (2011b).
Dash, et al., "Developing an effective gene therapy for prostate cancer: New technologies with potential to translate from the laboratory into the clinic", Discov. Med., 11(56):46-56 (2011a).
Deng, et al., "Irradiation and anti-PD-L1 treatment synergistically promote antitumor immunity in mice", J Clin Invest., 124(2):687-695 (2012).
Donahue, et al., "Reduction in SIV replication in rhesus macaques infused with autologous lymphocytes engineered with antiviral genes", Nature Med., 4(2):181-186 (1998).
Doronin, et al., "Tissue-specific, tumor-selective, replication-competent adenovirus vector for cancer gene therapy", J. Virol., 75(7): 3314-3324 (2001).
Finlay, et al., "Natural and man-made V-gene repertoires for antibody discovery", Front Immunol., 3:342 (2012).
Fraser, et al., "Generation of a universal CD4 memory T cell recall peptide effective in humans, mice and non-human primates", Vaccine, 32(24): 2896-2903 (2014).
Fukazawa, et al., "Development of a Cancer-Targeted Tissue-Specific Promoter System", Cancer Research, American Association for Cancer Research, 64(1): 363-369 (2004).
Geller, et al., "A defective HSV-1 vector expresses *Escherichia coli* beta-galactosidase in cultured peripheral neurons", Science, 241(4873):1667-1669 (1988).
Gill, et al., "Chimeric antigen receptor T cell therapy: 25years in the making", Blood Reviews, 30(3):157-167 (2016).
Goldman, et al., "Lentiviral vectors for gene therapy of cystic fibrosis", Human Gene Therapy, 8(18):2261-2268 (1997).
Graham, et al., "Manipulation of adenovirus vectors", Meth. Mol. Biol., 7:109-127 (1991).
Greelish, et al., "Stable restoration of the sarcoglycan complex in dystrophic muscle perfused with histamine and a recombinant adeno-associated viral vector", Nature Med., 5(4):439-443 (1999).
Green, et al., "Combinatorial Modification of Degradable Polymers Enables Transfection of Human Cells Comparable to Adenovirus", Adv. Mater., 19:2836-2842 (2007).
Hallenbeck, et al., "A novel tumor-specific replication-restricted adenoviral vector for gene therapy of hepatocellular carcinoma", Hum. Gene Ther., 10(10):1721-1733 (1999).
Herzog, et al., "Long-term correction of canine hemophilia B by gene transfer of blood coagulation factor IX mediated by adeno-associated viral vector", Nature Med., 5(1):56-63 (1999).
Hey, et al., "Artificial, non-antibody binding proteins for pharmaceutical and industrial applications", Trends in Biotechnology, 23(10): 514-522 (2005).
Hombach, et al., "Targeting two co-operating cytokines efficiently shapes immune responses", Abken Oncoimmunology, 2(3):e23205 (2013).
Huang, et al., "CpG-based irn1 nunotherapy impairs antitun1or activity of BRAF inhibitors in a B-cell-dependent manner", Oncogene, 36(28): 4081-4096 (2017).
Huang, et al., "DAMPs, ageing, and cancer: the 'DAMP hypothesis'" Ageing Res Rev., S1568-1637(14) 00113-5 (2014).
Huang, et al., "Receptor-Fc fusion therapeutics, traps, and Mimetibody technology", Current Opinion in Biotechnology, 20(6):692-699 (2009).
International Search Report for PCT/US2019/026849 dated Jul. 11, 2019.
Kafri, et al., "Sustained expression of genes delivered directly into liver and muscle by lentiviral vectors", Nature Genetics, 17(3):314-317 (1997).
Kim, et al., "High Cleavage Efficiency of a 2A Peptide Derived from Porcine Teschovirus-1 in Human Cell Lines, Zebrafish and Mice", PLoS One, 6(4): 1-8 (2011).
Kurihara, et al., "Selectivity of a replication-competent adenovirus for human breast carcinoma cells expressing the MUC1 antigen", J. Clin. Investig., 106(6): 763-771 (2000).
Lairmore, et al., "Human T-lymphotropic virus type 1 peptides in chimeric and multivalent constructs with promiscuous T-cell epitopes enhance immunogenicity and overcome genetic restriction", J. Virol., 69(10): 6077-6089 (1995).
Lee, et al., "Selective activation of ceruloplasmin promoter in ovarian tumors: potential use for gene therapy", Cancer Res., 64(5):1788 (2004).

(56) References Cited

OTHER PUBLICATIONS

Li, et al., "Assessment of recombinant adenoviral vectors for hepatic gene therapy", Human Gene Therapy, 4(4):403-409 (1993).
Li, et al., "Ménage à Trois in stress: DAMPs, redox and autophagy", Seminars in Cancer Biology, 23(5): 380-390 (2013).
Lozano, et al., "Blockage of FOXP3 transcription factor dimerization and FOXP3/AML1 interaction inhibits T regulatory cell activity: sequence optimization of a peptide inhibitor", Oncotarget, 8(42):71709-71724 (2017).
Mahmood, et al., "Death receptors: targets for cancer therapy", Experimental Cell Research, 316(6): 887-899 (2010).
Mahoney, et al., "Combination cancer immunotherapy and new immunomodulatory targets", Nature Reviews Drug Discovery, 14(8):561-565 (2015).
Medrola, et al., "The single transmembrane domains of ErbB receptors self-associate in cell membranes" J. Biol. Chem, 277(7): 4704-4712 (2002).
Onodera, et al., "Development of improved adenosine deaminase retroviral vectors", J. Virol., 72(3): 1769-1774 (1998).
Ott, et al., "Combination immunotherapy: a road map", Journal for Immuno Therapy of Cancer, 5(16):1-15 (2017).
Pasche, et al., "Immunocytokines: a novel class of potent armed antibodies", Drug Discovery Today, 17(11-12):583-590 (2012).
Pflaum, et al., "p53 Family and Cellular Stress Responses in Cancer", Front Oncol., 4(285):1-15 (2014).
Piccini, et al., "Vaccinia virus as an expression vector", Meth. Enzymology, 153:545-563 (1987).
Robertson, et al., "A selection system for functional internal ribosome entry site (IRES) elements: analysis of the requirement for a conserved GNRA tetraloop in the encephalomyocarditis virus IRES", RNA, 5(9):1167-1179 (1999).
Rodrigo-Garzon, et al., "Antitumoral efficacy of DNA nanoparticles in murine models of lung cancer and pulmonary metastasis", Cancer Gene Therapy, 17: 20-27 (2010).
Rodriguez Gascon, et al., "Non-Viral Delivery Systems in Gene Therapy", Gene Therapy—Tools and Potential Applications, 1:3-33 (2013).
Rodriguez, et al., "Prostate attenuated replication competent adenovirus (ARCA) CN706: a selective cytotoxic for prostate-specific antigen-positive prostate cancer cells", Cancer Res., 57: 2559-2563 (1997).
Sampson, et al., "EGFRvIII mCAR-Modified T-ell Therapy Cures Mice with Established Intracerebral Glioma and Generates Host Immunity against Tumor-Antigen Loss", Clin. Cancer Res., 20(4):972-984 (2013).
Shackleford, et al., "Construction of a clonable, infectious, and tumorigenic mouse mammary tumor virus provirus and a derivative genetic vector", Proc. Natl. Acad. Sci. USA, 85:9655-9659 (1988).
Sharma, et al., "2A peptides provide distinct solutions to driving stop-carry on translational recoding", Nucleic Acids Res., 40(7): 3143-3151 (2012).
Snyder, et al., "Correction of hemophilia B in canine and murine models using recombinant adeno-associated viral vectors", Nature Med., 5(1):64-70 (1999).
Spencer, et al., "Fusion of the Mycobacterium tuberculosis antigen 85A to an oligomerization domain enhances its immunogenicity in both mice and non-human primates", PLoS One, 7(3):e33555, 15 pages (2012).
Spiess, et al., "Alternative molecular formats and therapeutic applications for bispecific antibodies", Molecular Immunology, 67(2 Pt A): 95-106 (2015).
Stec, et al., "Cyclic trans-phosphorylation in a homodimer as the predominant mechanism of EGFRvIII action and regulation", Oncotarget, 9(9): 8560-8572 (2018).
Su, et al., "Non-viral tumor gene therapay with novel plasmids expressing the cytotoxic cytokine TNF-a", Human Gene Therapy, 20:1417-1545 (2009).
Su, et al., "Targeting gene expression selectively in cancer cells by using the progression-elevated gene-3 promoter", Proceedings of The National Academy of Sciences, 102(4):1059-1064 (2005).
Tang, et al., "PAMPs and DAMPs: signal 0s that spur autophagy and immunity", Immunol. Rev., 249(1):158-175 (2012).
Tseng, et al., "Highly specific in vivo gene delivery for p53-mediated apoptosis and genetic photodynamic therapies of tumour", Nat Commun., 6:6456 (2015).
Valmori, et al., "Use of human universally antigenic tetanus toxin T cell epitoes as carriers for human vaccination", The Journal of Immunology, 149:717-721 (1992).
Venkatesan, et al., "The potential of celecoxib-loaded hydroxyapatite-chitosan nanocomposite for the treatment of colon cancer", Biomaterials, 32(15):3794-806 (2011).
Wang, et al., "Sustained correction of bleeding disorder in hemophilia B mice by gene therapy", Proc. Nat. Acad. Sci. USA, 96:3906-3910 (1999).
Wang, et al., "The prognostic value of PD-L1 expression for non-small cell lung cancer patients: a meta-analysis", EJSO, 41(4): 450-456 (2015).
Weidle, et al., "The emerging role of new protein scaffold-based agents for treatment of cancer", Cancer Genomics and Proteomics, 10(4):155-168 (2013).
Wu, et al., "PD-L1 and Survival in Solid Tumors: A Meta-Analysis", PLoS One, 10(6): e0131403 (2015).
Yu, et al., "Role of Four Different Kinds of Polyethylenimines (PEIs) in Preparation of Polymeric Lipid Nanoparticles and Their Anticancer Activity Study", Journal of Cancer, 7(7):872-82 (2016).
Yue, et al., "Interleukin 12 shows a better curative effect on lung cancer than paclitaxel and cisplatin doublet chemotherapy", BMC Cancer, 16(1):665, 1-13 (2016).
Zabner, et al., "Safety and efficacy of repetitive adenovirus-mediated transfer of CFTR cDNA to airway epithelia of primates and cotton rats", Nature Genetics, 6(1):75-83 (1994).
Blaese, et al., "T Lymphocyte-Directed Gene Therapy for ADA—SCIS: Initial Trial Results After 4 Years", *Science*, 270(5235):475-480 (1995).
Gill, et al., "Chimeric antigen receptor T cell therapy: 25 years in the making", *Blood Reviews*, 30:157-167 (2016).
Huang, et al., "CpG-based irn1nunotherapy impairs antitunlor activity of BRAF inhibitors in a B-cell-dependent manner", *Oncogene*, 36(28): 4081-4096 (2017).

* cited by examiner

Donor 301
Luminescence
1200000
1000000
800000
600000
400000
Theoretical bound IL-12 (ng/ml)
PEG-TK-hIL2-mIL12
PEG-TK-mIL12
PEG-mIL12
PEG-TK-mIL2-mIL12
PEG-mIL2-mIL12
PEG-lucia
Donor 303
Luminescence
1400000
1200000
1000000
Theoretical bound IL-12 (ng/ml)
PEG-TK-hIL2-mIL12
PEG-TK-mIL12
PEG-mIL12
PEG-TK-mIL2-mIL12
PEG-mIL2-mIL12
PEG-lucia

SEQUENCE LISTING

```
<160> NUMBER OF SEQ ID NOS: 33

<210> SEQ ID NO 1
<211> LENGTH: 1148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

ccatggcttc ttaccctgga caccagcatg cttctgcctt tgaccaggct gccagatcca     60

ggggccactc caacaggaga actgccctaa gacccagaag acagcaggaa gccactgagg    120

tgaggcctga gcagaagatg ccaaccctgc tgagggtgta cattgatgga cctcatggca    180

tgggcaagac caccaccact caactgctgg tggcactggg ctccagggat gacattgtgt    240

atgtgcctga gccaatgacc tactggagag tgctaggagc ctctgagacc attgccaaca    300

tctacaccac ccagcacagg ctggaccagg gagaaatctc tgctggagat gctgctgtgg    360

tgatgacctc tgcccagatc acaatgggaa tgccctatgc tgtgactgat gctgttctgg    420

ctcctcacat tggaggagag gctggctctt ctcatgcccc tccacctgcc ctgaccctga    480

tctttgacag acaccccatt gcagccctgc tgtgctaccc agcagcaagg tacctcatgg    540

gctccatgac cccacaggct gtgctggctt ttgtggccct gatccctcca accctccctg    600

gcaccaacat tgttctggga gcactgcctg aagacagaca cattgacagg ctggcaaaga    660

ggcagagacc tggagagaga ctggacctgg ccatgctggc tgcaatcaga agggtgtatg    720

gactgctggc aaacactgtg agatacctcc agtgtggagg ctcttggaga gaggactggg    780

gacagctctc tggaacagca gtgccccctc aaggagctga gccccagtcc aatgctggtc    840

caagacccca cattggggac accctgttca ccctgttcag agcccctgag ctgctggctc    900

ccaatggaga cctgtacaat gtgtttgcct gggctctgga tgttctagcc aagaggctga    960

ggtccatgca tgtgttcatc ctggactatg accagtcccc tgctggatgc agagatgctc   1020

tgctgcaact aacctctggc atggtgcaga cccatgtgac caccccctggc agcatcccca   1080
```

ccatctgtga cctagccaga acctttgcca gggagatggg agaggccaat ggatcctgat 1140
aagctagc 1148

<210> SEQ ID NO 2
<211> LENGTH: 1148
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
ccatggcttc ttaccctgga caccagcatg cttctgcctt tgaccaggct gccagatcca 60
ggggccactc caacaggaga actgccctaa gacccagaag acagcaggaa gccactgagg 120
tgaggcctga gcagaagatg ccaaccctgc tgagggtgta cattgatgga cctcatggca 180
tgggcaagac caccaccact caactgctgg tggcactggg ctccagggat gacattgtgt 240
atgtgcctga gccaatgacc tactggagag tgctaggagc ctctgagacc attgccaaca 300
tctacaccac ccagcacagg ctggaccagg gagaaatctc tgctggagat gctgctgtgg 360
tgatgacctc tgcccagatc acaatgggaa tgccctatgc tgtgactgat gctgttctgg 420
ctcctcacat tggaggagag gctggctctt ctcatgcccc tccacctgcc ctgaccattt 480
tcctggacag acatcccatt gccttcatgc tgtgctaccc agcagcaagg tacctcatgg 540
gctccatgac cccacaggct gtgctggctt ttgtggccct gatccctcca accctccctg 600
gcaccaacat tgttctggga gcactgcctg aagacagaca cattgacagg ctggcaaaga 660
ggcagagacc tggagagaga ctggacctgg ccatgctggc tgcaatcaga agggtgtatg 720
gactgctggc aaacactgtg agatacctcc agtgtggagg ctcttggaga gaggactggg 780
gacagctctc tggaacagca gtgccccctc aaggagctga gccccagtcc aatgctggtc 840
caagacccca cattggggac accctgttca ccctgttcag agcccctgag ctgctggctc 900
ccaatggaga cctgtacaat gtgtttgcct gggctctgga tgttctagcc aagaggctga 960
ggtccatgca tgtgttcatc ctggactatg accagtcccc tgctggatgc agagatgctc 1020
tgctgcaact aacctctggc atggtgcaga cccatgtgac cacccctggc agcatcccca 1080
ccatctgtga cctagccaga acctttgcca gggagatggg agaggccaat ggatcctgat 1140
aagctagc 1148

<210> SEQ ID NO 3
<211> LENGTH: 509
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
aagcttggca ttccggtact gttggtaaag ccaccatgta caggatgcaa ctcctgtctt 60
gcattgcact gagtcttgca cttgtcacaa acagtgcacc tacttcaagt tctacaaaga 120
aaacacagct gcaactggag catctcctgc tggatctgca gatgatcttg aatggaatta 180
ataattacaa gaatcccaaa ctcaccagga tgctcacatt taagttttac atgcccaaga 240
aggccacaga actgaaacat cttcagtgtc tggaagaaga actcaaacct ctggaggaag 300
tgctcaatct ggctcaaagc aaaaactttc acctgagacc cagggacctg atcagcaata 360

```
tcaatgtaat tgttctggaa ctcaagggat ctgaaacaac attcatgtgt gaatatgctg    420

atgagacagc aaccattgtg gaatttctga acagatggat taccttttgt caaagcatca    480

tctcaacact gacttaaacc tgagctagc                                      509
```

<210> SEQ ID NO 4
<211> LENGTH: 557
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
aagcttggca ttccggtact gttggtaaag ccaccatgta cagcatgcag ctggcctcct     60

gtgtgacact gacactggtg ctgctggtga actctgcacc cacttcaagc tccacctcaa    120

gctctacagc tgaagcccag cagcagcagc agcagcagca gcagcagcag cagcacctgg    180

agcagctgct gatggacctg caggagctgc tgagcaggat ggagaattac aggaacctga    240

aactccccag gatgctgacc ttcaaatttt acttgcccaa gcaggccaca gaactgaagg    300

atctgcagtg cctggaagat gaacttggac ctctgaggca tgtgctggat ctgactcaaa    360

gcaagagctt tcaactggaa gatgctgaga atttcatcag caatatcaga gtgactgtgg    420

tcaaactgaa gggctctgac aacacatttg agtgccaatt tgatgatgag tcagccactg    480

tggtggactt tctgaggaga tggattgcct tctgtcaaag catcatctca acaagccctc    540

aataaacctg agctagc                                                   557
```

<210> SEQ ID NO 5
<211> LENGTH: 1698
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
gcggccgctc gagatctgcg atctaagtaa gcttggcatt ccggtactgt tggtaaagcc     60

accatgtgtc accagcagtt ggtcatctct tggttttccc tggtttttct ggcatctccc    120

ctggtggcca tctgggaact gaagaaagat gtttatgtgg tggaattgga ttggtatcct    180

gatgcccctg gagaaatggt ggtcctcacc tgtgacaccc ctgaagaaga tggtatcacc    240

tggaccttgg accagagcag tgaggtcctg ggctctggca aaaccctgac catccaagtc    300

aaagagtttg gagatgctgg ccagtacacc tgtcacaaag gaggggaggt tctgagccat    360

tccctcctgc tgcttcacaa aaaggaagat ggaatttggt ccactgatat tctgaaggac    420

cagaaagaac ccaaaaataa gacctttctg agatgtgagg ccaagaatta ttctggaaga    480

ttcacctgct ggtggctgac cacaatcagt actgatttga cattcagtgt caaaagcagc    540

agaggctctt ctgaccccca aggggtgacc tgtggagctg ctacactctc tgcagagaga    600

gtcagagggg acaacaagga gtatgagtac tcagtggagt gccaggagga cagtgcctgc    660

ccagctgctg aggagagtct gcccattgag gtcatggtgg atgctgttca caagctcaag    720

tatgaaaact acaccagcag cttcttcatc agggacatca tcaaacctga cccacccaag    780

aacttgcagc tgaagccact gaagaattct aggcaggtgg aggtcagctg ggagtaccct    840

gacacctgga gtactccaca ttcctacttc tccctgacat tctgtgttca ggtccagggc    900

aagagcaaga gagaaaagaa agatagagtc ttcacagaca agacctcagc cacagtcatc    960
```

```
tgcaggaaaa atgccagcat tagtgtgagg gcccaggaca gatactatag ctcatcttgg   1020
agtgaatggg catctgtgcc ctgcagtggt ggaggtggaa gtggaggtgg tggatctggg   1080
ggtggaggca gcagaaacct ccctgtggcc actccagacc caggaatgtt cccatgcctt   1140
caccactccc aaaacctgct gagggctgtc agcaacatgc tccagaaggc cagacaaact   1200
ctggaatttt acccttgcac ttctgaagag attgatcatg aagatatcac aaaagataaa   1260
accagcacag tggaggcctg tctgccattg gaactcacca agaatgagag ttgcctgaat   1320
tccagagaga cctctttcat cactaatggg agttgcctgg cctccagaaa gacctctttt   1380
atgatggccc tgtgccttag tagtatttat gaagacttga agatgtacca ggtggagttc   1440
aagaccatga atgcaaagct tctgatggac cctaagaggc agatctttct ggatcaaaac   1500
atgctggcag ttattgatga gctgatgcag gccctgaatt tcaacagtga gactgtgcca   1560
caaaaatcct cccttgaaga acctgatttt tataaaacta aaatcaagct ctgcatcctt   1620
cttcatgctt tcagaattag ggcagtgact attgacagag tgatgagcta tctgaatgct   1680
tcctaaacct gagctagc                                                 1698
```

```
<210> SEQ ID NO 6
<211> LENGTH: 1679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

aagcttggca ttccggtact gttggtaaag ccaccatgtg tcctcagaag ctcaccatct     60
cctggtttgc cattgttttg ctggtgtctc cactcatggc catgtgggag ctggagaaag    120
atgtttatgt tgtggaggtg gactggactc ctgatgcccc tggagaaaca gtgaacctca    180
cctgtgacac ccctgaagaa gatgacatca cctggacctc agaccagaga catggagtca    240
taggctctgg aaagaccctg accatcactg tcaaagagtt tctggatgct ggccagtaca    300
cctgccacaa aggaggggag actctgagcc actcacatct gctgctccac aagaaggaaa    360
atggaatttg gtccactgaa attctgaaaa atttcaaaaa caagactttc ctgaagtgtg    420
aagcaccaaa ttactctgga aggttcacct gctcatggct ggtgcaaaga aacatggact    480
tgaagttcaa catcaagagc agtagcagtt cccctgactc tagggcagtg acatgtggaa    540
tggcctctct gtctgcagag aaggtcacac tggaccaaag ggactatgag aagtattcag    600
tgtcctgcca ggaggatgtc acctgcccaa ctgctgagga gaccctgccc attgaactgg    660
ccttggaagc aaggcagcag aataaatatg agaactacag caccagcttc ttcatcaggg    720
acatcatcaa accagaccct cccaagaact tgcagatgaa gcctttgaag aactcacagg    780
tggaggtcag ctgggagtac cctgactcct ggagcactcc ccattcctac ttctccctca    840
agttctttgt tagaatccag aggaagaaag aaaagatgaa ggagacagag gaggggtgta    900
accagaaagg tgccttcctg gtggagaaga catctacaga agtccaatgc aaaggaggga    960
atgtctgtgt gcaagctcag gataggtatt acaattcctc atgcagcaag tgggcatgtg   1020
ttccctgcag ggtcagatct ggtggaggtg gaagtggagg tggtggatct gggggtggag   1080
gcagcagggt cattccagtc tctggacctg ccaggtgtct tagccagtcc agaaacctgc   1140
tgaagaccac agatgacatg gtgaagactg ccagagaaaa actgaaacat tattcctgca   1200
ctgctgaaga cattgatcat gaagacatca caagggacca aaccagcaca ttgaagacct   1260
```

```
gtctgccact ggaactgcac aagaatgaga gttgcctggc tactagagag acttcttcca   1320

caacaagagg gagctgcctg cccccacaga agacctcttt gatgatgacc ctgtgccttg   1380

gtagcatcta tgaggacttg aagatgtacc agacagagtt ccaggccatc aatgcagcac   1440

ttcagaatca caaccatcag cagatcattc tggacaaggg catgctggtg gccattgatg   1500

agctgatgca gtctctgaat cataatggag agactctgag acagaaacct cctgtgggag   1560

aagcagaccc ttacagagtg aaaatgaagc tctgcatcct gcttcatgcc ttcagcacca   1620

gagtggtgac catcaacagg gtgatgggct atctgagctc tgcctaaacc tgagctagc    1679
```

<210> SEQ ID NO 7
<211> LENGTH: 438
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
cgtctcagac ctatgtacag gatgcaactc ctgtcttgca ttgcactgag tcttgcactt     60

gtcacaaaca gtgcaggagc caactgggtg aatgtgatca gtgatttgaa aaaaattgaa    120

gatcttattc aatctatgca tattgatgct actttgtata cagaaagtga tgttcacccc    180

agttgcaaag tgacagcaat gaagtgcttt ctcttggagc tgcaagttat ttcacttgag    240

tctggagatg caagtattca tgatacagtg gaaaatctga tcatcctggc aaacaacagt    300

ttgtcttcta atgggaatgt gacagaatct ggatgcaaag aatgtgagga actggaggaa    360

aaaaatatta aagaattttt gcagagtttt gtgcatattg tccaaatgtt catcaacact    420

tcttaaacct gagctagc                                                  438
```

<210> SEQ ID NO 8
<211> LENGTH: 668
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
aagcttggca ttccggtact gttggtaaag ccaccatgaa ttttcaacag aggctgcaaa     60

gcctgtggac tctggccaga cccttctgcc ctcctttgct ggccacagcc tctcaaatgc    120

agatggttgt gctcccttgc ctgggtttta ccctgcttct ctggagccag gtgtcagggg    180

cccagggcca agaattccac tttgggccct gccaagtgaa gggggttgtt ccccagaaac    240

tgtgggaagc cttctgggct gtgaaagaca ctatgcaagc tcaggataac atcaccagtg    300

ccaggctgct gcagcaggag gttctgcaga atgtctctga tgctgagagc tgttaccttg    360

tccacaccct gctggagttc tacttgaaaa ctgttttcaa aaactaccac aatagaacag    420

ttgaagtcag gactctgaag tcattctcta ctctggccaa caactttgtt ctcattgtgt    480

cacaactgca acccagtcaa gaaaatgaga tgttttccat cagagacagt gcacacagga    540

ggtttctgct gttcagaaga gcattcaaac agttggatgt ggaagcagct ctgaccaaag    600

cccttgggga agtggacatt cttctgacct ggatgcagaa attctacaag ctctaaacct    660

gagctagc                                                             668
```

<210> SEQ ID NO 9

```
<211> LENGTH: 499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

ggatcctctg gaagtggagc tactaacttc agcctgctga agcaggctgg agatgtggct     60

gcagagcctg ctgctcttgg gcactgtggc ctgcagcatc tctgcacctg ccagaagccc    120

cagccccagc acccagccct gggagcatgt gaatgccatc caggaggcca ggaggctcct    180

gaacctgagt agagacactg ctgctgagat gaatgaaaca gtggaagtca tctcagaaat    240

gtttgacctc caggagccca cctgcctcca gaccaggctg gagctgtaca agcagggcct    300

gaggggcagc ctcaccaagc tcaagggccc cttgaccatg atggccagcc actacaagca    360

gcactgccct ccaacccctg aaacttcctg tgcaacccag attatcacct ttgaaagttt    420

caaagagaac ctgaaggact ttctgcttgt catccccttt gactgctggg agccagtcca    480

ggagtgaacc tgagctagc                                                 499


<210> SEQ ID NO 10
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

ggatcctctg gaagtggagc tactaacttc agcctgctga agcaggctgg agatgtggag     60

gagaaccctg gacctatgtg gctgcagaat ctgcttttcc tgggcattgt ggtctacagc    120

ctctcagcac ccaccaggtc acccatcact gtcaccagac cttggaagca tgtagaggcc    180

atcaaagaag ccctgaacct cctggatgac atgcctgtca ccttgaatga agaggtagaa    240

gtggtctcta atgagttctc cttcaagaag ctgacatgtg tgcagaccag actgaagata    300

tttgagcagg gtctaagggg caatttcacc aaactcaagg gagccttgaa catgacagcc    360

agctactacc agacatactg ccccccaact cctgaaacag actgtgaaac acaagttacc    420

acctatgctg atttcataga cagccttaaa acctttctga ctgatatccc ctttgaatgc    480

aaaaaaccag gccaaaaatg aacctgagct agc                                 513


<210> SEQ ID NO 11
<211> LENGTH: 1339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

ggatcctctg gaagtggagc tactaacttc agcctgctga agcaggctgg agatgtggag     60

gagaaccctg gacctatgga ctggacctgg agggtcttct gtttgctggc tgtaactcca    120

ggtgcccacc ccctggactc cccagacagg ccctggaacc cccccacctt ctccccagcc    180

ctgctggtgg tgactgaagg ggacaatgcc accttcacct gcagcttctc caacacatct    240

gagagctttg tgctgaactg gtacaggatg agccccagca accagactga caagctggct    300

gccttccctg aggacaggag ccagcctggc caggactgca gattcagggt cacacaactg    360
```

```
cccaatggga gggacttcca catgagtgtg gtcagggcca ggagaaatga cagtggcacc    420
tacctctgtg gggccatctc cctggccccc aaggcccaga tcaaagagag cctgagggca    480
gagctcaggg tgacagagag aagggcagaa gtgcccacag cccaccccag cccctcaccc    540
aggtcagctg gccagttcca aaccctggtg gagtccaaat atggtccccc atgcccacca    600
tgcccagcac ctgagtttga ggggggacca tcagtcttcc tgttcccccc aaaacccaag    660
gacactctca tgatctccag gacccctgag gtcacctgtg tggtggtgga tgtgagccag    720
gaagaccctg aggtccagtt caactggtat gtggatgggg tggaggtgca taatgccaag    780
acaaagccta gggaggagca gttcaacagc acctacagag tggtcagtgt cctcacagtc    840
ctgcaccagg actggctgaa tggcaaggag tacaagtgca aggtctccaa caaaggcctc    900
ccctcctcca ttgagaaaac catctccaaa gccaaagggc agcccagaga gccacaggtg    960
tacaccctgc ccccatccca ggaggagatg accaagaacc aggtcagcct gacctgcctg   1020
gtcaaaggct tctaccccag tgacattgct gtggagtggg agagcaatgg gcagcctgag   1080
aacaactaca agaccacacc tccagtgctg gactctgatg gctccttctt cctctacagc   1140
aggctcacag tggacaagag caggtggcag gaggggaatg tcttctcatg ctctgtgatg   1200
catgaggctc tgcacaacca ctacacacag aagagcctct ccctgtctct gggtaaaaga   1260
aggaagaggg gaagtggaga gggcagagga agtctgctaa catgtggtga tgtggaggag   1320
aatcctggga cctgagacg                                                1339
```

<210> SEQ ID NO 12
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
cgtctcagac ctatggagac agacacactc ctgctgtggg tgctgctgct ctgggttcca     60
ggttccactg gtgacatggc acaagtcatt aatacaaaca gcctgtctct gttgacccag    120
aataacctga acaaatccca gtcagctctg ggcacagcta ttgagagact gtcttctggt    180
ctgaggatca acagtgccaa agatgatgct gcaggtcagg ccattgctaa caggtttact    240
gccaacatca aaggtctgac tcaggcttcc agaaatgcta atgatggtat ctccattgcc    300
cagaccactg aaggagctct gaatgaaatc aacaacaacc tgcagagagt gagggaactg    360
gctgttcagt ctgctaacag caccaactcc cagtctgacc tggactccat ccaggctgaa    420
atcacccaga gactgaatga aattgacaga gtgtctggcc agactcagtt caatggagtg    480
aaagtcctgg cccaggacaa caccctgacc atccaggttg gtgccaatga tggtgaaact    540
attgatattg atctgaagca gatcaactct cagaccctgg gtctggatac cctgaatgtg    600
caacaaaaat ataaggtcag tgatacagct gcaactgtta caggatatac tcaaaataaa    660
gatggttcca tcagtattaa tactacaaaa tacactgcag atgatggtac atccaaaact    720
gcactgaaca aactgggtgg ggcagatggc aaaacagaag ttgtttctat tggtggtaaa    780
acttatgctg caagtaaagc tgaaggtcac aactttaaag cacagcctga tctggctgaa    840
gctgctgcta caaccacaga aaaccctctg cagaaaattg atgctgcttt ggcacaggtt    900
gacaccctga gatctgacct gggtgctgtg cagaacaggt tcaactctgc tattaccaac    960
ctgggcaaca cagtgaacaa cctgacttct gccagaagca ggattgaaga ttctgactat   1020
```

```
gccacagaag tttccaacat gtctagagcc cagattctgc agcaggctgg tacctctgtt   1080

ctggcccagg ccaaccaggt tccccaaaat gtcctctctc tgctgagata aacctgagct   1140

agc                                                                 1143


<210> SEQ ID NO 13
<211> LENGTH: 3972
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

gcggccgctc gagatctgcg atctaagtaa gcttggcatt ccggtactgt tggtaaagcc     60

accatgtgtc accagcagtt ggtcatctct tggttttccc tggtttttct ggcatctccc    120

ctggtggcca tctgggaact gaagaaagat gtttatgtgg tggaattgga ttggtatcct    180

gatgcccctg gagaaatggt ggtcctcacc tgtgacaccc ctgaagaaga tggtatcacc    240

tggaccttgg accagagcag tgaggtcctg ggctctggca aaaccctgac catccaagtc    300

aaagagtttg gagatgctgg ccagtacacc tgtcacaaag gaggggaggt tctgagccat    360

tccctcctgc tgcttcacaa aaaggaagat ggaatttggt ccactgatat tctgaaggac    420

cagaaagaac ccaaaaataa gacctttctg agatgtgagg ccaagaatta ttctggaaga    480

ttcacctgct ggtggctgac cacaatcagt actgatttga cattcagtgt caaaagcagc    540

agaggctctt ctgaccccca aggggtgacc tgtggagctg ctacactctc tgcagagaga    600

gtcagagggg acaacaagga gtatgagtac tcagtggagt gccaggagga cagtgcctgc    660

ccagctgctg aggagagtct gcccattgag gtcatggtgg atgctgttca caagctcaag    720

tatgaaaact acaccagcag cttcttcatc agggacatca tcaaacctga cccacccaag    780

aacttgcagc tgaagccact gaagaattct aggcaggtgg aggtcagctg ggagtaccct    840

gacacctgga gtactccaca ttcctacttc tccctgacat tctgtgttca ggtccagggc    900

aagagcaaga gagaaaagaa agatagagtc ttcacagaca agacctcagc cacagtcatc    960

tgcaggaaaa atgccagcat tagtgtgagg gcccaggaca gatactatag ctcatcttgg   1020

agtgaatggg catctgtgcc ctgcagtggt ggaggtggaa gtggaggtgg tggatctggg   1080

ggtggaggca gcagaaacct ccctgtggcc actccagacc caggaatgtt cccatgcctt   1140

caccactccc aaaacctgct gagggctgtc agcaacatgc tccagaaggc cagacaaact   1200

ctggaatttt acccttgcac ttctgaagag attgatcatg aagatatcac aaaagataaa   1260

accagcacag tggaggcctg tctgccattg gaactcacca agaatgagag ttgcctgaat   1320

tccagagaga cctctttcat cactaatggg agttgcctgg cctccagaaa gacctctttt   1380

atgatggccc tgtgccttag tagtatttat gaagacttga agatgtacca ggtggagttc   1440

aagaccatga atgcaaagct tctgatggac cctaagaggc agatctttct ggatcaaaac   1500

atgctggcag ttattgatga gctgatgcag gccctgaatt tcaacagtga gactgtgcca   1560

caaaaatcct cccttgaaga acctgatttt tataaaacta aaatcaagct ctgcatcctt   1620

cttcatgctt tcagaattag ggcagtgact attgacagag tgatgagcta tctgaatgct   1680

tccaggagaa agagaggatc ctctggaagt ggagctacta acttcagcct gctgaagcag   1740

gctggagatg tggaggagaa ccctggacct atggagtttg ggctgagctg ggttttcctt   1800

gttgctcttt taagaggtgt ccagtgtcag gtgcagttgg tggagtctgg ggggggtgtg   1860
```

```
gtgcagccag ggaggtcact gagactgagt tgtgcagcaa gtgggtttac atttagtagt   1920
tatacaatgc attgggttag gcaagctcca gggaagggtc tggagtgggt gacttttatt   1980
tcttatgatg gtaataataa atattatgca gattcagtta agggaaggtt tactattagt   2040
agggataatt caaaaaatac tctgtatttg cagatgaatt ctctgagggc tgaggataca   2100
gctatttatt attgtgctag aactggttgg ctgggtccat ttgattattg ggggcaggga   2160
acacttgtga cagtgtcatc agcttcaaca aaaggtccat ctgtttttcc attggctcct   2220
tcttctaagt caacttctgg tggaactgca gctctgggat gtctggtgaa ggattatttt   2280
ccagaacctg tgactgtttc ttggaatagt ggtgctctga ctagtggagt tcatactttt   2340
ccagctgttc tgcagagttc tggactgtat tctctgagta gtgtggttac agttccatca   2400
agttctctgg gtactcaaac ttatatttgt aatgtgaatc ataagccttc aaatacaaag   2460
gtggataaaa gggtggagcc aaagtcatgt gataagactc atacatgtcc tccatgtcct   2520
gctccagagc ttctgggggg gccatctgtt tttctgtttc caccaaagcc taaggatact   2580
cttatgatta gtaggacacc agaagttaca tgtgtggtgg ttgatgtgtc tcatgaagat   2640
ccagaggtga agtttaattg gtatgttgat ggggtggagg ttcataatgc aaagacaaag   2700
cctagggagg aacagtataa tagtacatat agagtggtgt ctgtgctgac tgtgctgcat   2760
caggattggc tgaatggaaa agagtataag tgtaaagtgt caaataaggc tctgcctgca   2820
cctattgaaa aaacaatttc aaaggcaaaa gggcagccaa gggagcctca agtttatact   2880
ctgccacctt caagggatga acttacaaag aatcaagtga gtttgacttg tcttgtgaaa   2940
ggattttatc cttcagatat tgctgtggag tgggagtcaa atggtcagcc tgaaaataat   3000
tataagacta ctccaccagt gctggatagt gatgggtctt tttttctgta tagtaagctg   3060
actgtggata agtctaggtg gcagcaggga aatgtgtttt cttgtagtgt gatgcatgag   3120
gctctgcata atcattatac acagaagtct ctgagtttgt ctcctggtaa aagaaggaag   3180
aggggaagtg gagagggcag aggaagtctg ctaacatgtg gtgatgtgga ggagaatcct   3240
ggacctatgg acatgagggt ccctgctcag ctcctggggc tcctgctgct ctggctctca   3300
ggtgccagat gtgagattgt gctgacacaa tctccaggaa ctttgagtct gtctccaggt   3360
gagagggcta cactgtcatg tagggcatca cagtctgttg gaagttctta tctggcttgg   3420
tatcaacaaa agcctgggca ggctccaaga ctgctgattt atggtgcttt ttctagagct   3480
actggaattc ctgataggtt tagtgggagt gggagtggaa cagattttac actgactatt   3540
tctagactgg aaccagaaga ttttgcagtg tattattgtc agcagtatgg gtcttcacct   3600
tggacttttg gtcagggaac taaagtggaa attaagagaa ctgttgctgc tccttcagtt   3660
tttatttttc cacctagtga tgagcagctg aagagtggaa cagcatctgt ggtgtgtctt   3720
ttgaataatt tttatcctag agaagctaag gtgcagtgga aagtggataa tgcattgcag   3780
agtggaaatt cacaagaatc agtgactgag caggattcaa aagatagtac atatagtctt   3840
tcatctactt tgacactgtc taaggctgat tatgagaagc ataaagtgta tgcatgtgag   3900
gtgacacatc aggggctgtc ttcacctgtg acaaagtctt ttaatagagg ggagtgttga   3960
acctgagcta gc                                                       3972
```

<210> SEQ ID NO 14
<211> LENGTH: 3978
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
gcggccgctc gagatctgcg atctaagtaa gcttggcatt ccggtactgt tggtaaagcc     60
accatgtgtc accagcagtt ggtcatctct tggttttccc tggtttttct ggcatctccc    120
ctggtggcca tctgggaact gaagaaagat gtttatgtgg tggaattgga ttggtatcct    180
gatgcccctg gagaaatggt ggtcctcacc tgtgacaccc ctgaagaaga tggtatcacc    240
tggaccttgg accagagcag tgaggtcctg ggctctggca aaaccctgac catccaagtc    300
aaagagtttg gagatgctgg ccagtacacc tgtcacaaag gaggggaggt tctgagccat    360
tccctcctgc tgcttcacaa aaaggaagat ggaatttggt ccactgatat tctgaaggac    420
cagaaagaac ccaaaaataa gacctttctg agatgtgagg ccaagaatta ttctggaaga    480
ttcacctgct ggtggctgac cacaatcagt actgatttga cattcagtgt caaaagcagc    540
agaggctctt ctgaccccca aggggtgacc tgtggagctg ctacactctc tgcagagaga    600
gtcagagggg acaacaagga gtatgagtac tcagtggagt gccaggagga cagtgcctgc    660
ccagctgctg aggagagtct gcccattgag gtcatggtgg atgctgttca caagctcaag    720
tatgaaaact acaccagcag cttcttcatc agggacatca tcaaacctga cccacccaag    780
aacttgcagc tgaagccact gaagaattct aggcaggtgg aggtcagctg ggagtaccct    840
gacacctgga gtactccaca ttcctacttc tccctgacat tctgtgttca ggtccagggc    900
aagagcaaga gagaaaagaa agatagagtc ttcacagaca agacctcagc cacagtcatc    960
tgcaggaaaa atgccagcat tagtgtgagg gcccaggaca gatactatag ctcatcttgg   1020
agtgaatggg catctgtgcc ctgcagtggt ggaggtggaa gtggaggtgg tggatctggg   1080
ggtggaggca gcagaaacct ccctgtggcc actccagacc caggaatgtt cccatgcctt   1140
caccactccc aaaacctgct gagggctgtc agcaacatgc tccagaaggc cagacaaact   1200
ctggaatttt acccttgcac ttctgaagag attgatcatg aagatatcac aaaagataaa   1260
accagcacag tggaggcctg tctgccattg gaactcacca agaatgagag ttgcctgaat   1320
tccagagaga cctctttcat cactaatggg agttgcctgg cctccagaaa gacctctttt   1380
atgatggccc tgtgccttag tagtatttat gaagacttga agatgtacca ggtggagttc   1440
aagaccatga atgcaaagct tctgatggac cctaagaggc agatctttct ggatcaaaac   1500
atgctggcag ttattgatga gctgatgcag gccctgaatt tcaacagtga gactgtgcca   1560
caaaaatcct cccttgaaga acctgatttt tataaaacta aaatcaagct ctgcatcctt   1620
cttcatgctt tcagaattag ggcagtgact attgacagag tgatgagcta tctgaatgct   1680
tccaggagaa agagaggatc ctctggaagt ggagctacta acttcagcct gctgaagcag   1740
gctggagatg tggaggagaa ccctggacct atggagtttg ggctgagctg ggttttcctt   1800
gttgctcttt taagaggtgt ccagtgtcag gtgcagttgg tgcagtctgg agttgaagtg   1860
aaaaagcctg gtgcttcagt gaaggtgagt tgtaaggctt cagggtatac atttactaat   1920
tattatatgt attgggtgag acaggctcct ggtcagggac ttgagtggat gggtggaatt   1980
aatccttcta atggtggaac taattttaat gagaagttta agaatagagt gactctgact   2040
acagatagtt ctactactac tgcttatatg gagctgaagt ctctgcagtt tgatgataca   2100
gctgtgtatt attgtgctag aagagattat agatttgata tgggatttga ttattggggt   2160
caggggacaa cagttacagt tagttcagct tctactaaag gaccatcagt tttcctctg    2220
gcaccatgtt ctaggagtac atcagagtct actgctgcac ttgggtgttt ggtgaaagat   2280
```

```
tattttccag aacctgttac agtgagttgg aatagtggag ctctgacatc aggggttcat   2340

acttttcctg ctgtgttgca gtcatctggg ctgtattctc tgtcatctgt tgtgacagtg   2400

ccaagtagtt cattgggaac taaaacttat acatgtaatg tggatcataa gccttctaat   2460

actaaagtgg ataagagggt ggaatctaag tatggaccac catgtcctcc atgtccagca   2520

cctgaatttc tgggaggacc atctgtgttt ttgtttccac caaaaccaaa agatacattg   2580

atgatttcaa ggacaccaga ggtgacatgt gtggtggtgg atgtgagtca ggaagatcct   2640

gaagtgcaat ttaattggta tgtggatgga gtggaggttc ataatgctaa aactaagcct   2700

agggaagagc agtttaatag tacatatagg gtggtgtctg tgcttacagt tctgcatcaa   2760

gattggctga atggaaaaga gtataagtgt aaagttagta ataaagggct gccttcttca   2820

attgagaaaa caattagtaa ggcaaagggt cagcctagag agcctcaagt ttatacattg   2880

ccaccttctc aggaagagat gacaaagaat caggtgtctc tgacatgttt ggttaagggt   2940

ttttatccat cagatattgc tgtggagtgg gagtcaaatg gtcaaccaga gaataattat   3000

aaaactacac caccagtgct ggattcagat gggtcatttt ttctgtatag tagactgact   3060

gtggataaat caaggtggca ggagggaaat gtgttttctt gttctgtgat gcatgaagct   3120

ctgcataatc attatacaca gaaatcattg agtctgtcat tgggtaagag aaggaagagg   3180

ggaagtggag agggcagagg aagtctgcta acatgtggtg atgtggagga gaatcctgga   3240

cctatggaca tgagggtccc tgctcagctc ctggggctcc tgctgctctg gctctcaggt   3300

gccagatgtg aaattgtgct gactcagagt cctgctacac tgtcattgag tccaggggaa   3360

agagcaacac tgtcttgtag ggcaagtaag ggagtttcaa cttctggtta ttcatatctg   3420

cattggtatc agcagaaacc agggcaggca cctaggttgc tgatttatct ggcatcatat   3480

ttggagagtg gggttcctgc aagattttct ggatctgggt caggaacaga ttttacactg   3540

acaatttcaa gtcttgagcc tgaggatttt gcagtttatt attgtcagca ttcaagagat   3600

ctgcctctga cttttggagg aggtacaaag gttgagatta aaagaactgt ggcagcacct   3660

tcagtgttta tttttcctcc tagtgatgag caattgaaaa gtggtacagc atctgttgtg   3720

tgtctgctta ataattttta tcctagagag gcaaaagttc agtggaaggt tgataatgca   3780

ttgcaatctg ggaattctca agagagtgtt acagaacagg attcaaaaga ttctacttat   3840

tcactgtcat caactctgac actgtcaaag gcagattatg agaagcataa agtgtatgct   3900

tgtgaggtga ctcatcaagg gcttagttct cctgttacta aaagttttaa tagaggtgag   3960

tgttgaacct gagctagc                                                 3978
```

```
<210> SEQ ID NO 15
<211> LENGTH: 3945
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
```

```
gcggccgctc gagatctgcg atctaagtaa gcttggcatt ccggtactgt tggtaaagcc     60

accatgtgtc accagcagtt ggtcatctct tggttttccc tggtttttct ggcatctccc    120

ctggtggcca tctgggaact gaagaaagat gtttatgtgg tggaattgga ttggtatcct    180

gatgcccctg gagaaatggt ggtcctcacc tgtgacaccc ctgaagaaga tggtatcacc    240

tggaccttgg accagagcag tgaggtcctg ggctctggca aaaccctgac catccaagtc    300
```

```
aaagagtttg gagatgctgg ccagtacacc tgtcacaaag gaggggaggt tctgagccat    360
tccctcctgc tgcttcacaa aaaggaagat ggaatttggt ccactgatat tctgaaggac    420
cagaaagaac ccaaaaataa gacctttctg agatgtgagg ccaagaatta ttctggaaga    480
ttcacctgct ggtggctgac cacaatcagt actgatttga cattcagtgt caaaagcagc    540
agaggctctt ctgaccccca aggggtgacc tgtggagctg ctacactctc tgcagagaga    600
gtcagagggg acaacaagga gtatgagtac tcagtggagt gccaggagga cagtgcctgc    660
ccagctgctg aggagagtct gcccattgag gtcatggtgg atgctgttca caagctcaag    720
tatgaaaact acaccagcag cttcttcatc agggacatca tcaaacctga cccacccaag    780
aacttgcagc tgaagccact gaagaattct aggcaggtgg aggtcagctg ggagtaccct    840
gacacctgga gtactccaca ttcctacttc tccctgacat tctgtgttca ggtccagggc    900
aagagcaaga gagaaaagaa agatagagtc ttcacagaca agacctcagc cacagtcatc    960
tgcaggaaaa atgccagcat tagtgtgagg gcccaggaca gatactatag ctcatcttgg   1020
agtgaatggg catctgtgcc ctgcagtggt ggaggtggaa gtggaggtgg tggatctggg   1080
ggtggaggca gcagaaacct ccctgtggcc actccagacc caggaatgtt cccatgcctt   1140
caccactccc aaaacctgct gagggctgtc agcaacatgc tccagaaggc cagacaaact   1200
ctggaatttt acccttgcac ttctgaagag attgatcatg aagatatcac aaaagataaa   1260
accagcacag tggaggcctg tctgccattg gaactcacca agaatgagag ttgcctgaat   1320
tccagagaga cctctttcat cactaatggg agttgcctgg cctccagaaa gacctctttt   1380
atgatggccc tgtgccttag tagtatttat gaagacttga agatgtacca ggtggagttc   1440
aagaccatga atgcaaagct tctgatggac cctaagaggc agatctttct ggatcaaaac   1500
atgctggcag ttattgatga gctgatgcag gccctgaatt tcaacagtga gactgtgcca   1560
caaaaatcct cccttgaaga acctgatttt tataaaacta aaatcaagct ctgcatcctt   1620
cttcatgctt tcagaattag ggcagtgact attgacagag tgatgagcta tctgaatgct   1680
tccaggagaa agagaggatc ctctggaagt ggagctacta acttcagcct gctgaagcag   1740
gctggagatg tggaggagaa ccctggacct atggagtttg ggctgagctg ggttttcctt   1800
gttgctcttt taagaggtgt ccagtgtcag gtgcagctgg tggagagtgg tggggggtg    1860
gtgcaacctg ggaggagtct gagactggat tgtaaggcta gtgggattac tttttcaaat   1920
agtggaatgc attgggtgag acaggctcct gggaaggggc ttgagtgggt tgctgtgatt   1980
tggtatgatg ggtctaaaag gtattatgct gatagtgtga agggtagatt tacaatttct   2040
agggataata gtaaaaatac tctgtttctt cagatgaatt ctttgagagc agaggataca   2100
gcagtttatt attgtgcaac aaatgatgat tattgggggc agggtactct ggttactgtg   2160
tcttctgctt ctacaaaggg gccatcagtg tttcctctgg caccttgtag tagatcaact   2220
agtgagagta cagctgctct ggggtgtctt gtgaaagatt attttcctga acctgtgact   2280
gtgtcttgga attctggagc acttacttca ggtgttcata catttccagc agtgctgcag   2340
agttctgggc tgtatagtct gtcttcagtg gtgacagtgc cttcatcaag tctgggaaca   2400
aaaacttata catgtaatgt ggatcataag ccatcaaata ctaaggtgga taagagagtg   2460
gaatctaagt atggtccacc atgtcctcct tgtccagctc ctgaatttct gggggggacct  2520
agtgtgtttt tgtttccacc taagcctaag gatacactta tgatttcaag aactcctgag   2580
gttacttgtg tggtggtgga tgtgtctcag gaagatccag aagtgcaatt taattggtat   2640
```

gtggatgggg ttgaagtgca taatgcaaaa acaaaaccaa gggaggagca gtttaattct 2700
acttataggg tggtgtctgt gcttacagtg ctgcatcaag attggttgaa tgggaaagaa 2760
tataagtgta aggtttctaa taaggggttg ccttctagta ttgagaagac tatttctaag 2820
gcaaaggggc agcctagaga acctcaagtt tatacacttc ctccaagtca ggaggagatg 2880
actaaaaatc aggtttcact gacatgtctg gtgaaaggat tttatccatc agatattgca 2940
gttgagtggg aatctaatgg gcagcctgag aataattata agactacacc acctgtgctt 3000
gattctgatg gaagtttttt tctgtatagt agactgacag tggataaaag tagatggcag 3060
gaaggtaatg tgtttcttg ttctgtgatg catgaggcac tgcataatca ttatactcaa 3120
aagagtctgt ctctgtctct tggaaagaga aggaagaggg gaagtggaga gggcagagga 3180
agtctgctaa catgtggtga tgtggaggag aatcctggac ctatggacat gagggtccct 3240
gctcagctcc tggggctcct gctgctctgg ctctcaggtg ccagatgtga gattgtgctg 3300
acacagtctc ctgcaactct gtctctgtca cctggggaga gggctactct gtcatgtagg 3360
gctagtcagt ctgtgtcatc atatctggca tggtatcagc aaaaaccagg tcaagctcca 3420
aggctgctga tttatgatgc atcaaatagg gcaactggta ttccagcaag gttttctggg 3480
tcaggaagtg gaacagattt tacactgact attagttctc tggagccaga ggattttgca 3540
gtgtattatt gtcaacagag ttctaattgg ccaagaacat ttgggcaggg tacaaaagtg 3600
gagattaaaa ggacagtggc tgctccttct gtgtttattt ttccaccttc agatgaacaa 3660
cttaaaagtg gtacagcatc agtggtgtgt ctgttgaata atttttatcc aagggaagct 3720
aaagttcagt ggaaagttga taatgcactg cagtctggga attctcagga atctgttaca 3780
gaacaggatt caaaagattc aacttattct ctttctagta ctctgacatt gtctaaggct 3840
gattatgaaa agcataaggt gtatgcttgt gaggtgacac atcagggact tagttcacca 3900
gtgactaaat cttttaatag gggagagtgt tgaacctgag ctagc 3945

<210> SEQ ID NO 16
<211> LENGTH: 3984
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
gcggccgctc gagatctgcg atctaagtaa gcttggcatt ccggtactgt tggtaaagcc 60
accatgtgtc accagcagtt ggtcatctct tggttttccc tggtttttct ggcatctccc 120
ctggtggcca tctgggaact gaagaaagat gtttatgtgg tggaattgga ttggtatcct 180
gatgcccctg gagaaatggt ggtcctcacc tgtgacaccc ctgaagaaga tggtatcacc 240
tggaccttgg accagagcag tgaggtcctg ggctctggca aaaccctgac catccaagtc 300
aaagagtttg gagatgctgg ccagtacacc tgtcacaaag gaggggaggt tctgagccat 360
tccctcctgc tgcttcacaa aaaggaagat ggaatttggt ccactgatat tctgaaggac 420
cagaaagaac ccaaaaataa gacctttctg agatgtgagg ccaagaatta ttctggaaga 480
ttcacctgct ggtggctgac cacaatcagt actgatttga cattcagtgt caaaagcagc 540
agaggctctt ctgaccccca agggggtgacc tgtggagctg ctacactctc tgcagagaga 600
gtcagagggg acaacaagga gtatgagtac tcagtggagt gccaggagga cagtgcctgc 660
ccagctgctg aggagagtct gcccattgag gtcatggtgg atgctgttca caagctcaag 720

-continued

```
tatgaaaact acaccagcag cttcttcatc agggacatca tcaaacctga cccacccaag    780
aacttgcagc tgaagccact gaagaattct aggcaggtgg aggtcagctg ggagtaccct    840
gacacctgga gtactccaca ttcctacttc tccctgacat tctgtgttca ggtccagggc    900
aagagcaaga gagaaaagaa agatagagtc ttcacagaca agacctcagc cacagtcatc    960
tgcaggaaaa atgccagcat tagtgtgagg gcccaggaca gatactatag ctcatcttgg   1020
agtgaatggg catctgtgcc ctgcagtggt ggaggtggaa gtggaggtgg tggatctggg   1080
ggtggaggca gcagaaacct ccctgtggcc actccagacc caggaatgtt cccatgcctt   1140
caccactccc aaaacctgct gagggctgtc agcaacatgc tccagaaggc cagacaaact   1200
ctggaatttt acccttgcac ttctgaagag attgatcatg aagatatcac aaaagataaa   1260
accagcacag tggaggcctg tctgccattg gaactcacca agaatgagag ttgcctgaat   1320
tccagagaga cctctttcat cactaatggg agttgcctgg cctccagaaa gacctctttt   1380
atgatggccc tgtgccttag tagtatttat gaagacttga agatgtacca ggtggagttc   1440
aagaccatga atgcaaagct tctgatggac cctaagaggc agatctttct ggatcaaaac   1500
atgctggcag ttattgatga gctgatgcag gccctgaatt tcaacagtga gactgtgcca   1560
caaaaatcct cccttgaaga acctgatttt tataaaacta aaatcaagct ctgcatcctt   1620
cttcatgctt tcagaattag ggcagtgact attgacagag tgatgagcta tctgaatgct   1680
tccaggagaa agagaggatc ctctggaagt ggagctacta acttcagcct gctgaagcag   1740
gctggagatg tggaggagaa ccctggacct atggagtttg ggctgagctg ggttttcctt   1800
gttgctcttt taagaggtgt ccagtgtgaa gtgcagcttg tggagtcagg aggggggctg   1860
gtgcagcctg gggggagtct gaggctgagt tgtgcagcaa gtggttatac ttttacaaat   1920
tatggaatga attgggtgag acaggctcct ggtaaagggc tggagtgggt tgggtggatt   1980
aatacttata caggggagcc aacatatgct gcagatttta aaaggaggtt tacttttagt   2040
ctggatacat ctaagtcaac agcttatctt cagatgaatt ctcttagggc tgaggataca   2100
gctgtttatt attgtgcaaa gtatcctcat tattatggat catctcattg gtattttgat   2160
gtgtggggtc agggaacact ggtgactgtt agtagtgcta gtactaaagg gccttcagtg   2220
tttccacttg ctccatcaag taagtcaaca tctggaggga ctgctgcact ggggtgtttg   2280
gtgaaggatt attttccaga accagtgact gtttcttgga attctggagc acttacttct   2340
ggtgtgcata catttcctgc agtgttgcag tcatcaggat tgtattcact gtcttctgtg   2400
gtgactgtgc catcaagttc actgggaaca cagacatata tttgtaatgt taatcataaa   2460
ccttctaata caaaggtgga taagaaggtg gaacctaaat cttgtgataa aacacatact   2520
tgtccacctt gtccagctcc agaactgctt gggggtccat ctgtgtttct tttcctccct   2580
aagcctaaag atacacttat gatttctaga acaccagaag ttacttgtgt ggtggtggat   2640
gtgagtcatg aggacccaga agttaagttt aattggtatg tggatggggt tgaagtgcat   2700
aatgctaaaa caaagcctag agaagaacag tataatagta catatagagt ggtgtctgtg   2760
ctgactgtgc tgcatcagga ttggctgaat ggaaaggaat ataaatgtaa ggtgagtaat   2820
aaagctcttc cagctcctat tgagaagaca atttctaagg ctaaggggca accaagggaa   2880
ccacaagtgt atacattgcc accttcaagg gaggagatga ctaagaatca ggtgtctctg   2940
acttgtcttg ttaaagggtt ttatcctagt gatattgctg tggagtggga gtcaaatgga   3000
cagccagaaa ataattataa aacaacacca cctgtgctgg atagtgatgg aagttttttt   3060
ctgtattcta agctgacagt ggataagagt agatggcagc agggtaatgt gtttagttgt   3120
```

```
agtgttatgc atgaagcact gcataatcat tatacacaga aatctctttc tctgtcacca   3180

gggaaaagaa ggaagagggg aagtggagag ggcagaggaa gtctgctaac atgtggtgat   3240

gtggaggaga atcctggacc tatggacatg agggtccctg ctcagctcct ggggctcctg   3300

ctgctctggc tctcaggtgc cagatgtgat attcagatga cacagtcacc aagttctctt   3360

agtgcttctg tgggggatag agttacaatt acttgttcag caagtcagga tattagtaat   3420

tatcttaatt ggtatcagca gaagcctgga aaggctccta aggtgttgat ttattttact   3480

agttcactgc attctggtgt tcctagtagg tttagtgggt ctggatcagg aacagatttt   3540

acactgacaa tttcatcact gcagcctgaa gattttgcta cttattattg tcagcagtat   3600

agtactgttc cttggacatt tgggcagggt acaaaggtgg agattaaaag aactgtggct   3660

gcacctagtg tttttatttt tcctccttca gatgagcagc tgaaatctgg tacagcatct   3720

gttgtttgtc tgcttaataa tttttatcct agggaggcaa aggtgcaatg gaaggtggat   3780

aatgcactgc agagtggaaa ttctcaagaa tcagtgactg agcaagattc taaagattca   3840

acttattctc tgagttcaac tcttactctg tctaaggctg attatgaaaa acataaggtt   3900

tatgcttgtg aggtgactca tcaaggactt agtagtcctg tgacaaagag ttttaatagg   3960

ggggagtgtt gaacctgagc tagc                                          3984
```

<210> SEQ ID NO 17
<211> LENGTH: 3363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gcggccgctc gagatctgcg atctaagtaa gcttggcatt ccggtactgt tggtaaagcc     60

accatgtgtc accagcagtt ggtcatctct tggttttccc tggtttttct ggcatctccc    120

ctggtggcca tctgggaact gaagaaagat gtttatgtgg tggaattgga ttggtatcct    180

gatgcccctg gagaaatggt ggtcctcacc tgtgacaccc ctgaagaaga tggtatcacc    240

tggaccttgg accagagcag tgaggtcctg ggctctggca aaaccctgac catccaagtc    300

aaagagtttg gagatgctgg ccagtacacc tgtcacaaag gaggggaggt tctgagccat    360

tccctcctgc tgcttcacaa aaaggaagat ggaatttggt ccactgatat tctgaaggac    420

cagaaagaac ccaaaaataa gacctttctg agatgtgagg ccaagaatta ttctggaaga    480

ttcacctgct ggtggctgac cacaatcagt actgatttga cattcagtgt caaaagcagc    540

agaggctctt ctgaccccca aggggtgacc tgtggagctg ctacactctc tgcagagaga    600

gtcagagggg acaacaagga gtatgagtac tcagtggagt gccaggagga cagtgcctgc    660

ccagctgctg aggagagtct gcccattgag gtcatggtgg atgctgttca caagctcaag    720

tatgaaaact acaccagcag cttcttcatc agggacatca tcaaacctga cccacccaag    780

aacttgcagc tgaagccact gaagaattct aggcaggtgg aggtcagctg ggagtaccct    840

gacacctgga gtactccaca ttcctacttc tccctgacat tctgtgttca ggtccagggc    900

aagagcaaga gagaaaagaa agatagagtc ttcacagaca agacctcagc cacagtcatc    960

tgcaggaaaa atgccagcat tagtgtgagg gcccaggaca gatactatag ctcatcttgg   1020

agtgaatggg catctgtgcc ctgcagtggt ggaggtggaa gtggaggtgg tggatctggg   1080

ggtggaggca gcagaaacct ccctgtggcc actccagacc caggaatgtt cccatgcctt   1140
```

```
caccactccc aaaacctgct gagggctgtc agcaacatgc tccagaaggc cagacaaact   1200

ctggaatttt acccttgcac ttctgaagag attgatcatg aagatatcac aaaagataaa   1260

accagcacag tggaggcctg tctgccattg gaactcacca agaatgagag ttgcctgaat   1320

tccagagaga cctctttcat cactaatggg agttgcctgg cctccagaaa gacctctttt   1380

atgatggccc tgtgccttag tagtatttat gaagacttga agatgtacca ggtggagttc   1440

aagaccatga atgcaaagct tctgatggac cctaagaggc agatctttct ggatcaaaac   1500

atgctggcag ttattgatga gctgatgcag gccctgaatt tcaacagtga gactgtgcca   1560

caaaaatcct cccttgaaga acctgatttt tataaaacta aaatcaagct ctgcatcctt   1620

cttcatgctt tcagaattag ggcagtgact attgacagag tgatgagcta tctgaatgct   1680

tccaggagaa agagaggatc ctctggaagt ggagctacta acttcagcct gctgaagcag   1740

gctggagatg tggaggagaa ccctggacct atggacatga gggtccctgc tcagctcctg   1800

gggctcctgc tgctctggct ctcaggtgcc agatgtgata ttcagctgac acagagtcct   1860

gcaagtctgg ctgttagtct ggggcaaaga gcaacaatta gttgtaaggc ttctcagtca   1920

gtggattatg atggagatag ttatctgaat tggtatcagc agattcctgg gcagcctcct   1980

aagcttctga tttatgatgc atcaaatctt gtgtcaggaa ttccaccaag gtttctgga    2040

tctggaagtg gaactgattt tactctgaat attcatcctg tggaaaaagt ggatgctgca   2100

acatatcatt gtcagcagtc aactgaggac ccttggacat ttggaggggg gacaaagctt   2160

gagattaagg gggggggagg atcaggaggg ggaggttctg gagggggagg atctcaggtg   2220

cagctgcagc agtctggggc tgagcttgtt agaccaggat cttctgtgaa aatttcatgt   2280

aaagcatcag ggtatgcttt tagttcttat tggatgaatt gggtgaaaca gaggcctggt   2340

cagggactgg agtggattgg acagatttgg cctggggatg gtgatactaa ttataatgga   2400

aagtttaaag gaaaagctac actgacagca gatgagtctt catctactgc atatatgcag   2460

cttagttctc tggcaagtga ggattcagca gtgtattttt gtgcaagaag ggagactaca   2520

acagtgggaa gatattatta tgctatggat tattggggac aaggaacaac tgtgacagtg   2580

tcttctgggg ggggtgggtc tgatattaaa cttcagcaat caggagcaga gcttgcaagg   2640

ccaggtgctt cagtgaaaat gtcatgtaag actagtgggt atacatttac taggtatact   2700

atgcattggg tgaaacaaag accaggacag ggcttgagt ggattggata tattaatcca    2760

agtaggggat atacaaatta taatcaaaag tttaaagata aggctactct gactactgat   2820

aagtcaagtt ctactgctta tatgcagctt tcttctttga cttcagagga ttcagcagtg   2880

tattattgtg caagatatta tgatgatcat tattgtctgg attattgggg acaaggaaca   2940

acactgactg tgtcttctgt ggagggaggg agtggaggat caggtgggtc aggaggtagt   3000

ggaggggtgg atgatattca actgacacag tctccagcta ttatgagtgc atcaccaggg   3060

gagaaggtga caatgacttg tagagcatca agttctgttt cttatatgaa ttggtatcag   3120

cagaagtctg ggacaagtcc taaaagatgg atttatgata cttctaaagt ggcatctgga   3180

gtgccttata ggtttagtgg atctggatct ggaacatctt attcattgac tattagtagt   3240

atggaagcag aagatgcagc aacttattat tgtcagcagt ggtcatcaaa tcctcttaca   3300

tttggagctg ggactaagtt ggaattgaaa catcatcatc atcatcattg aacctgagct   3360

agc                                                                 3363
```

<210> SEQ ID NO 18

<211> LENGTH: 3321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
gcggccgctc gagatctgcg atctaagtaa gcttggcatt ccggtactgt tggtaaagcc     60
accatgtgtc accagcagtt ggtcatctct tggttttccc tggtttttct ggcatctccc    120
ctggtggcca tctgggaact gaagaaagat gtttatgtgg tggaattgga ttggtatcct    180
gatgcccctg gagaaatggt ggtcctcacc tgtgacaccc ctgaagaaga tggtatcacc    240
tggaccttgg accagagcag tgaggtcctg ggctctggca aaaccctgac catccaagtc    300
aaagagtttg gagatgctgg ccagtacacc tgtcacaaag gaggggaggt tctgagccat    360
tccctcctgc tgcttcacaa aaaggaagat ggaatttggt ccactgatat tctgaaggac    420
cagaaagaac ccaaaaataa gacctttctg agatgtgagg ccaagaatta ttctggaaga    480
ttcacctgct ggtggctgac cacaatcagt actgatttga cattcagtgt caaaagcagc    540
agaggctctt ctgaccccca aggggtgacc tgtggagctg ctacactctc tgcagagaga    600
gtcagagggg acaacaagga gtatgagtac tcagtggagt gccaggagga cagtgcctgc    660
ccagctgctg aggagagtct gcccattgag gtcatggtgg atgctgttca caagctcaag    720
tatgaaaact acaccagcag cttcttcatc agggacatca tcaaacctga cccacccaag    780
aacttgcagc tgaagccact gaagaattct aggcaggtgg aggtcagctg ggagtaccct    840
gacacctgga gtactccaca ttcctacttc tccctgacat tctgtgttca ggtccagggc    900
aagagcaaga gagaaaagaa agatagagtc ttcacagaca agacctcagc cacagtcatc    960
tgcaggaaaa atgccagcat tagtgtgagg gcccaggaca gatactatag ctcatcttgg   1020
agtgaatggg catctgtgcc ctgcagtggt ggaggtggaa gtggaggtgg tggatctggg   1080
ggtggaggca gcagaaacct ccctgtggcc actccagacc caggaatgtt cccatgcctt   1140
caccactccc aaaacctgct gagggctgtc agcaacatgc tccagaaggc cagacaaact   1200
ctggaatttt acccttgcac ttctgaagag attgatcatg aagatatcac aaaagataaa   1260
accagcacag tggaggcctg tctgccattg gaactcacca agaatgagag ttgcctgaat   1320
tccagagaga cctctttcat cactaatggg agttgcctgg cctccagaaa gacctctttt   1380
atgatggccc tgtgccttag tagtatttat gaagacttga agatgtacca ggtggagttc   1440
aagaccatga atgcaaagct tctgatggac cctaagaggc agatctttct ggatcaaaac   1500
atgctggcag ttattgatga gctgatgcag gccctgaatt tcaacagtga gactgtgcca   1560
caaaaatcct cccttgaaga acctgatttt tataaaacta aaatcaagct ctgcatcctt   1620
cttcatgctt tcagaattag ggcagtgact attgacagag tgatgagcta tctgaatgct   1680
tccaggagaa agagaggatc ctctggaagt ggagctacta acttcagcct gctgaagcag   1740
gctggagatg tggaggagaa ccctggacct atggagtttg ggctgagctg ggtttttcctt   1800
gttgctcttt taagaggtgt ccagtgtgaa gtgcagcttg tggagtcagg aggggggctg   1860
gtgcagcctg gggggagtct gaggctgagt tgtgcagcaa gtggttatac ttttacaaat   1920
tatggaatga attgggtgag acaggctcct ggtaaagggc tggagtgggt tgggtggatt   1980
aatacttata caggggagcc aacatatgct gcagatttta aaaggaggtt tacttttagt   2040
ctggatacat ctaagtcaac agcttatctt cagatgaatt ctcttagggc tgaggataca   2100
```

```
gctgtttatt attgtgcaaa gtatcctcat tattatggat catctcattg gtattttgat   2160

gtgtggggtc agggaacact ggtgactgtt agtagtgcta gtactaaagg gccttcagtg   2220

tttccacttg ctccatcaag taagtcaaca tctggaggga ctgctgcact ggggtgtttg   2280

gtgaaggatt attttccaga accagtgact gtttcttgga attctggagc acttacttct   2340

ggtgtgcata catttcctgc agtgttgcag tcatcaggat tgtattcact gtcttctgtg   2400

gtgactgtgc catcaagttc actgggaaca cagacatata tttgtaatgt taatcataaa   2460

ccttctaata caaaggtgga taagaaggtg gaacctaaat cttgtgataa aacacatact   2520

ctgagaagga agaggggaag tggagagggc agaggaagtc tgctaacatg tggtgatgtg   2580

gaggagaatc ctggacctat ggacatgagg gtccctgctc agctcctggg gctcctgctg   2640

ctctggctct caggtgccag atgtgatatt cagctgacac agtcaccaag ttctcttagt   2700

gcttctgtgg gggatagagt tacaattact tgttcagcaa gtcaggatat tagtaattat   2760

cttaattggt atcagcagaa gcctggaaag gctcctaagg tgttgattta ttttactagt   2820

tcactgcatt ctggtgttcc tagtaggttt agtgggtctg gatcaggaac agattttaca   2880

ctgacaattt catcactgca gcctgaagat tttgctactt attattgtca gcagtatagt   2940

actgttcctt ggacatttgg gcagggtaca aaggtggaga ttaaaagaac tgtggctgca   3000

cctagtgttt ttatttttcc tccttcagat gagcagctga aatctggtac agcatctgtt   3060

gtttgtctgc ttaataattt ttatcctagg gaggcaaagg tgcaatggaa ggtggataat   3120

gcactgcaga gtggaaattc tcaagaatca gtgactgagc aagattctaa agattcaact   3180

tattctctga gttcaactct tactctgtct aaggctgatt atgaaaaaca taaggtttat   3240

gcttgtgagg tgactcatca aggacttagt agtcctgtga caaagagttt taataggggg   3300

gagtgttgaa cctgagctag c                                           3321
```

<210> SEQ ID NO 19
<211> LENGTH: 3953
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
aagcttggca ttccggtact gttggtaaag ccaccatgtg tcctcagaag ctcaccatct     60

cctggtttgc cattgttttg ctggtgtctc cactcatggc catgtgggag ctggagaaag    120

atgtttatgt tgtggaggtg gactggactc ctgatgcccc tggagaaaca gtgaacctca    180

cctgtgacac ccctgaagaa gatgacatca cctggacctc agaccagaga catggagtca    240

taggctctgg aaagaccctg accatcactg tcaaagagtt tctggatgct ggccagtaca    300

cctgccacaa aggaggggag actctgagcc actcacatct gctgctccac aagaaggaaa    360

atggaatttg gtccactgaa attctgaaaa atttcaaaaa caagactttc ctgaagtgtg    420

aagcaccaaa ttactctgga aggttcacct gctcatggct ggtgcaaaga aacatggact    480

tgaagttcaa catcaagagc agtagcagtt cccctgactc tagggcagtg acatgtggaa    540

tggcctctct gtctgcagag aaggtcacac tggaccaaag ggactatgag aagtattcag    600

tgtcctgcca ggaggatgtc acctgcccaa ctgctgagga gaccctgccc attgaactgg    660

ccttggaagc aaggcagcag aataaatatg agaactacag caccagcttc ttcatcaggg    720

acatcatcaa accagaccct cccaagaact tgcagatgaa gcctttgaag aactcacagg    780
```

```
tggaggtcag ctgggagtac cctgactcct ggagcactcc ccattcctac ttctccctca    840
agttctttgt tagaatccag aggaagaaag aaaagatgaa ggagacagag gaggggtgta    900
accagaaagg tgccttcctg gtggagaaga catctacaga agtccaatgc aaaggaggga    960
atgtctgtgt gcaagctcag gataggtatt acaattcctc atgcagcaag tgggcatgtg   1020
ttccctgcag ggtcagatct ggtggaggtg gaagtggagg tggtggatct gggggtggag   1080
gcagcagggt cattccagtc tctggacctg ccaggtgtct tagccagtcc agaaacctgc   1140
tgaagaccac agatgacatg gtgaagactg ccagagaaaa actgaaacat tattcctgca   1200
ctgctgaaga cattgatcat gaagacatca caagggacca aaccagcaca ttgaagacct   1260
gtctgccact ggaactgcac aagaatgaga gttgcctggc tactagagag acttcttcca   1320
caacaagagg gagctgcctg cccccacaga agacctcttt gatgatgacc ctgtgccttg   1380
gtagcatcta tgaggacttg aagatgtacc agacagagtt ccaggccatc aatgcagcac   1440
ttcagaatca caaccatcag cagatcattc tggacaaggg catgctggtg gccattgatg   1500
agctgatgca gtctctgaat cataatggag agactctgag acagaaacct cctgtgggag   1560
aagcagaccc ttacagagtg aaaatgaagc tctgcatcct gcttcatgcc ttcagcacca   1620
gagtggtgac catcaacagg gtgatgggct atctgagctc tgccagaagg aagagggggat  1680
cctctggaag tggagctact aacttcagcc tgctgaagca ggctggagat gtggaggaga   1740
accctggacc tatgatggtg ttaagtcttc tgtacctgtt gacagccctt cctggtatcc   1800
tgtcagaggt gcagctgcag gagtcaggac caggcctggt gaaaccttct cagagtctgt   1860
ccctgacttg ttctgtcact gggtattcaa ttacatcttc atatagatgg aactggatca   1920
ggaagtttcc agggaatagg ctggagtgga tggggtacat aaattcagct ggtatttcta   1980
attacaatcc atctctgaag agaagaatct ccatcacaag agacacatcc aaaaaccagt   2040
tctttctgca ggttaattct gtgactactg aggatgctgc cacatattac tgtgcaagaa   2100
gtgataatat ggggacaaca ccttttactt attggggtca agggacattg gtgactgtga   2160
gttctgcatc aacaacagca ccatctgtct atccactggc ccctgtgtgt ggagatacaa   2220
ctggctcctc agtgactctg ggatgcctgg tcaagggtta tttccctgag ccagtgacct   2280
tgacctggaa ctctggctcc ctgtccagtg gtgtgcacac cttcccagct gtcctgcagt   2340
ctgacctcta caccctcagc agctcagtga ctgtaacctc tagcacctgg cccagccagt   2400
ccatcacctg caatgtggcc cacccagcaa gcagcaccaa ggtggacaag aaaattgagc   2460
ccagagggcc cacaatcaag ccctgtcctc catgcaaatg cccagcacct aatgcagctg   2520
gtggaccatc tgtcttcatc ttccctccaa agatcaagga tgtactcatg atctccctga   2580
gccccatagt cacatgtgtg gtggtggatg tgagtgagga tgacccagat gtccagatca   2640
gctggtttgt gaacaatgtg gaagtacaca cagctcagac acaaacccat agagaggatt   2700
acaacagtac tctcagggtg gtcagtgccc tccccatcca gcaccaggac tggatgagtg   2760
gcaaggagtt caaatgcaag gtcaacaaca aagacctggg ggcacccatt gagagaacca   2820
tctcaaaacc caaagggtca gtaagagctc cacaggtata tgtcttgcct ccaccagaag   2880
aagagatgac taagaaacag gtcactctga cctgcatggt cacagacttc atgcctgaag   2940
acatttatgt ggagtggacc aacaatggga aaacagagct gaactacaag aacactgaac   3000
cagtcctgga ctctgatggt tcttacttca tgtacagcaa gctgagagtg gaaaagaaga   3060
actgggtgga aagaaatagc tactcctgtt cagtggtcca tgagggtctg cacaatcacc   3120
acacaactaa gagcttctct aggactccaa gaaggaagag ggaagtgga gagggcagag    3180
```

```
gaagtctgct aacatgtggt gatgtggagg agaatcctgg acctatgagg tgcctagctg   3240
agttcctggg gctgcttgtg ctctggattc ctggagccat tggggatatt gtgatgactc   3300
agggtactct gcctaatcct gtgccaagtg ggagtctgt gtctattaca tgtaggagtt   3360
caaagagtct tctttattca gatggaaaaa catatctgaa ttggtatctg cagagacctg   3420
ggcagagtcc tcagctgctg atttattgga tgtctactag ggcatctggg gtgtctgata   3480
gattttctgg tagtggtagt ggtacagatt ttacattgaa gatttctggg gtggaggctg   3540
aagatgtggg tatttattat tgtcagcaag gtctggagtt tccaacattt gggggaggta   3600
ctaagctgga gctgaagaga actgatgctg caccaactgt atccatcttc ccaccatcca   3660
gtgagcagct gacatctgga ggtgcctcag ttgtgtgctt cctgaacaac ttctacccca   3720
aagacatcaa tgtcaagtgg aagattgatg gcagtgaaag acaaaatggg gtcctgaaca   3780
gttggactga tcaggacagc aaagacagca cctacagcat gagcagcacc ctcaccctga   3840
ccaaggatga gtatgaaaga cataacagct atacctgtga ggccactcac aagacatcaa   3900
cttcacccat tgtcaagagc ttcaacagga atgagtgttg aacctgagct agc          3953
```

```
<210> SEQ ID NO 20
<211> LENGTH: 2261
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

aagcttggca ttccggtact gttggtaaag ccaccatgta cagcatgcag ctggcctcct     60
gtgtgacact gacactggtg ctgctggtga actctgcacc cacttcaagc tccacctcaa    120
gctctacagc tgaagcccag cagcagcagc agcagcagca gcagcagcag cagcacctgg    180
agcagctgct gatggacctg caggagctgc tgagcaggat ggagaattac aggaacctga    240
aactccccag gatgctgacc ttcaaatttt acttgcccaa gcaggccaca gaactgaagg    300
atctgcagtg cctggaagat gaacttggac ctctgaggca tgtgctggat ctgactcaaa    360
gcaagagctt tcaactggaa gatgctgaga atttcatcag caatatcaga gtgactgtgg    420
tcaaactgaa gggctctgac aacacatttg agtgccaatt tgatgatgag tcagccactg    480
tggtggactt tctgaggaga tggattgcct tctgtcaaag catcatctca acaagccctc    540
aaagaaggaa gaggggaagt ggagagggca gaggaagtct gctaacatgt ggtgatgtgg    600
aggagaatcc tggacctatg tgtcctcaga agctcaccat ctcctggttt gccattgttt    660
tgctggtgtc tccactcatg gccatgtggg agctggagaa agatgtttat gttgtggagg    720
tggactggac tcctgatgcc cctggagaaa cagtgaacct cacctgtgac acccctgaag    780
aagatgacat cacctggacc tcagaccaga gacatggagt cataggctct ggaaagaccc    840
tgaccatcac tgtcaaagag tttctggatg ctggccagta cacctgccac aaaggagggg    900
agactctgag ccactcacat ctgctgctcc acaagaagga aaatggaatt tggtccactg    960
aaattctgaa aaatttcaaa aacaagactt tcctgaagtg tgaagcacca aattactctg   1020
gaaggttcac ctgctcatgg ctggtgcaaa gaaacatgga cttgaagttc aacatcaaga   1080
gcagtagcag ttcccctgac tctagggcag tgacatgtgg aatggcctct ctgtctgcag   1140
agaaggtcac actggaccaa agggactatg agaagtattc agtgtcctgc caggaggatg   1200
tcacctgccc aactgctgag gagaccctgc ccattgaact ggccttggaa gcaaggcagc   1260
```

```
agaataaata tgagaactac agcaccagct tcttcatcag ggacatcatc aaaccagacc   1320

ctcccaagaa cttgcagatg aagcctttga agaactcaca ggtggaggtc agctgggagt   1380

accctgactc ctggagcact ccccattcct acttctccct caagttcttt gttagaatcc   1440

agaggaagaa agaaaagatg aaggagacag aggaggggtg taaccagaaa ggtgccttcc   1500

tggtggagaa gacatctaca gaagtccaat gcaaaggagg gaatgtctgt gtgcaagctc   1560

aggataggta ttacaattcc tcatgcagca agtgggcatg tgttccctgc agggtcagat   1620

ctggtggagg tggaagtgga ggtggtggat ctgggggtgg aggcagcagg gtcattccag   1680

tctctggacc tgccaggtgt cttagccagt ccagaaacct gctgaagacc acagatgaca   1740

tggtgaagac tgccagagaa aaactgaaac attattcctg cactgctgaa gacattgatc   1800

atgaagacat cacaagggac caaaccagca cattgaagac ctgtctgcca ctggaactgc   1860

acaagaatga gagttgcctg gctactagag agacttcttc cacaacaaga gggagctgcc   1920

tgcccccaca gaagacctct ttgatgatga ccctgtgcct tggtagcatc tatgaggact   1980

tgaagatgta ccagacagag ttccaggcca tcaatgcagc acttcagaat cacaaccatc   2040

agcagatcat tctggacaag ggcatgctgg tggccattga tgagctgatg cagtctctga   2100

atcataatgg agagactctg agacagaaac ctcctgtggg agaagcagac ccttacagag   2160

tgaaaatgaa gctctgcatc ctgcttcatg ccttcagcac cagagtggtg accatcaaca   2220

gggtgatggg ctatctgagc tctgcctaaa cctgagctag c                       2261


<210> SEQ ID NO 21
<211> LENGTH: 3981
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

gcggccgctc gagatctgcg atctaagtaa gcttggcatt ccggtactgt tggtaaagcc     60

accatgtgtc accagcagtt ggtcatctct tggttttccc tggtttttct ggcatctccc    120

ctggtggcca tctgggaact gaagaaagat gtttatgtgg tggaattgga ttggtatcct    180

gatgcccctg gagaaatggt ggtcctcacc tgtgacaccc ctgaagaaga tggtatcacc    240

tggaccttgg accagagcag tgaggtcctg ggctctggca aaaccctgac catccaagtc    300

aaagagtttg gagatgctgg ccagtacacc tgtcacaaag gaggggaggt tctgagccat    360

tccctcctgc tgcttcacaa aaaggaagat ggaatttggt ccactgatat tctgaaggac    420

cagaaagaac ccaaaaataa gacctttctg agatgtgagg ccaagaatta ttctggaaga    480

ttcacctgct ggtggctgac cacaatcagt actgatttga cattcagtgt caaaagcagc    540

agaggctctt ctgaccccca aggggtgacc tgtggagctg ctacactctc tgcagagaga    600

gtcagagggg acaacaagga gtatgagtac tcagtggagt gccaggagga cagtgcctgc    660

ccagctgctg aggagagtct gcccattgag gtcatggtgg atgctgttca caagctcaag    720

tatgaaaact acaccagcag cttcttcatc agggacatca tcaaacctga cccacccaag    780

aacttgcagc tgaagccact gaagaattct aggcaggtgg aggtcagctg ggagtaccct    840

gacacctgga gtactccaca ttcctacttc tccctgacat tctgtgttca ggtccagggc    900

aagagcaaga gagaaaagaa agatagagtc ttcacagaca agacctcagc cacagtcatc    960

tgcaggaaaa atgccagcat tagtgtgagg gcccaggaca gatactatag ctcatcttgg   1020
```

```
agtgaatggg catctgtgcc ctgcagtggt ggaggtggaa gtggaggtgg tggatctggg   1080
ggtggaggca gcagaaacct ccctgtggcc actccagacc caggaatgtt cccatgcctt   1140
caccactccc aaaacctgct gagggctgtc agcaacatgc tccagaaggc cagacaaact   1200
ctggaatttt acccttgcac ttctgaagag attgatcatg aagatatcac aaaagataaa   1260
accagcacag tggaggcctg tctgccattg gaactcacca agaatgagag ttgcctgaat   1320
tccagagaga cctctttcat cactaatggg agttgcctgg cctccagaaa gacctctttt   1380
atgatggccc tgtgccttag tagtatttat gaagacttga agatgtacca ggtggagttc   1440
aagaccatga atgcaaagct tctgatggac cctaagaggc agatctttct ggatcaaaac   1500
atgctggcag ttattgatga gctgatgcag gccctgaatt tcaacagtga gactgtgcca   1560
caaaaatcct cccttgaaga acctgatttt tataaaacta aaatcaagct ctgcatcctt   1620
cttcatgctt tcagaattag ggcagtgact attgacagag tgatgagcta tctgaatgct   1680
tccaggagaa agagaggatc ctctggaagt ggagctacta acttcagcct gctgaagcag   1740
gctggagatg tggaggagaa ccctggacct atggagtttg ggctgagctg ggttttcctt   1800
gttgctcttt taagaggtgt ccagtgtgag gtgcagctgg tggaaagtgg ggggggactt   1860
gtgcagcctg gggggtcact taggctttca tgtgctgctt ctgggtttac atttagtaga   1920
tattggatga gttgggtgag gcaggcacca ggtaaggggc tggagtgggt ggctaatatt   1980
aagcaagatg gttctgagaa gtattatgtg gattctgtta agggtaggtt tacaatttct   2040
agggataatg ctaagaatag tctgtatctg cagatgaatt cacttagagc agaggatact   2100
gcagtgtatt attgtgctag agaagggggt tggtttggtg aattggcatt tgattattgg   2160
ggacagggga ctctggttac agtgtcatca gcaagtacta aggggccatc tgtttttcct   2220
ctggctcctt catcaaagag tacaagtgga ggtacagctg ctcttggttg tcttgtgaag   2280
gattattttc ctgagcctgt gactgtgtca tggaattcag ggctctgac tagtggagtg    2340
catacttttc ctgctgtgct gcagagtagt ggactgtata gtctgagttc tgtggtgaca   2400
gtgccatcat ctagtctggg aacacaaaca tatatttgta atgtgaatca taaaccatct   2460
aatacaaagg ttgataagag agtggagcct aaaagttgtg ataagacaca tacatgtcca   2520
ccatgtcctg ctcctgaatt tgaaggtggt ccaagtgttt ttctgtttcc tcctaagcct   2580
aaggatactc ttatgatttc aaggactcca gaagtgactt gtgtggtggt tgatgttagt   2640
catgaagatc ctgaggttaa atttaattgg tatgtggatg gagttgaagt gcataatgca   2700
aagacaaaac caagggaaga gcagtataat tctacatata gggtggtttc agtgttgaca   2760
gtgctgcatc aagattggct gaatggaaag gaatataaat gtaaggtttc taataaagct   2820
ctgcctgcta gtattgaaaa gacaatttca aaagcaaaag gacaaccaag ggaaccacag   2880
gtttatacac ttcctcctag tagggaagaa atgacaaaga atcaggttag tctgacatgt   2940
ctggtgaaag ggttttatcc ttctgatatt gcagtggaat gggagtcaaa tgggcagcct   3000
gaaaataatt ataagacaac tccaccagtt cttgattcag atggatcttt ttttctgtat   3060
agtaagctga cagtggataa atctaggtgg cagcaaggta atgtgtttag ttgtagtgtt   3120
atgcatgaag cactgcataa tcattatact caaaagtcac tgagtctgtc accagggaaa   3180
agaaggaaga ggggaagtgg agagggcaga ggaagtctgc taacatgtgg tgatgtggag   3240
gagaatcctg gacctatgga catgagggtc cctgctcagc tcctggggct cctgctgctc   3300
tggctctcag gtgccagatg tgagattgtt ctgacacagt ctcctggaac actgtcactg   3360
```

```
tcaccaggag agagggcaac actgtcatgt agagcaagtc agagggtgag tagtagttat   3420

ctggcttggt atcagcagaa accagggcag gcacctagat tgcttattta tgatgcttca   3480

agtagggcta cagggattcc tgatagattt tcagggagtg ggtcagggac agattttaca   3540

ttgacaatta gtaggttgga gcctgaggat tttgctgtgt attattgtca gcagtatgga   3600

tctttgcctt ggacatttgg tcaggggaca aaagtggaga ttaagaggac agtggcagct   3660

ccatctgtgt ttatttttcc tcctagtgat gagcagctta aatctgggac agcttcagtg   3720

gtgtgtttgc ttaataattt ttatccaagg gaggcaaagg tgcagtggaa ggttgataat   3780

gcattgcaga gtggaaattc tcaggagagt gtgacagagc aggattctaa agattcaaca   3840

tattctctgt ctagtacact gactctgtct aaggctgatt atgaaaagca taaggtgtat   3900

gcatgtgagg ttacacatca agggctgtct tctcctgtga caaaatcatt taatagagga   3960

gaatgttgaa cctgagctag c                                             3981
```

<210> SEQ ID NO 22
<211> LENGTH: 3969
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gcggccgctc gagatctgcg atctaagtaa gcttggcatt ccggtactgt tggtaaagcc     60

accatgtgtc accagcagtt ggtcatctct tggttttccc tggtttttct ggcatctccc    120

ctggtggcca tctgggaact gaagaaagat gtttatgtgg tggaattgga ttggtatcct    180

gatgcccctg gagaaatggt ggtcctcacc tgtgacaccc ctgaagaaga tggtatcacc    240

tggaccttgg accagagcag tgaggtcctg ggctctggca aaaccctgac catccaagtc    300

aaagagtttg gagatgctgg ccagtacacc tgtcacaaag gaggggaggt tctgagccat    360

tccctcctgc tgcttcacaa aaaggaagat ggaatttggt ccactgatat tctgaaggac    420

cagaaagaac ccaaaaataa gacctttctg agatgtgagg ccaagaatta ttctggaaga    480

ttcacctgct ggtggctgac cacaatcagt actgatttga cattcagtgt caaaagcagc    540

agaggctctt ctgaccccca aggggtgacc tgtggagctg ctacactctc tgcagagaga    600

gtcagagggg acaacaagga gtatgagtac tcagtggagt gccaggagga cagtgcctgc    660

ccagctgctg aggagagtct gcccattgag gtcatggtgg atgctgttca caagctcaag    720

tatgaaaact acaccagcag cttcttcatc agggacatca tcaaacctga cccacccaag    780

aacttgcagc tgaagccact gaagaattct aggcaggtgg aggtcagctg ggagtaccct    840

gacacctgga gtactccaca ttcctacttc tccctgacat tctgtgttca ggtccagggc    900

aagagcaaga gagaaaagaa agatagagtc ttcacagaca agacctcagc cacagtcatc    960

tgcaggaaaa atgccagcat tagtgtgagg gcccaggaca gatactatag ctcatcttgg   1020

agtgaatggg catctgtgcc ctgcagtggt ggaggtggaa gtggaggtgg tggatctggg   1080

ggtggaggca gcagaaacct ccctgtggcc actccagacc caggaatgtt cccatgcctt   1140

caccactccc aaaacctgct gagggctgtc agcaacatgc tccagaaggc cagacaaact   1200

ctggaatttt acccttgcac ttctgaagag attgatcatg aagatatcac aaaagataaa   1260

accagcacag tggaggcctg tctgccattg gaactcacca agaatgagag ttgcctgaat   1320

tccagagaga cctctttcat cactaatggg agttgcctgg cctccagaaa gacctctttt   1380
```

-continued

```
atgatggccc tgtgccttag tagtatttat gaagacttga agatgtacca ggtggagttc   1440
aagaccatga atgcaaagct tctgatggac cctaagaggc agatctttct ggatcaaaac   1500
atgctggcag ttattgatga gctgatgcag gccctgaatt tcaacagtga gactgtgcca   1560
caaaaatcct cccttgaaga acctgatttt tataaaacta aaatcaagct ctgcatcctt   1620
cttcatgctt tcagaattag ggcagtgact attgacagag tgatgagcta tctgaatgct   1680
tccaggagaa agagaggatc ctctggaagt ggagctacta acttcagcct gctgaagcag   1740
gctggagatg tggaggagaa ccctggacct atggagtttg ggctgagctg ggttttcctt   1800
gttgctcttt taagaggtgt ccagtgtgag gtgcagcttg tggaatctgg ggggggggctg   1860
gtgcagcctg gtggtagtct gagactgtca tgtgctgcta gtgggtttac attttcagat   1920
tcttggattc attgggtgag acaggcacct gggaaaggtc tggagtgggt ggcatggatt   1980
tcaccttatg gggatctac atattatgct gatagtgtga aggggaggtt tacaatttct   2040
gctgatacat ctaagaatac agcttatctt cagatgaatt ctctgagagc tgaagatact   2100
gcagtgtatt attgtgctag gaggcattgg cctggagggt ttgattattg ggtcaaggt   2160
acactggtga ctgttagtag tgctagtact aaaggtcctt ctgtgtttcc actggcacca   2220
agttcaaaga gtacatcagg agggactgca gctctgggtt gtttggtgaa agattatttt   2280
cctgaacctg tgacagtttc atggaattct ggagcactga cttctggagt gcatacattt   2340
cctgctgtgc tgcagtctag tgggttgtat tcattgtcaa gtgtggttac agtgccttca   2400
agttctctgg gtacacagac ttatatttgt aatgtgaatc ataagccaag taatacaaaa   2460
gtggataaga aagttgagcc taaatcatgt gataaaactc atacttgtcc accttgtcct   2520
gctccagagc tgttgggtgg gcctagtgtt tttctttttc caccaaagcc aaaagatact   2580
ttgatgattt caaggacacc agaagtgaca tgtgtggttg ttgatgtttc tcatgaagat   2640
cctgaggtga agtttaattg gtatgttgat ggggttgagg tgcataatgc taagacaaaa   2700
cctagggagg aacagtatgc ttctacatat agagttgtgt cagtgttgac agtgctgcat   2760
caagattggc ttaatgggaa agaatataag tgtaaggttt caaataaggc attgccagct   2820
ccaattgaaa agacaatttc taaggctaag ggtcagccta gggagccaca ggtgtatact   2880
ctgccacctt caagagagga aatgactaag aatcaggtgt cattgacatg tttggtgaaa   2940
ggattttatc cttcagatat tgctgtggaa tgggaatcta atggacaacc agagaataat   3000
tataaaacta ctcctcctgt gctggatagt gatggaagtt tttttctgta ttctaaactt   3060
actgttgata aaagtagatg gcagcaaggt aatgtttttt cttgttctgt gatgcatgaa   3120
gctcttcata atcattatac tcagaagagt ctgagtctgt ctcctggaaa gagaaggaag   3180
aggggaagtg gagagggcag aggaagtctg ctaacatgtg gtgatgtgga ggagaatcct   3240
ggacctatgg acatgagggt ccctgctcag ctcctggggc tcctgctgct ctggctctca   3300
ggtgccagat gtgatattca gatgacacag agtccaagtt cactgtcagc ttctgttggt   3360
gatagagtta ctattacatg tagagcttct caggatgtga gtactgcagt ggcttggtat   3420
cagcagaagc cagggaaggc tccaaagctg ctgatttatt cagcatcatt tctgtattca   3480
ggggtgccat caagattttc aggttctgga agtggaacag attttactct gactatttca   3540
tctctgcaac cagaagattt tgcaacatat tattgtcagc agtatctgta tcatccagca   3600
acatttggtc agggtactaa agtggaaatt aaaaggacag tggcagcacc atcagttttt   3660
atttttccac ctagtgatga acagctgaaa agtgggacag cttcagtggt gtgtctgctt   3720
aataattttt atcctagaga agcaaaagtg cagtggaagg tggataatgc actgcaaagt   3780
```

```
gggaattcac aggaatcagt gacagagcaa gattctaagg attctacata tagtctgtct   3840

tctacattga ctctgtctaa ggcagattat gaaaagcata aagtttatgc atgtgaggtt   3900

actcatcagg gattgtcatc acctgttact aaaagtttta ataggggtga gtgttgaacc   3960

tgagctagc                                                            3969
```

<210> SEQ ID NO 23
<211> LENGTH: 2237
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
aagcttggca ttccggtact gttggtaaag ccaccatgat ggtgttaagt cttctgtacc     60

tgttgacagc ccttcctggt atcctgtcag aggtgcagct gcaggagtca ggaccaggcc    120

tggtgaaacc ttctcagagt ctgtccctga cttgttctgt cactgggtat tcaattacat    180

cttcatatag atggaactgg atcaggaagt ttccagggaa taggctggag tggatggggt    240

acataaattc agctggtatt tctaattaca atccatctct gaagagaaga atctccatca    300

caagagacac atccaaaaac cagttctttc tgcaggttaa ttctgtgact actgaggatg    360

ctgccacata ttactgtgca agaagtgata atatggggac aacacctttt acttattggg    420

gtcaagggac attggtgact gtgagttctg catcaacaac agcaccatct gtctatccac    480

tggcccctgt gtgtggagat acaactggct cctcagtgac tctgggatgc ctggtcaagg    540

gttatttccc tgagccagtg accttgacct ggaactctgg ctccctgtcc agtggtgtgc    600

acaccttccc agctgtcctg cagtctgacc tctacaccct cagcagctca gtgactgtaa    660

cctctagcac ctggcccagc cagtccatca cctgcaatgt ggcccaccca gcaagcagca    720

ccaaggtgga caagaaaatt gagcccagag ggcccacaat caagccctgt cctccatgca    780

aatgcccagc acctaatgca gctggtggac catctgtctt catcttccct ccaaagatca    840

aggatgtact catgatctcc ctgagcccca tagtcacatg tgtggtggtg gatgtgagtg    900

aggatgaccc agatgtccag atcagctggt ttgtgaacaa tgtggaagta cacacagctc    960

agacacaaac ccatagagag gattacaaca gtactctcag ggtggtcagt gccctcccca   1020

tccagcacca ggactggatg agtggcaagg agttcaaatg caaggtcaac aacaaagacc   1080

tgggggcacc cattgagaga accatctcaa aacccaaagg gtcagtaaga gctccacagg   1140

tatatgtctt gcctccacca gaagaagaga tgactaagaa acaggtcact ctgacctgca   1200

tggtcacaga cttcatgcct gaagacattt atgtggagtg gaccaacaat gggaaaacag   1260

agctgaacta caagaacact gaaccagtcc tggactctga tggttcttac ttcatgtaca   1320

gcaagctgag agtggaaaag aagaactggg tggaaagaaa tagctactcc tgttcagtgg   1380

tccatgaggg tctgcacaat caccacacaa ctaagagctt ctctaggact ccaagaagga   1440

agaggggaag tggagagggc agaggaagtc tgctaacatg tggtgatgtg gaggagaatc   1500

ctggacctat gaggtgccta gctgagttcc tggggctgct tgtgctctgg attcctggag   1560

ccattgggga tattgtgatg actcaggcta ctctgcctaa tcctgtgcca agtggggagt   1620

ctgtgtctat tacatgtagg agttcaaaga gtcttcttta ttcagatgga aaaacatatc   1680

tgaattggta tctgcagaga cctgggcaga gtcctcagct gctgatttat tggatgtcta   1740

ctagggcatc tggggtgtct gatagatttt ctggtagtgg tagtggtaca gattttacat   1800
```

```
tgaagatttc tggggtggag gctgaagatg tgggtattta ttattgtcag caaggtctgg   1860

agtttccaac atttggggga ggtactaagc tggagctgaa gagaactgat gctgcaccaa   1920

ctgtatccat cttcccacca tccagtgagc agctgacatc tggaggtgcc tcagttgtgt   1980

gcttcctgaa caacttctac cccaaagaca tcaatgtcaa gtggaagatt gatggcagtg   2040

aaagacaaaa tggggtcctg aacagttgga ctgatcagga cagcaaagac agcacctaca   2100

gcatgagcag caccctcacc ctgaccaagg atgagtatga aagacataac agctatacct   2160

gtgaggccac tcacaagaca tcaacttcac ccattgtcaa gagcttcaac aggaatgagt   2220

gttgaacctg agctagc                                                   2237
```

```
<210> SEQ ID NO 24
<211> LENGTH: 233
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

aagcttggca ttccggtact gttggtaaag ccaccatgct gtctgagatt aagggagtga     60

ttgtgcatag gctggagggg gtgcctatgg gcctgcctaa ttctgtggat gatgctctga    120

ttaatagcac taagatttat tcatattttc catctgtgcc aatgggactg ccccagtata    180

ttaaggctaa tagtaaattt attggcatta ctgaactgtg aacctgagct agc           233
```

```
<210> SEQ ID NO 25
<211> LENGTH: 1949
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

aagcttggca ttccggtact gttggtaaag ccaccatgtg tcctcagaag ctcaccatct     60

cctggtttgc cattgttttg ctggtgtctc cactcatggc catgtgggag ctggagaaag    120

atgtttatgt tgtggaggtg gactggactc ctgatgcccc tggagaaaca gtgaacctca    180

cctgtgacac ccctgaagaa gatgacatca cctggacctc agaccagaga catggagtca    240

taggctctgg aaagaccctg accatcactg tcaaagagtt tctggatgct ggccagtaca    300

cctgccacaa aggaggggag actctgagcc actcacatct gctgctccac aagaaggaaa    360

atggaatttg gtccactgaa attctgaaaa atttcaaaaa caagactttc ctgaagtgtg    420

aagcaccaaa ttactctgga aggttcacct gctcatggct ggtgcaaaga aacatggact    480

tgaagttcaa catcaagagc agtagcagtt cccctgactc tagggcagtg acatgtggaa    540

tggcctctct gtctgcagag aaggtcacac tggaccaaag ggactatgag aagtattcag    600

tgtcctgcca ggaggatgtc acctgcccaa ctgctgagga gaccctgccc attgaactgg    660

ccttggaagc aaggcagcag aataaatatg agaactacag caccagcttc ttcatcaggg    720

acatcatcaa accagaccct cccaagaact tgcagatgaa gcctttgaag aactcacagg    780

tggaggtcag ctgggagtac cctgactcct ggagcactcc ccattcctac ttctccctca    840

agttctttgt tagaatccag aggaagaaag aaaagatgaa ggagacagag gaggggtgta    900

accagaaagg tgccttcctg gtggagaaga catctacaga agtccaatgc aaaggaggga    960
```

-continued

```
atgtctgtgt gcaagctcag gataggtatt acaattcctc atgcagcaag tgggcatgtg   1020

ttccctgcag ggtcagatct ggtggaggtg gaagtggagg tggtggatct gggggtggag   1080

gcagcagggt cattccagtc tctggacctg ccaggtgtct tagccagtcc agaaacctgc   1140

tgaagaccac agatgacatg gtgaagactg ccagagaaaa actgaaacat tattcctgca   1200

ctgctgaaga cattgatcat gaagacatca caagggacca aaccagcaca ttgaagacct   1260

gtctgccact ggaactgcac aagaatgaga gttgcctggc tactagagag acttcttcca   1320

caacaagagg gagctgcctg cccccacaga agacctcttt gatgatgacc ctgtgccttg   1380

gtagcatcta tgaggacttg aagatgtacc agacagagtt ccaggccatc aatgcagcac   1440

ttcagaatca caaccatcag cagatcattc tggacaaggg catgctggtg gccattgatg   1500

agctgatgca gtctctgaat cataatggag agactctgag acagaaacct cctgtgggag   1560

aagcagaccc ttacagagtg aaaatgaagc tctgcatcct gcttcatgcc ttcagcacca   1620

gagtggtgac catcaacagg gtgatgggct atctgagctc tgccagaagg aagaggggat   1680

cctctggaag tggagctact aacttcagcc tgctgaagca ggctggagat gtggaggaga   1740

accctggacc tatgctgtct gagattaagg gagtgattgt gcataggctg gagggggtgc   1800

ctatgggcct gcctaattct gtggatgatg ctctgattaa tagcactaag atttattcat   1860

attttccatc tgtgccaatg ggactgcccc agtatattaa ggctaatagt aaatttattg   1920

gcattactga actgtgaacc tgagctagc                                      1949
```

```
<210> SEQ ID NO 26
<211> LENGTH: 1328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

aagcttggca ttccggtact gttggtaaag ccaccatgag accatctgga actgctggag     60

ctgccttgct ggccctgctg gctgcccttt gtcctgcctc aagagctctg gaggagaaaa    120

agggaaatta tgtggtgact gatcatggtt cttctgtgag agcatgtggg gctgattctt    180

atgagatgga ggaggatggg gtgaggaaat gtaagaagtg tgagggtcct tgtaggaaag    240

tgtgtaatgg aattggaatt ggagaattta aagattctct gagtattaat gctacaaata    300

ttaagcattt taaaaattgt acttctattt ctggagatct gcatattctt cctgtggctt    360

ttagaggaga tagttttact catactcctc ctctggaccc acaggaactg gatattctga    420

aaacagtgaa ggaaattaca gggtttcttc ttattcaagc ctggccagag aataggacag    480

atctgcatgc atttgagaat ctggagatta ttagaggtag gacaaagcag catggtcagt    540

tttcactggc agtggtgagt ctgaatatta catctctggg gctgagatca ctgaaggaaa    600

tttcagatgg tgatgtgatt atttctggaa ataagaatct ttgttatgct aatactatta    660

attggaaaaa actgtttggt acttctggac aaaagactaa gattatttca aatagggga g    720

agaattcttg taaagctaca ggacaagtgt gtcatgcttt gtgttcacca gaggggtgtt    780

ggggtcctga gccaagagat tgtgtgtcat gtaggaatgt gtctagggga agggaatgtg    840

tggataagtg taatcttctg gaaggggaac caagggaatt tgtggaaaat tctgaatgta    900

ttcagtgtca tcctgagtgt ctgccacagg ctatgaatat tacttgtact ggtaggggac    960

ctgataattg tattcaatgt gctcattata ttgatggtcc tcattgtgta aaaacatgtc   1020
```

```
ctgctggagt gatgggagaa aataatactc ttgtgtggaa atatgctgat gctggacatg   1080

tgtgtcatct gtgtcatcca aattgtacat atggatgtac agggcctggt ctggaaggat   1140

gtcctactaa tgggcctaag attccagctg tgggccagga cacccaggag gtcattgtgg   1200

tgccacactc cttgcccttt aaggtggtgg tgatctcagc catcctggcc ctggtggtgc   1260

tcaccatcat ctcccttatc atcctcatca tgctttggca gaagaagcca agatgaacct   1320

gagctagc                                                            1328
```

<210> SEQ ID NO 27
<211> LENGTH: 659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
ccatggagct ggcagctctt tgtaggtggg ggcttctgct tgcactgctt cctccaggag     60

cagcttcagc ttgtcatcaa ctgtgtgcta gggggcattg ttggggacca ggaccaactc    120

agtgtgtgaa ttgttcacag tttctgaggg ggcaggagtg tgtggaggag tgtagggtgc    180

tgcaaggact gcccagggaa tatgttaatg ctaggcattg tctgccatgt catccagaat    240

gtcagccaca gaatggttct gtgacatgtt ttggacctga agctgatcag tgtgtggcat    300

gtgcacatta taaggaccca ccttttttgtg tggcaaggtg tcctagtgga gtgaaacctg    360

atctgtctta tatgccaatt tggaagtttc cagatgagga aggggcttgt cagccttgtc    420

ctatcaattg tacacatagt tgtgtggatc tggatgataa ggggtgtcca gcagagcaaa    480

gggcttctcc actgacagct gtgggccagg acacccagga ggtcattgtg gtgccacact    540

ccttgccctt taaggtggtg gtgatctcag ccatcctggc cctggtggtg ctcaccatca    600

tctcccttat catcctcatc atgctttggc agaagaagcc aagatgaacc tgagctagc     659
```

<210> SEQ ID NO 28
<211> LENGTH: 3044
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
aagcttggca ttccggtact gttggtaaag ccaccatgtg tcctcagaag ctcaccatct     60

cctggtttgc cattgttttg ctggtgtctc cactcatggc catgtgggag ctggagaaag    120

atgtttatgt tgtggaggtg gactggactc ctgatgcccc tggagaaaca gtgaacctca    180

cctgtgacac ccctgaagaa gatgacatca cctggacctc agaccagaga catggagtca    240

taggctctgg aaagaccctg accatcactg tcaaagagtt tctggatgct ggccagtaca    300

cctgccacaa aggaggggag actctgagcc actcacatct gctgctccac aagaaggaaa    360

atggaatttg gtccactgaa attctgaaaa atttcaaaaa caagactttc ctgaagtgtg    420

aagcaccaaa ttactctgga aggttcacct gctcatggct ggtgcaaaga aacatggact    480

tgaagttcaa catcaagagc agtagcagtt cccctgactc tagggcagtg acatgtggaa    540

tggcctctct gtctgcagag aaggtcacac tggaccaaag ggactatgag aagtattcag    600

tgtcctgcca ggaggatgtc acctgcccaa ctgctgagga gaccctgccc attgaactgg    660

ccttggaagc aaggcagcag aataaaatatg agaactacag caccagcttc ttcatcaggg   720
```

-continued

```
acatcatcaa accagaccct cccaagaact tgcagatgaa gcctttgaag aactcacagg    780
tggaggtcag ctgggagtac cctgactcct ggagcactcc ccattcctac ttctccctca    840
agttctttgt tagaatccag aggaagaaag aaaagatgaa ggagacagag gaggggtgta    900
accagaaagg tgccttcctg gtggagaaga catctacaga agtccaatgc aaaggaggga    960
atgtctgtgt gcaagctcag gataggtatt acaattcctc atgcagcaag tgggcatgtg   1020
ttccctgcag ggtcagatct ggtggaggtg gaagtggagg tggtggatct gggggtggag   1080
gcagcagggt cattccagtc tctggacctg ccaggtgtct tagccagtcc agaaacctgc   1140
tgaagaccac agatgacatg gtgaagactg ccagagaaaa actgaaacat tattcctgca   1200
ctgctgaaga cattgatcat gaagacatca caagggacca aaccagcaca ttgaagacct   1260
gtctgccact ggaactgcac aagaatgaga gttgcctggc tactagagag acttcttcca   1320
caacaagagg gagctgcctg cccccacaga agacctcttt gatgatgacc ctgtgccttg   1380
gtagcatcta tgaggacttg aagatgtacc agacagagtt ccaggccatc aatgcagcac   1440
ttcagaatca caaccatcag cagatcattc tggacaaggg catgctggtg gccattgatg   1500
agctgatgca gtctctgaat cataatggag agactctgag acagaaacct cctgtgggag   1560
aagcagaccc ttacagagtg aaaatgaagc tctgcatcct gcttcatgcc ttcagcacca   1620
gagtggtgac catcaacagg gtgatgggct atctgagctc tgccagaagg aagaggggat   1680
cctctggaag tggagctact aacttcagcc tgctgaagca ggctggagat gtggaggaga   1740
accctggacc tatgagacca tctggaactg ctggagctgc cttgctggcc ctgctggctg   1800
ccctttgtcc tgcctcaaga gctctggagg agaaaaaggg aaattatgtg gtgactgatc   1860
atggttcttc tgtgagagca tgtggggctg attcttatga gatggaggag gatggggtga   1920
ggaaatgtaa gaagtgtgag ggtccttgta ggaaagtgtg taatggaatt ggaattggag   1980
aatttaaaga ttctctgagt attaatgcta caaatattaa gcattttaaa aattgtactt   2040
ctatttctgg agatctgcat attcttcctg tggcttttag aggagatagt tttactcata   2100
ctcctcctct ggacccacag gaactggata ttctgaaaac agtgaaggaa attacagggt   2160
ttcttcttat tcaagcctgg ccagagaata ggacagatct gcatgcattt gagaatctgg   2220
agattattag aggtaggaca aagcagcatg gtcagttttc actggcagtg gtgagtctga   2280
atattacatc tctggggctg agatcactga aggaaatttc agatggtgat gtgattattt   2340
ctggaaataa gaatctttgt tatgctaata ctattaattg gaaaaaactg tttggtactt   2400
ctggacaaaa gactaagatt atttcaaata ggggagagaa ttcttgtaaa gctacaggac   2460
aagtgtgtca tgctttgtgt tcaccagagg ggtgttgggg tcctgagcca agagattgtg   2520
tgtcatgtag gaatgtgtct aggggaaggg aatgtgtgga taagtgtaat cttctggaag   2580
gggaaccaag ggaatttgtg gaaaattctg aatgtattca gtgtcatcct gagtgtctgc   2640
cacaggctat gaatattact tgtactggta ggggacctga taattgtatt caatgtgctc   2700
attatattga tggtcctcat tgtgtaaaaa catgtcctgc tggagtgatg ggagaaaata   2760
atactcttgt gtggaaatat gctgatgctg gacatgtgtg tcatctgtgt catccaaatt   2820
gtacatatgg atgtacaggg cctggtctgg aaggatgtcc tactaatggg cctaagattc   2880
cagctgtggg ccaggacacc caggaggtca ttgtggtgcc acactccttg ccctttaagg   2940
tggtggtgat ctcagccatc ctggccctgg tggtgctcac catcatctcc cttatcatcc   3000
tcatcatgct ttggcagaag aagccaagat gaacctgagc tagc                    3044
```

<210> SEQ ID NO 29
<211> LENGTH: 2408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
aagcttggca ttccggtact gttggtaaag ccaccatgtg tcctcagaag ctcaccatct     60
cctggtttgc cattgttttg ctggtgtctc cactcatggc catgtgggag ctggagaaag    120
atgtttatgt tgtggaggtg gactggactc ctgatgcccc tggagaaaca gtgaacctca    180
cctgtgacac ccctgaagaa gatgacatca cctggacctc agaccagaga catggagtca    240
taggctctgg aaagaccctg accatcactg tcaaagagtt tctggatgct ggccagtaca    300
cctgccacaa aggaggggag actctgagcc actcacatct gctgctccac aagaaggaaa    360
atggaatttg gtccactgaa attctgaaaa atttcaaaaa caagactttc ctgaagtgtg    420
aagcaccaaa ttactctgga aggttcacct gctcatggct ggtgcaaaga aacatggact    480
tgaagttcaa catcaagagc agtagcagtt cccctgactc tagggcagtg acatgtggaa    540
tggcctctct gtctgcagag aaggtcacac tggaccaaag ggactatgag aagtattcag    600
tgtcctgcca ggaggatgtc acctgcccaa ctgctgagga gaccctgccc attgaactgg    660
ccttggaagc aaggcagcag aataaatatg agaactacag caccagcttc ttcatcaggg    720
acatcatcaa accagaccct cccaagaact tgcagatgaa gcctttgaag aactcacagg    780
tggaggtcag ctgggagtac cctgactcct ggagcactcc ccattcctac ttctccctca    840
agttctttgt tagaatccag aggaagaaag aaaagatgaa ggagacagag gaggggtgta    900
accagaaagg tgccttcctg gtggagaaga catctacaga agtccaatgc aaaggaggga    960
atgtctgtgt gcaagctcag gataggtatt acaattcctc atgcagcaag tgggcatgtg   1020
ttccctgcag ggtcagatct ggtggaggtg gaagtggagg tggtggatct gggggtggag   1080
gcagcagggt cattccagtc tctggacctg ccaggtgtct tagccagtcc agaaacctgc   1140
tgaagaccac agatgacatg gtgaagactg ccagagaaaa actgaaacat tattcctgca   1200
ctgctgaaga cattgatcat gaagacatca caagggacca aaccagcaca ttgaagacct   1260
gtctgccact ggaactgcac aagaatgaga gttgcctggc tactagagag acttcttcca   1320
caacaagagg gagctgcctg cccccacaga agacctcttt gatgatgacc ctgtgccttg   1380
gtagcatcta tgaggacttg aagatgtacc agacagagtt ccaggccatc aatgcagcac   1440
ttcagaatca caaccatcag cagatcattc tggacaaggg catgctggtg gccattgatg   1500
agctgatgca gtctctgaat cataatggag agactctgag acagaaacct cctgtgggag   1560
aagcagaccc ttacagagtg aaaatgaagc tctgcatcct gcttcatgcc ttcagcacca   1620
gagtggtgac catcaacagg gtgatgggct atctgagctc tgccagaagg aagaggggat   1680
cctctggaag tggagctact aacttcagcc tgctgaagca ggctggagat gtggaggaga   1740
accctggacc tatggagctg gcagctcttt gtaggtgggg gcttctgctt gcactgcttc   1800
ctccaggagc agcttcagct tgtcatcaac tgtgtgctag gggcattgt tggggaccag    1860
gaccaactca gtgtgtgaat tgttcacagt ttctgagggg gcaggagtgt gtggaggagt   1920
gtagggtgct gcaaggactg cccagggaat atgttaatgc taggcattgt ctgccatgtc   1980
atccagaatg tcagccacag aatggttctg tgacatgttt tggacctgaa gctgatcagt   2040
```

```
gtgtggcatg tgcacattat aaggacccac ctttttgtgt ggcaaggtgt cctagtggag   2100

tgaaacctga tctgtcttat atgccaattt ggaagtttcc agatgaggaa ggggcttgtc   2160

agccttgtcc tatcaattgt acacatagtt gtgtggatct ggatgataag ggtgtccag   2220

cagagcaaag ggcttctcca ctgacagctg tgggccagga cacccaggag gtcattgtgg   2280

tgccacactc cttgcccttt aaggtggtgg tgatctcagc catcctggcc ctggtggtgc   2340

tcaccatcat ctcccttatc atcctcatca tgctttggca gaagaagcca agatgaacct   2400

gagctagc                                                            2408
```

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

```
Leu Glu Glu Lys Lys Gly Asn Tyr Val Val Thr Asp His Cys
1               5                   10
```

<210> SEQ ID NO 31
<211> LENGTH: 8
<212> TYPE: PRT
<213> ORGANISM: Unknown
<220> FEATURE:
<223> OTHER INFORMATION: Description of Unknown: Picornavirus 2A ribosome skipping sequence
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 31

```
Asp Xaa Glu Xaa Asn Pro Gly Pro
1               5
```

<210> SEQ ID NO 32
<211> LENGTH: 4
<212> TYPE: PRT
<213> ORGANISM: Unknown
<220> FEATURE:
<223> OTHER INFORMATION: Description of Unknown: Furin cleavage site

<400> SEQUENCE: 32

```
Arg Arg Lys Arg
1
```

<210> SEQ ID NO 33
<211> LENGTH: 5
<212> TYPE: PRT
<213> ORGANISM: Unknown
<220> FEATURE:
<223> OTHER INFORMATION: Description of Unknown: Cathepsin S cleavage sequence

<400> SEQUENCE: 33

```
Pro Met Gly Leu Pro
1               5
```

THERAPEUTIC CONSTRUCTS FOR TREATING CANCER

CROSS-REFERENCE TO RELATED APPLICATIONS

The present application is a National Phase application under 35 U.S.C. § 371 of PCT/US2019/026849, filed Apr. 10, 2019, which claims priority to U.S. Provisional Patent Application No. 62/655,926, filed on Apr. 11, 2018, the contents of which are hereby incorporated by reference in their entirety.

REFERENCE TO SEQUENCE LISTING

The Sequence Listing submitted Oct. 12, 2020, as a text file named "DDP_102_AMD_AFD_Sequence_Listing.txt," created on Oct. 12, 2020, and having a size of 85,055 bytes is hereby incorporated by reference.

FIELD OF TECHNOLOGY

The present technology generally relates to genetic constructs and methods for their use in cancer treatment. In particular, transcription of genes in the constructs is driven by cancer specific promoters so that expression is directly within the tumor microenvironment.

BACKGROUND

Targeted treatment of cancer, and especially metastases, remains an important but elusive goal. Systemic cancer treatments can cause toxicity by inappropriate activation of the immune system in healthy tissues. By precisely directing expression of anti-cancer agents within the cancer cells, higher concentrations of these agents can be achieved within the tumor and lower levels elsewhere. Cancer-cell specific/selective promoters, with broad activity across a wide range of different tumor cells, can be used to direct the expression of single or multiple anti-cancer agents to stimulate local activation of the immune system or release suppression through inhibition of immunological checkpoints.

While investigators use many strategies to provide tumor therapies, high systemic toxicity and non-specific activity limit their acceptance. One such agent is interleukin-12 (IL-12), which is known to have potent anti-tumor activities but has undesirable side effects when administered systemically, either subcutaneously or intravenously (Car, et al., 1999, Tox. Pathology 27, 58-63). Having the ability to limit expression to within the tumor microenvironment will enable therapeutic levels of IL-12 to be produced at the tumor site, where it is most needed therapeutically in diseased tissue, and not elsewhere in healthy tissues in the body.

U.S. Pat. No. 6,737,523 (Fisher, et al.), the complete contents of which is hereby incorporated by reference, describes a progression elevated gene-3 (PEG-3) promoter, which is specific for directing gene expression in cancer cells. The patent describes the use of the promoter to express genes of interest in cancer cells in a specific manner.

United States Patent Publication No. 2009/0311664 describes cancer cell detection using viral vectors that are conditionally competent for expression of a reporter gene only in cancer cells.

There is an ongoing need to develop improved methods of cancer treatment that can be administered systemically while being highly specific for cancer cells and enabling expression of therapeutic agents. Plasmid-based nanoparticles offer the opportunity to deliver such agents. Indeed, the CpG content of such plasmids has been shown to elicit immune activation that can assist an anti-cancer response (Bode et al., 2011, Expert Rev Vaccines 10, 499-511). Therefore, for cancer treatment, it has been perceived as a benefit not to reduce CpG content. However, in other medical indications, there are advantages in developing plasmids that have lower CpG content to reduce methylation and inactivation of expression and to reduce inappropriate inflammation through stimulation of the innate immune system in gene therapy. This application demonstrates that systemic delivery of plasmid nanoparticles, which have been precisely formulated to reduce free polymer and designed to reduce CpG content in the plasmid backbone and the gene of interest, leads to a therapeutic effect in treating cancer. The response is not compromised by a reduction in CpG content. On the contrary, the response is more selective for the expressed gene of interest.

SUMMARY

In one aspect, the present disclosure provides a method for treating cancer in a subject in need thereof, comprising administering to the subject a nucleic acid construct comprising an expression cassette, wherein the expression cassette comprises a cancer-specific promoter and nucleic acid sequences encoding one or more tumor antigens.

In some embodiments, the cancer-specific promoter is the PEG-3 promoter. In some embodiments, the one or more tumor antigens is selected from the group consisting of WT1, MUC1, LMP2, HPV E6 E7, EGFRvIII, HER-2/neu, MAGE A3, p53, NY-ESO-1, PSMA, CEA, MelanA/MART1, Ras mutant, gp100, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, MYCN, RhoC, TRP-2, Mesothelin, PSCA, MAGE A1, CYP1B1, PLAC1, BORIS, ErbB2, Fibroblast activation protein alpha, FR-α, GPC3, IL13-Rα2, Mesothelin, MUC16, PSMA, ROR1, VEGFR2, αvβ6 integrin.

In some embodiments, if multiple tumor antigens are encoded, tumor antigen sequences are separated by a picornavirus 2A ribosome skipping sequence. In some embodiments, the picornavirus ribosome skipping sequence is P2A or T2A.

In some embodiments, the nucleic acid sequences encoding one or more tumor antigens are engineered to have a reduced CpG content compared to their wild-type counterparts. In some embodiments, the nucleic acid construct comprises a CpG-free plasmid backbone.

In some embodiments, the nucleic acid construct is formulated into nanoparticles with a cationic polymer. In some embodiments, the cationic polymer is linear polyethylenimine. In some embodiments, the nanoparticles are prepared at a N/P ratio of 4 or 6. In some embodiments, the nanoparticles are lyophilized.

In some embodiments, the nucleic acid construct is delivered systemically. In some embodiments, the cancer is selected from the group consisting of breast cancer, melanoma, carcinoma of unknown primary (CUP), neuroblastoma, malignant glioma, cervical cancer, colon cancer, hepatocarcinoma, ovarian cancer, lung cancer, pancreatic cancer, and prostate cancer.

In one aspect, the present disclosure provides a nucleic acid construct for the treatment of cancer comprising an expression cassette, wherein the expression cassette comprises a cancer-specific promoter and nucleic acid sequences encoding one or more tumor antigens.

In some embodiments, the cancer-specific promoter is the PEG-3 promoter. In some embodiments, the one or more tumor antigens is selected from the group consisting of WT1, MUC1, LMP2, HPV E6 E7, EGFRvIII, HER-2/neu, MAGE A3, p53, NY-ESO-1, PSMA, CEA, MelanA/MART1, Ras mutant, gp100, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, MYCN, RhoC, TRP-2, Mesothelin, PSCA, MAGE A1, CYP1B1, PLAC1, BORIS, ErbB2, Fibroblast activation protein alpha, FR-α, GPC3, IL13-Rα2, Mesothelin, MUC16, PSMA, ROR1, VEGFR2, αvβ6 integrin.

In some embodiments, if multiple tumor antigens are encoded, tumor antigen sequences are separated by a picornavirus 2A ribosome skipping sequence. In some embodiments, the picornavirus ribosome skipping sequence is P2A or T2A. In some embodiments, the nucleic acid sequences encoding one or more tumor antigens are engineered to have a reduced CpG content compared to their wild-type counterparts. In some embodiments, the nucleic acid construct comprises a CpG-free plasmid backbone.

In some embodiments, the nucleic acid construct is formulated into nanoparticles with a cationic polymer. In some embodiments, the cationic polymer is linear polyethylenimine. In some embodiments, the nanoparticles are prepared at a N/P ratio of 4 or 6. In some embodiments, the nanoparticles are lyophilized.

In some embodiments, the nucleic acid construct is formulated to be delivered systemically. In some embodiments, the cancer is selected from the group consisting of breast cancer, melanoma, carcinoma of unknown primary (CUP), neuroblastoma, malignant glioma, cervical cancer, colon cancer, hepatocarcinoma, ovarian cancer, lung cancer, pancreatic cancer, and prostate cancer.

In one aspect, the present disclosure provides a composition for the treatment of cancer comprising an expression cassette, wherein the expression cassette comprises a cancer-specific promoter and nucleic acid sequences encoding one or more tumor antigens.

In some embodiments, the cancer-specific promoter is the PEG-3 promoter. In some embodiments, the one or more tumor antigens is selected from the group consisting of WT1, MUC1, LMP2, HPV E6 E7, EGFRvIII, HER-2/neu, MAGE A3, p53, NY-ESO-1, PSMA, CEA, MelanA/MART1, Ras mutant, gp100, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, MYCN, RhoC, TRP-2, Mesothelin, PSCA, MAGE A1, CYP1B1, PLAC1, BORIS, ErbB2, Fibroblast activation protein alpha, FR-α, GPC3, IL13-Rα2, Mesothelin, MUC16, PSMA, ROR1, VEGFR2, αvβ6 integrin.

In some embodiments, if multiple tumor antigens are encoded, tumor antigen sequences are separated by a picornavirus 2A ribosome skipping sequence. In some embodiments, the picornavirus ribosome skipping sequence is P2A or T2A.

In some embodiments, the nucleic acid sequences encoding one or more tumor antigens are engineered to have a reduced CpG content compared to their wild-type counterparts. In some embodiments, the nucleic acid construct comprises a CpG-free plasmid backbone.

In some embodiments, the nucleic acid construct is formulated into nanoparticles with a cationic polymer. In some embodiments, the cationic polymer is linear polyethylenimine. In some embodiments, the nanoparticles are prepared at a N/P ratio of 4 or 6. In some embodiments, the nanoparticles are lyophilized.

In some embodiments, the nucleic acid construct is formulated to be delivered systemically. In some embodiments, the cancer is selected from the group consisting of breast cancer, melanoma, carcinoma of unknown primary (CUP), neuroblastoma, malignant glioma, cervical cancer, colon cancer, hepatocarcinoma, ovarian cancer, lung cancer, pancreatic cancer, and prostate cancer.

In some embodiments, the expression cassette further comprises one or more therapeutic genes. In some embodiments, the one or more therapeutic genes is a cytokine, a thymidine kinase, a toxin, a pathogen-associated molecular pattern (PAMP), a danger-associated molecular pattern (DAMP), an immune checkpoint inhibitor gene, or any combination thereof. In some embodiments, the thymidine kinase is HSV1-TK. In some embodiments, the PAMP is flagellin (FliC).

In some embodiments, if multiple therapeutic genes are present, the multiple therapeutic genes are separated by a picornavirus 2A ribosome skipping sequence. In some embodiments, the picornavirus ribosome skipping sequence is P2A or T2A. In some embodiments, the one or more therapeutic genes is engineered to have a reduced CpG content compared to its wild-type counterpart.

In some embodiments, the immune checkpoint inhibitor gene encodes a monoclonal antibody selected from the group consisting of an anti-PD-1 antibody, an anti-PD-L1 antibody, and an anti-CTLA-4 antibody. In some embodiments, the immune checkpoint inhibitor gene encodes an immune checkpoint inhibitor fusion protein comprising a PD-1 fusion protein. In some embodiments, the PD-1 fusion protein comprises a fusion of PD-1 and an immunoglobulin Fc region.

In some embodiments, the cytokine is selected from the group consisting of IL-12, IL-24, IL-2, IL-15, and GM-CSF. In some embodiments, the cytokine is a single chain variant of IL-12 (scIL-12).

In some embodiments, the nucleic acid construct is administered in conjunction with one or more additional therapeutic agents. In some embodiments, the additional therapeutic agent comprises a therapeutic monoclonal antibody. In some embodiments, the additional therapeutic agent comprises one or more CAR T-Cells.

BRIEF DESCRIPTION OF THE DRAWINGS

FIG. 2B shows cytokine expression, as determined by ELISA, in the cell culture supernatant from transfected H460 cells.

FIG. 6B shows a cytotoxicity assay for the effect of ganciclovir, which is phosphorylated by HSV1-TK and causes cell death, resulting in an increase in fluorescence (in RFU) in this assay. The curves show that active HSV1-TK was expressed by plasmids PEG-TK-hIL2-mIL12, PEG-TK-mIL12, PEG-TK-mIL2-mIL12, but not PEG-lucia, in LL/2 cells as determined by an increase in fluorescence, correlating with cell death. FIG. 6C shows a cell proliferation assay demonstrating the proliferation of murine CTLL2 T cells following stimulation with cytokines. The x-axis shows a dilution series of cell culture supernatant and the luminescence reading (in RLU) on the y-axis reflects the relative number of CTLL2 cells 48h after transfection with the listed nanoparticle formulations. Proliferation was observed with all cytokine containing plasmids (PEG-TK-hIL2-mIL12, PEG-mIL2-mIL12, PEG-TK-mIL2-mIL12) but not with PEG-lucia (negative control). FIG. 6D: PBMC proliferation to test functional activity of mIL-12 captured from supernatants of LL/2 cells transfected with the listed nanoparticle formulations. Proliferation of human PBMCs from two human donors (301 and 303) occurred in all formulations expressing murine IL-12 but not in the control (PEG-lucia), which expresses an irrelevant payload. The x-axis shows a dilution series of the culture supernatants used as a source of captured IL-12 and the luminescence reading (in RLU) on the y-axis reflects the relative number of cells.

DETAILED DESCRIPTION

Figure 1A:
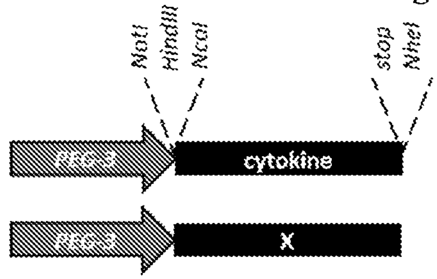
FIGS. 1A-1C are diagrams of exemplary expression cassettes of the constructs of the present technology, disclosed herein, for use in therapeutic applications. Each CpG-free expression cassette is driven by the cancer specific activity of PEG-3. Cassettes are shown including a therapeutic gene, such as a cytokine or a gene such as thymidine kinase (HSV1-TK) or a checkpoint inhibitor and an antigen or toxin or a pathogen associated molecular pattern (PAMP), such as flagellin (FliC). In some embodiments, the cassette comprises nucleic acid sequences encoding a tumor antigen. In some embodiments, the cassette comprises nucleic acid sequences encoding a tumor antigen together with one or more therapeutic genes. X, Y, and Z, and can be any combination of the above. Each is separated by a picornavirus ribosome skipping sequence, such as P2A or T2A and a Furin-GSG site, where removal of the 2A sequence is required. Cloning sites useful in the construction of the expression cassettes are shown.

It is to be appreciated that certain aspects, modes, embodiments, variations and features of the technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this technology belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, a "synergistic therapeutic effect" refers to a greater-than-additive therapeutic effect which is produced by a combination of at least two agents, and which exceeds that which would otherwise result from the individual administration of the agents. For example, lower doses of one or more agents may be used in treating a disease or disorder, resulting in increased therapeutic efficacy and decreased side-effects.

As used herein, a nucleic acids having a "reduced" CpG content refers to a nucleic acid engineered to have a reduced number of CpG motifs compared to its wildtype counterpart. In some embodiments, the reduced CpG nucleic acid is a vector. In some embodiments the vector is used for the delivery of therapeutic genes to a subject. In some embodiments, the vector is a viral vector. In some embodiments, the vector is a plasmid. In some embodiments, the reduced CpG nucleic acid is a therapeutic gene or a reporter gene. In some embodiments, the reduced CpG therapeutic gene is a cytokine. In some embodiments, the reduced CpG cytokine is IL-12.

As used herein, "CpG-free" refers to a nucleic acid construct having no CpG motifs. In some embodiments, the CpG-free nucleic acid is a vector. In some embodiments the vector is used for the delivery of therapeutic genes to a subject. In some embodiments, the vector is a viral vector. In some embodiments, the vector is a plasmid. In some embodiments, a CpG-free plasmid vector is referred to as a "CpG-free plasmid backbone." In some embodiments, the CpG-free nucleic acid is a therapeutic gene or a reporter gene. In some embodiments, the CpG-free therapeutic gene is a cytokine. In some embodiments, the CpG-free cytokine is IL-12.

Compositions and Methods

As discussed herein, cancer-specific promoters can be used for targeted expression of reporter and therapeutic genes in a subject having cancer. For example, U.S. patent application Ser. No. 13/881,777 (U.S. Patent Pub. 20130263296), the contents of which are hereby incorporated by reference, shows that the expression of reporter genes driven by the PEG-3 promoter allows for exceptionally sensitive cancer imaging. The PEG-3 promoter is widely accepted in the field to be a universal cancer-specific promoter and is highly effective for cancer therapeutic applications.

The present disclosure relates to improved therapeutic constructs for the treatment of cancer. In some embodiments, the constructs comprise a PEG-3 promoter and a first gene. In some embodiments, the constructs further comprise a second gene. In some embodiments, the constructs further comprise a third gene.

In some embodiments, the first gene comprises a cytokine. Illustrative cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations or fusions thereof, for example IL-2 and IL-12 both fused to the same Fc domain (see e.g., Hombach &, Abken Oncoimmunology 2; e23205, 2013).

In some embodiments, therapeutic constructs of the present technology comprise other anti-tumor agents, including, for example, but not limited to, interleukins, chemokines, tumor necrosis factor (TNF); interferon-beta and virus-induced human Mx proteins; TNF alpha and TNF beta; human melanoma differentiation-associated gene-7 (mda-7), also known as interleukin-24 (IL-24), various truncated versions of mda-7/IL-24 such as M4; siRNAs and shRNAs targeting important growth regulating or oncogenes which are required by or overexpressed in cancer cells; antibodies such as antibodies that are specific or selective for attacking cancer cells, chemokines important for the recruitment of leukocytes such as CXCL9, CXCL10, or CXCL11, etc.

In some embodiments, the second and/or third gene encodes another cytokine. Illustrative cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations or fusions thereof, for example IL-2 and IL-12 both fused to the same Fc domain (see e.g., Hombach &, Abken Oncoimmunology 2; e23205, 2013). Other anti-tumor agents include: interleukins, chemokines, tumor necrosis factor (TNF); interferon-beta and virus-induced human Mx proteins; TNF alpha and TNF beta; human melanoma differentiation-associated gene-7 (mda-7), also known as interleukin-24 (IL-24), various truncated versions of mda-7/IL-24 such as M4; siRNAs and shRNAs targeting important growth regulating or oncogenes which are required by or overexpressed in cancer cells; antibodies such as antibodies that are specific or selective for attacking cancer cells, etc.

In some embodiments, the second or third gene comprises a nucleic acid sequence encoding a therapeutic molecule. In some embodiments, the therapeutic molecule comprises a cytokine. In some embodiments, the second gene comprises a nucleic acid sequence encoding a fragment of PD-1 or a PD-1 fusion protein. In some embodiments, the fusion includes the extracellular region of PD-1. In some embodiments, the fusion protein comprises a PD-1-immunoglobulin Fc fusion protein. Additionally or alternatively, in some embodiments, the fusion includes one or more of the following molecules: proteins, polypeptides, antibodies or nucleic acid aptamers that bind to and either antagonize or agonise LAG-3, CTLA-4, CD80, CD86, PD-L1, PD-L2, CD48, CD244, TIM-3, Siglecs, HVEM, BTLA, CD160, CD40, CD40L, CD27, 4-1BB, OX40, GITR, VISTA B7-H3, B7-H4, KIRs, NKG2D, NKG2A, MICA, MICB, etc. as described by Mahoney, et al. (Nature Reviews Drug Discovery, 14, 561-565, 2015). In some embodiments, the selection of molecule will depend on whether immune cell activation or repression is required, as is well-known in the art. Additionally or alternatively, in some embodiments, Fc fusions may trap cytokines (see e.g., Huang Current Opinion in Biotechnology, 20:692-699, 2009). Additionally or alternatively, in some embodiments, the fusion protein does not include an Fc sequence. By way of example, but not by way of limitation, in some embodiments, fusion proteins includes PD-1, or the extracellular region of PD-1, and one or more of the NC2 domain of Fibril Associated Collagens with Interrupted Triple helices (FACIT) collagen trimerization domain, non-collagenous domain (NC1) of human collagen XVIII or its trimerization domain (TD) (Boudko and Bachinger J Biol Chem. 287:44536-45, 2012), a C4 bp oligomerization domain (Spencer, et al., PLoS One 7:e33555, 2012) or other coiled-coil domains (Apostolovic, et al., Chem Soc Rev. 39:3541-75, 2010).

Illustrative genes and nucleic acid sequences for use in therapeutic constructs provided herein are described in, for example, U.S. Pat. Nos. 8,163,528, 7,507,792, 5,994,104, 5,846,767, 5,698,520, and 5,629,204.

The present technology provides nucleic acid constructs and methods for their use in cancer treatment. Constructs designed for therapy generally comprise a cancer-specific promoter and a recombinant gene that encodes a therapeutic agent (e.g. a protein or polypeptide whose expression is detrimental to cancer cells) operably linked to the cancer-specific promoter. Thus, targeted killing of cancer cells occurs even when the constructs are administered systemically. These constructs and methods, and various combinations and permutations thereof, are discussed in detail below.

The constructs of the present technology include at least one transcribable element (e.g. a gene composed of sequences of nucleic acids) that is operably connected or linked to a promoter that specifically or selectively drives transcription within cancer cells. Expression of the transcribable element may be inducible or constitutive. Illustrative cancer selective/specific promoters (and or promoter/enhancer sequences) that may be used include but are not limited to: PEG-3, astrocyte elevated gene 1 (AEG-1) promoter, surviving promoter, human telomerase reverse transcriptase (hTERT) promoter, hypoxia-inducible promoter (HIP-1-alpha), DNA damage inducible promoters (e.g. GADD promoters), metastasis-associated promoters (metalloproteinase, collagenase, etc.), ceruloplasmin promoter (Lee, et al., Cancer Res. 64; 1788, 2004), mucin-1 promoters such as DF3/MUC1 (see U.S. Pat. No. 7,247,297), HexII promoter as described in US patent application 2001/00111128; prostate-specific antigen enhancer/promoter (Rodriguez, et al. Cancer Res., 57: 2559-2563, 1997); α-fetoprotein gene promoter (Hallenbeck, et al. Hum. Gene Ther., 10: 1721-1733, 1999); the surfactant protein B gene promoter (Doronin, et al. J. Virol., 75: 3314-3324, 2001); MUC1 promoter (Kurihara, et al. J. Clin. Investig., 106: 763-771, 2000); H19 promoter as per U.S. Pat. No. 8,034,914; those described in issued U.S. Pat. Nos. 7,816,131, 6,897,024, 7,321,030, 7,364,727, and others, etc., as well as derivative forms thereof.

Any promoter that is specific for driving gene expression in cancer cells only, or that is selective for driving gene expression in cancer cells, or at least in cells of a particular type of cancer (so as to treat primary and metastatic cancer in prostate, colon, breast, etc.) may be used in the practice of the present technology. As will be understood by one of skill in the art, promoters that drive gene expression specifically in cancer cells are those that, when operably linked to a gene, function to promote transcription of the gene only in a cancerous cell, and not in non-cancerous cells. As will further be understood by one of skill in the art, promoters that are selective for driving gene expression in cancer cells are those that, when operably linked to a gene, function to promote transcription of the gene to a greater degree in a cancer cell than in a non-cancerous cell. For example, the promoter drives gene expression of the gene at least about 2-fold, or about 3-, 4-, 5-, 6-, 7-, 8-, 9-, or 10-fold, or even about 20-, 30-, 40-, 50-, 60-, 70-, 80-, 90- or 100-fold or more (e.g. 500- or 1000-fold) when located within a cancerous cell than when located within a non-cancerous cell, when measured using standard gene expression measuring techniques that are known to those of skill in the art.

In one embodiment, the promoter is the PEG-3 promoter or a functional derivative thereof. This promoter is described in detail, for example, in issued U.S. Pat. No. 6,737,523, the complete contents of which are herein incorporated by reference. In some embodiments, a "minimal" PEG-3 promoter is utilized, i.e. a minimal promoter that includes a PEA3 protein binding nucleotide sequence, a TATA sequence, and an AP1 protein binding nucleotide sequence, for example, the sequence depicted in, as described in U.S. Pat. No. 6,737,523, Nucleotide sequences which display homology to the PEG-3 promoter and the minimal PEG-3 promoter sequences are also encompassed for use, e.g. those which are at least about 50, 60, 70, 75, 80, 85, 90, 95, 96, 97, 98, or 99% homologous, as determined by standard nucleotide sequence comparison programs which are known in the art.

In some embodiments, the present technology provides vectors for delivery of therapeutic genes. In some embodiments, the vector is a viral vector. In some embodiments, the vector is a non-viral vector.

Illustrative non-viral vectors include but are not limited to, for example, cosmids or plasmids; and, particularly for cloning large nucleic acid molecules, bacterial artificial chromosome vectors (BACs) and yeast artificial chromosome vectors (YACs); as well as liposomes (including targeted liposomes); cationic polymers; ligand-conjugated lipoplexes; polymer-DNA complexes; poly-L-lysine-molossin-DNA complexes; chitosan-DNA nanoparticles; polyethylenimine (PEI, e.g. linear, branched or functionalized PEI)-DNA complexes; PLGA (poly(lactic-co-glycolic acid)); PBAEs (poly β-amino esters); various nanoparticles and/or nanoshells such as multifunctional nanoparticles, metallic nanoparticles or shells (e.g. positively, negatively or neutral charged gold particles, cadmium selenide, etc.); ultrasound-mediated microbubble delivery systems; various dendrimers (e.g. polyphenylene and poly(amidoamine)-based dendrimers; etc (Rodriguez Gascón, et al., 2013, Non-Viral Delivery Systems in Gene Therapy, Gene Therapy—Tools and Potential Applications, Dr. Francisco Martin (Ed.), InTech; Green et al., 2007, Adv. Mater. 19, 2836-2842).

Illustrative viral vectors include but are not limited to: bacteriophages, various baculoviruses, retroviruses, and the like. Those of skill in the art are familiar with viral vectors that are used in "gene therapy" applications, which include but are not limited to: Herpes simplex virus vectors (Geller, et al., Science, 241:1667-1669, 1988); vaccinia virus vectors (Piccini, et al., Meth. Enzymology, 153:545-563, 1987); cytomegalovirus vectors (Mocarski, et al., in Viral Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos, et al., Proc. Natl. Acad. Sci. USA, 85:6460-6464, 1988); Blaese, et al., Science, 270:475-479, 1995; Onodera, et al., J. Virol., 72:1769-1774, 1998); adenovirus vectors (Berkner, Biotechniques, 6:616-626, 1988; Cotten, et al., Proc. Natl. Acad. Sci. USA, 89:6094-6098, 1992; Graham, et al., Meth. Mol. Biol., 7:109-127, 1991; Li, et al., Human Gene Therapy, 4:403-409, 1993; Zabner, et al., Nature Genetics, 6:75-83, 1994); adeno-associated and hybrid adeno-associated virus vectors (Goldman, et al., Human Gene Therapy, 10:2261-2268, 1997; Greelish, et al., Nature Med., 5:439-443, 1999; Wang, et al., Proc. Nati. Acad. Sci. USA, 96:3906-3910, 1999; Snyder, et al., Nature Med., 5:64-70, 1999; Herzog, et al., Nature Med., 5:56-63, 1999; Choi, et al., Curr Gene Ther. 5: 299-310, 2005); retrovirus vectors (Donahue, et al., Nature Med., 4:181-186, 1998; Shackleford, et al., Proc. Natl. Acad. Sci. USA, 85:9655-9659, 1988; U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri, et al., Nature Genetics, 17:314-317, 1997), as well as viruses that are replication-competent conditional to a cancer cell such as oncolytic herpes virus NV 1066 and vaccinia virus GLV-1h68, as described in United States patent application 2009/0311664. In particular, adenoviral vectors may be used, e.g. targeted viral vectors such as those described in published United States patent application 2008/0213220.

Those of skill in the art will recognize that the choice of a particular vector will depend on the intended use, and will be selected according to vector properties known in the art.

Host cells which contain the constructs and vectors of the present technology are also encompassed, e.g. in vitro cells such as cultured cells, or bacterial or insect cells which are used to store, generate or manipulate the vectors, and the like. The constructs and vectors may be produced using recombinant technology or by synthetic means.

In some embodiments nucleic acid constructs described herein comprise a CpG-free plasmid, such as, for example, the Invivogen (San Diego, CA, USA) pCpGfree vector. In some embodiments, constructs comprise a nanoplasmid, such as, for example, the Nature Technology Corporation (Lincoln, NE, USA) NTC9385R plasmid. In some embodiments, the nucleic acid construct comprises a minicircle (Chen, et al., Molecular Therapy 8: 495-500, 2003). Any suitable CpG-free plasmid, nanoplasmid, minicircle, or other expression vector may be used as components of the nucleic acid construct. In some embodiments, the nucleic acid construct is formulated into a nanoparticle.

The present technology provides compositions, which comprise one or more vectors or constructs as described herein and a pharmacologically acceptable carrier. The compositions are usually for systemic administration. The preparation of such compositions is known to those of skill in the art. Typically, they are prepared either as liquid solutions or suspensions, or as solid forms suitable for solution in, or suspension in, liquids prior to administration. The preparation may also be emulsified. The active ingredients may be mixed with excipients that are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present technology may contain any of one or more ingredients known in the art to provide the composition in a form suitable for administration. The final amount of vector in the formulations may vary. However, in general, the amount in the formulations will be from about 1-99%.

Targeted cancer therapy is carried out by administering the constructs, vectors, etc. as described herein to a patient in need thereof. In some embodiments, a gene encoding a therapeutic molecule, e.g. a protein or polypeptide, which is deleterious to cancer cells is operably linked to a cancer-specific promoter as described herein in a "therapeutic construct" or "therapeutic vector." The therapeutic protein may kill cancer cells (e.g. by initiating or causing apoptosis), or may slow their rate of growth (e.g. may slow their rate of proliferation), or may arrest their growth and development or otherwise damage the cancer cells in some manner, or may even render the cancer cells more sensitive to other anti-cancer agents, etc. By way of example only and not by way of limitation, in some embodiments, one or more therapeutic genes (genes encoding therapeutic molecules) are provided in a nucleic acid expression construct, operably linked to a cancer-specific promoter. In some embodiments, the cancer specific promoter is PEG-3. Additionally or alternatively, in some embodiments, the expression construct includes one or more of a nucleic acid sequence encoding an immune checkpoint inhibitor fusion protein.

Genes encoding therapeutic molecules that may be employed in the present technology include but are not limited to, suicide genes, including genes encoding various enzymes; oncogenes; tumor suppressor genes; toxins; cytokines; oncostatins; TRAIL, etc. Illustrative enzymes include, for example, thymidine kinase (TK) and various derivatives thereof; TNF-related apoptosis-inducing ligand (TRAIL), xanthine-guanine phosphoribosyltransferase (GPT); cytosine deaminase (CD); hypoxanthine phosphoribosyl transferase (HPRT); etc. Illustrative tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), AdE1A and nm23. Suitable toxins include *Pseudomonas* exotoxin A and S; diphtheria toxin (DT); *E. coli* LT toxins, Shiga toxin, Shiga-like toxins (SLT-1, -2), ricin, abrin, supporin, gelonin, etc. Suitable cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations or fusions thereof, for example IL-2 and IL-12 both fused to the same Fc domain (see e.g., Hombach &, Abken Oncoimmunology 2; e23205 (2013)). Other anti-tumor agents include: interleukins, chemokines, tumor necrosis factor (TNF); interferon-beta and virus-induced human Mx proteins; TNF alpha and TNF beta; human melanoma differentiation-associated gene-7 (mda-7), also known as interleukin-24 (IL-24), various truncated versions of mda-7/IL-24 such as M4; siRNAs and shRNAs targeting important growth regulating or oncogenes which are required by or overexpressed in cancer cells; antibodies such as antibodies that are specific or selective for attacking cancer cells; etc.

When the therapeutic agent is TK (e.g. viral TK), a TK substrate such as acyclovir; ganciclovir; various thymidine analogs (e.g. those containing o-carboranylalkyl groups at the 3-position (Al-Madhoun, et al., Cancer Res. 64:6280-6, 2004) is administered to the subject. These drugs act as prodrugs, which in themselves are not toxic, but are converted to toxic drugs by phosphorylation by viral TK. Both the TK gene and substrate must be used concurrently to be toxic to the host cancer cell.

In some aspects, the present disclosure provides constructs for cancer therapy comprising a nucleic acid encoding an immune checkpoint inhibitor antibody or fusion protein that bind to any of the following molecules LAG-3, CTLA-4, CD80, CD86, PD-L1, PD-L2, CD48, CD244, TIM-3, Siglecs, HVEM, BTLA, CD160, CD40, CD40L, CD27, 4-1BB, OX40, GITR, VISTA B7-H3, B7-H4, KIRs, NKG2D, NKG2A, MICA, MICB, etc. as described by Mahoney, et al. (Nature Reviews Drug Discovery, 14, 561-565, 2015). In some embodiments, the DNA sequence encodes anti-CTLA-4 (Ipilimumab) or anti-PD-1 (Nivolumab or Pembrolizumab) or anti-PD-L1 (Durvalumab) immune checkpoint inhibitor antibody. In some embodiments, the fusion protein is a programmed cell death-1 (PD-1) fusion protein. In some embodiments, the fusion protein comprises PD-1 fused to an immunoglobulin Fc region.

As known in the art, PD-1 is an immunoglobulin superfamily cell surface receptor expressed on T cells and pro-B cells. Functioning as an immune checkpoint, PD-1 down regulates the activation of T-cells, reducing autoimmunity and promoting self-tolerance. The inhibitory effect of PD-1 is accomplished through a dual mechanism of promoting apoptosis in antigen specific T-cells and reducing apoptosis in regulatory (suppressor) T cells. Agents that inhibit PD-1 function activate the immune system and have been used to treat various types of cancer. Accordingly, it is advantageous to use a PD-1 fusion protein in conjunction with cytokines for the treatment of cancer.

Fusion proteins may be made and tested using techniques known in the art, including methodology outlined herein.

Extracellular regions of receptors have been fused and used as traps for cytokines and growth factors. The extracellular domain of PD-1 can likewise be used as a decoy for its interaction between membrane bound PD-1 and its membrane bound ligands PD-L1 and PD-L2 when expressed in a soluble form. The interaction between PD-1 and its ligands are known to be weak (low μM) (Cheng, et al. J. Biol. Chem. 288: 11771-11785, 2013), therefore fusion of the extracellular domain of PD-1 to the Fc portion of IgG provides additional benefit in that this increases the avidity of the molecule and its apparent affinity.

Additionally, fusion with IgG Fc will increase the molecular mass of the molecule and its hydrodynamic radius, thus increasing the circulating half-life of the PD-1 molecule. Half-life is also extended through binding the Brambell receptor (FcRn), which is involved in recycling antibodies back into circulation following internalization within cells. Fc regions from IgG1-4 or even other immunoglobulin classes such as IgA, IgE, IgM may be used. Exemplary, non-limiting Fc fusions are described by Huang, et al. (Current Opinion in Biotechnology 20:692-699, 2009).

The hinge region of the immunoglobulins positions the Fab regions to contact the antigen but also possesses the ability to interact with Fc receptors and proteins of the complement system. Fusion with the extracellular domain of PD-1 accommodates flexibility of the hinge region although this may be extended or shortened to provide optimal ligand binding. The sequence of the hinge region may be adapted to increase or decrease the affinity for Fcγ receptors as illustrated in WO2009/006520. Other effector properties of the Fc region may also be modified for example US2008/0227958A1, US2004/0132101A1, WO2007/041635A2, amongst others. In some embodiments, cytokines may additionally be fused to the Fc region, as illustrated in immunokine approaches (Pasche and Neri Drug Discovery Today 17, 583-590, 2012).

Simultaneous expression and secretion of the checkpoint inhibitor fusion molecule with HSV1-TK and/or a cytokine has the following benefits. First, the genes will be expressed locally at the tumor site as driven by the cancer specific promoter, therefore the effect will be localized to the tumor microenvironment. This will limit toxicity and immune-related adverse events. Second, irradiation and checkpoint inhibition has been shown to be synergistic (Deng, et al., J Clin Invest. 124:687-695, 2012), therefore conversion of a radiolabeled prodrug and expression of a checkpoint inhibitor within the tumor environment will also be synergistic and localized. Third, expression of a checkpoint inhibitor in isolation has improved CD4+ and CD8+ T cell responses but has limited clinical benefit (Amancha, et al., J Immunol. 191:6060-70, 2013). Engagement of the PD-1 molecule with its ligand on macrophages has been demonstrated to down regulate synthesis of IL-12 (Cho, et al., Immunology Letters 127:39-47, 2009), thus expression of cytokines will help to restore the immune response to abnormal cells. In particular, expression of PD-L1 has been correlated with poor prognosis in NSLC and poor survival of patients with solid tumors (Wang, et al., EJSO 41 450-456, 2015; Wu el al., PLoS ONE 10(6): e0131403, 2015) and blocking the binding of PD-L1 with membrane bound PD-1 or anti-PD-1 or anti-PD-L1 will interfere with the process on immune suppression.

Various TK enzymes or modified or mutant forms thereof may be used in the practice of the present technology, including but not limited to: HSV1-TK, HSV1-sr39TK, mutants with increased or decreased affinities for various substrates, temperature sensitive TK mutants, codon-optimized TK, the mutants described in U.S. Pat. No. 6,451,571 and US patent application 2011/0136221, both of which are herein incorporated by reference; various suitable human TKs and mutant human TKs, etc.

TK substrates that may be used include but are not limited to: analogues of guanosine, such as ganciclovir and valganciclovir; thymidine analogs, such as "fialuridine" i.e. [1-(2-deoxy-2-fluoro-1-D-arabinofuranosyl)-5-iodouracill, also known as "FIAU" and various forms thereof, e.g. 2'-fluoro-2'-deoxy-β-D-5-[$^{125}$I] iodouracil-arabinofuranoside ([$^{125}$I] FIAU), [$^{124}$I]FIAU; thymidine analogs containing o-carboranylalkyl groups at the 3-position, as described by Al Mahoud, et al., (Cancer Res, 64; 6280-6, 2004) and radiolabeled FXAU derivatives such as $^{131}$I-FIAU, $^{211}$At-FAAU.

Other proteins that may function as reporter molecules in the practice of the present technology are transporter molecules which are located on the cell surface or which are transmembrane proteins, e.g. ion pumps which transport various ions across cells membranes and into cells. An illustrative ion pump is the sodium-iodide symporter (NIS) also known as solute carrier family 5, member 5 (SLC5A5). In nature, this ion pump actively transports iodide (I) across e.g. the basolateral membrane into thyroid epithelial cells and can be used with radiolabeled iodide molecules, such as I-131 NaI. Recombinant forms of the transporter encoded by sequences of the constructs described herein may be selectively transcribed in cancer cells, and transport radiolabeled iodine into the cancer cells.

In addition, antibodies may be utilized in the practice of the present technology. For example, the vectors may be designed to express proteins, polypeptides, or peptides which are antigens or which comprise antigenic epitopes for which specific antibodies have been or can be produced. Illustrative antigens include but are not limited to tumor specific proteins that have an abnormal structure due to mutation (proto-oncogenes, tumor suppressors, the abnormal products of ras and p53 genes, etc.); various tumor-associated antigens such as proteins that are normally produced in very low quantities but whose production is dramatically increased in tumor cells (e.g. the enzyme tyrosinase, which is elevated in melanoma cells); various oncofetal antigens (e.g. alphafetoprotein (AFP) and carcinoembryonic antigen (CEA); abnormal proteins produced by cells infected with oncoviruses, e.g. EBV and HPV; various cell surface glycolipids and glycoproteins which have abnormal structures in tumor cells; etc. The antibodies, which may be monoclonal or polyclonal, are labeled with a detectable label and are administered to the patient after or together with the vector. The antibodies encounter and react with the expressed antigens or epitopes, which are produced only (or at least predominantly) in cancer cells, thereby labeling the cancer cells. Conversely, the antibody may be produced by a vector of the present technology, and a labeled antigen may be administered to the patient. In this embodiment, an antibody or a fragment thereof, e.g. a Fab (fragment, antigen binding) segment, or others that are known to those of skill in the art, are employed. In this embodiment, the antigen or a substance containing antigens or epitopes for which the antibody is specific and administered to the subject being treated.

In some embodiments, the present technology provides methods for treating cancer. In some embodiments, the treatment involves administering to a cancer patient, or a subject having cancer, a gene construct (e.g. a plasmid). In this embodiment, expression of the therapeutic gene is mediated by a cancer cell specific or selective promoter as described herein. In some embodiments, the construct expresses at least two therapeutic genes and comprises two promoters in order to prevent or lessen the chance of crossover and recombination within the construct. In some embodiments, the construct comprises a single promoter. In some embodiments, the cancer-specific or cancer selective promoter is the PEG-3 promoter.

In some embodiments, tandem translation mechanisms may be employed, for example, the insertion of one or more internal ribosomal entry site (IRES) into the construct, which permits translation of multiple mRNA transcripts from a single mRNA. In this manner, more than one sequence encoding a therapeutic protein/polypeptide are selectively or specifically produced within the targeted cancer cells.

In some embodiments, the therapeutic gene comprises an IRES sequence. Natural IRES sequences may be used or synthetic or variant sequences that fit with an IRES containing a hairpin loop of a RNRA consensus are used (Robertson, et al., RNA 5:1167-1179, 1999). In some embodiments, therapeutic constructs comprise an IRES tricistronic cassette.

Alternatively, the polypeptides encoded by the constructs of the present technology (e.g. plasmids) may be genetically engineered to contain a contiguous sequence comprising two or more polypeptides of interest (e.g. a reporter and a toxic agent) with an intervening sequence that is cleavable within the cancer cell, e.g. a sequence that is enzymatically cleaved by intracellular proteases, or even that is susceptible to non-enzymatic hydrolytic cleavage mechanisms. In this case, cleavage of the intervening sequence results in production of functional polypeptides, i.e. polypeptides which are able to carry out their intended function, e.g. they are at least 50, 60, 70, 80, 90, or 100% (or possible more) as active as the protein sequences on which they are modeled or from which they are derived (e.g. a sequence that occurs in nature), when measured using standard techniques that are known to those of skill in the art.

In other embodiments of therapy, two different vectors may be administered in a single formulation.

In other embodiments of therapy, the genes of interest are encoded in the genome of a viral vector that is capable of transcription and/or translation of multiple rnRNAs and/or the polypeptides or proteins they encode, by virtue of the properties inherent in the virus. In this embodiment, such viral vectors are genetically engineered to contain and express genes of interest (e.g. therapeutic gene(s)) under the principle control of one or more cancer specific promoters.

In some aspects, the present disclosure provides a nucleic acid construct treatment of cancer. In some embodiments, the construct comprises a cancer-specific promoter, a first gene, a second gene, and a third gene. In some embodiments, the cancer-specific promoter is the PEG-3 promoter. In some embodiments, up to three therapeutic genes are expressed, any suitable cancer-specific promoter, reporter gene, immune checkpoint inhibitor fusion, and therapeutic gene may be used as components of the nucleic acid construct. In some embodiments, the reporter gene comprises a picornavirus 2A ribosome skipping sequence, which is typically characterized by a C-terminal D(V/I)ExNPGP motif (Sharma et al., Nucleic Acids Res., 40: 3143-3151, 2012).

In some embodiments, the therapeutic gene comprises HSV1-TK, an HSV1-TK splice variant, or an HSV1-TK mutant.

In some embodiments, the therapeutic gene comprises sequences encoding an immune checkpoint inhibitor protein that binds to any of the that bind to any of the following molecules LAG-3, CTLA-4, CD80, CD86, PD-L1, PD-L2, CD48, CD244, TIM-3, Siglecs, HVEM, BTLA, CD160, CD40, CD40L, CD27, 4-1BB, OX40, GITR, VISTA B7-H3, B7-H4, KIRs, NKG2D, NKG2A, MICA, MICB, etc. as described by Mahoney, et al. (Nature Reviews Drug Discovery, 14, 561-565). In some embodiments, the DNA sequence encodes anti-CTLA-4 (Ipilimumab) or anti-PD-1 (Nivolumab or Pembrolizumab) immune checkpoint inhibitor antibody. In some embodiments, the fusion protein is a programmed cell death-1 (PD-1) fusion protein. In some embodiments, the fusion protein comprises PD-1 fused to an immunoglobulin Fc region.

In some embodiments, the therapeutic gene comprises a cytokine. In some embodiments, the cytokine is selected from a group consisting of IL-12, IL-24, IL-2, IL-15, and GM-CSF. In some embodiments the cytokine is IL-12, formed as a single chain molecule so that the p35 and p40 proteins are expressed coordinately (Anderson, et al., Human Gene Therapy 8; 1125-1135, 1997).

In some embodiments, a second or third gene comprises of a pathogen associated molecular pattern (PAMP) gene that stimulates the innate immune system, such as flagellin, which is recognized by Toll-like receptor TLR5 on immune cells. In some embodiments, a second or third gene comprises a danger associated molecular pattern (DAMP) gene such as heat shock proteins, HSP70, HSP90, heat shock factor 1 (HSF1), HMGB1 or 5100 proteins. Both PAMPs and DAMPs function through activating receptors (e.g., advanced glycosylation end product-specific receptor (AGER/RAGE), TLRs, NOD1-like receptors (NLRs), RIG-I-like receptors (RLRs), and AIM2-like receptors (ALRs) to produce inflammatory and immune responses (Bartlett, et al., Molecular Cancer 12:103, 2013; Tang, et al., Immunol. Rev., 249, 158-175, 2012; Huang, et al., Ageing Res Rev. S1568-1637(14)00113-5, 2014; Li, et al. Seminars in Cancer Biology, 23: 380-390, 2013).

In some embodiments of the present technology, the nucleic acid construct for treatment of cancer includes one or more tumor associated antigens or a fusion of the one or more antigens. Illustrative tumor associated antigens include, but are not limited to, those referenced by Cheever, et al. (Clin Cancer Res 2009, 15, 5323-3; D'Aloia, et al., Cell Death and Disease 2018, 9, 982), such as WT1, MUC1, LMP2, HPV E6 E7, EGFRvIII, HER-2/neu, MAGE A3, p53, NY-ESO-1, PSMA, CEA, MelanA/MART1, Ras mutant, gp100, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, MYCN, RhoC, TRP-2, Mesothelin, PSCA, MAGE A1, CYP1B1, PLAC1, BORIS, ErbB2, Fibroblast activation protein alpha, FR-α, GPC3, IL13-Rα2, Mesothelin, MUC16, PSMA, ROR1, VEGFR2, αvβ6 integrin. These antigens are known to be expressed in certain tumors and can be targeted by the immune system, or therapeutic agents such as monoclonal antibodies, CAR T-Cells or combinations of therapeutic agents, such as CAR T-Cells and monoclonal antibodies combined by using Fc receptors on CAR T-Cells (targets and CART approaches are reviewed D'Aloia, et al., Cell Death and Disease 9: 982, 2018; Gill, et al., Blood Reviews, 30:157-167, 2016). In some embodiments, the tumor associated antigen is provided in addition to a second or third therapeutic gene. In some embodiments, the tumor associated antigen is provided instead of an immune checkpoint inhibitor fusion (e.g., is provided as the second gene), or instead of a therapeutic gene (e.g., is provided as the third gene).

In some embodiments, CAR T-Cells designed to target a certain tumor antigen (e.g., EGFRvIII) are administered to a subject in combination with a nucleic acid construct comprising an expression cassette, wherein the expression cassette comprises a cancer-specific promoter and a tumor antigen (e.g., EGFRvIII). In some embodiments, CAR T-Cells targeting tumor antigens (e.g., EGFRvIII) are administered to a subject in combination with a nucleic acid construct comprising an expression cassette, wherein the expression cassette comprises a cancer-specific promoter and a tumor antigen (e.g., EGFRvIII), such that a synergistic therapeutic effect is produced.

In some embodiments, the nucleic acid construct for treatment of cancer includes two chains, heavy and light chain of a monoclonal antibody or fragment thereof, such as a Fab fragment or single chain variable fragment (scFv) or bispecific antibody. Such antibodies or fragments target proteins involved in angiogenesis or tumor growth such as VEGF or EGFR or HER2, for example (Finlay and Almagro, Front Immunol. 3:342 (2012); Dubel and Reichert Handbook of Therapeutic Antibodies, 2nd Edition Wiley Blackwell ISBN: 978-3-527-32937-3, 2014; Strohl and Strohl, Therapeutic Antibody Engineering, 1st Edition, Woodhead Publishing ISBN:9781907568374, 2012; Spiess, et al., Molecular Immunology 67: 95-106, 2015). Additionally or alternatively, in some embodiments, non-antibody protein scaffolds such as ankyrin repeats, fibronectin domains or three-helix bundle from Z-domain of Protein A from *S. aureus* amongst others (Hey, et al., Trends in Biotechnology 23: 514-522, 2005; Weidle, et al., Cancer Genomics and Proteomics 10:155-168, 2013) may be expressed under the control of the PEG promoter to tumor associated antigens, receptors or growth factors involved in growth or maintenance of the tumor. In some embodiments, the heavy and light chain of a monoclonal antibody or fragment thereof, such as a Fab fragment or single chain variable fragment (scFv) is provided in addition to a second or third therapeutic gene. In some embodiments, the heavy and light chain of a monoclonal antibody or fragment thereof, such as a Fab fragment or single chain variable fragment (scFv) is provided instead of an immune checkpoint inhibitor fusion (e.g., is provided as the second gene), or instead of a therapeutic gene (e.g., is provided as the third gene).

In some embodiments, the nucleic acid construct for treatment of cancer includes a molecule that induces apoptosis, such as death receptors (DRs, for example TNFR1, CD95, DR3, TRAIL-R1 (CD4), TRAIL-R2 (CD5), and DR6) or their ligands, such as TNF, Fas ligand (FasL), and TNF-related apoptosis-inducing ligand (TRAIL) (Mahmood and Shukla, Experimental Cell Research 316: 887-899, 2010), or p53, p63 or p73 or pro-apoptotic members of the Bcl-2 family such as Bax, Bak, and their subclass of BH-3 only proteins such as BAD, BID, BIM, Hrk, PUMA, BMF, and Noxa related molecules (Tseng, et al., Nat Commun. 6:6456, 2015; Pflaum, et al., Front Oncol. 4: 285, 2014). In some embodiments, the molecule that induces apoptosis is provided in addition to the reporter gene, the immune checkpoint inhibitor fusion and the therapeutic gene. In some embodiments, the molecule that induces apoptosis is provided instead of an immune checkpoint inhibitor fusion (e.g., is provided as the second gene), or instead of a therapeutic gene (e.g., is provided as the third gene).

In some embodiments, the cancer-specific promoter, first gene, second gene, and third gene are cloned into a CpG-free plasmid, such as, for example, the Invivogen pCpGfree vectors. In some embodiments, the cancer-specific promoter, first gene, second gene, and third gene are cloned into a nanoplasmid, such as, for example, the Nature Technology Corporation NTC9385R plasmid. In some embodiments, the nucleic acid construct comprises a minicircle. Any suitable CpG-free plasmid, nanoplasmid, minicircle, or other expression vector may be used as components of the nucleic acid construct. In some embodiments, the nucleic acid construct is modified to be CpG-free. In some embodiments the nucleic acid construct is formulated in to a nanoparticle.

In some embodiments, the nucleic acid construct comprises the components set forth in the Table 1 below.

TABLE 1

| Nucleic Acid Constructs | | | | |
|---|---|---|---|---|
| | Promoter | 1st gene | 2nd gene | 3rd gene |
| 1 | PEG-3 | mIL-12 | | |
| 2 | PEG-3 | HSV1-TK (2A) | mIL-12 | |
| 3 | PEG-3 | SR39 (2A) | mIL-12 | |
| 4 | PEG-3 | hIL-12 | | |
| 5 | PEG-3 | HSV1-TK (2A) | hIL-12 | |
| 6 | PEG-3 | SR-39 (2A) | hIL-12 | |
| 7 | PEG-3 | mIL-2 (2A) | mIL-12 | |
| 8 | PEG-3 | HSV1-TK (2A) | mIL-2 (2A) | mIL-12 |
| 9 | PEG-3 | SR39 (2A) | mIL-2 (2A) | mIL-12 |
| 10 | PEG-3 | hIL-2 (2A) | mIL-12 | |
| 11 | PEG-3 | HSV1-TK (2A) | hIL-2 (2A) | mIL-12 |
| 12 | PEG-3 | SR39 (2A) | hIL-2 (2A) | mIL-12 |
| 13 | PEG-3 | hIL-12 (2A) | hIL-2 | |
| 14 | PEG-3 | hIL-24 | | |
| 15 | PEG-3 | HSV1-TK (2A) | hIL-24 | |

TABLE 1-continued

| Nucleic Acid Constructs | | | | |
|---|---|---|---|---|
| | Promoter | 1st gene | 2nd gene | 3rd gene |
| 16 | PEG-3 | SR39 (2A) | hIL-24 | |
| 17 | PEG-3 | mGM-CSF | | |
| 18 | PEG-3 | HSV1-TK (2A) | mGM-CSF | |
| 19 | PEG-3 | SR39 (2A) | mGM-CSF | |
| 20 | PEG-3 | hGM-CSF | | |
| 21 | PEG-3 | HSV-TK (2A) | hGM-CSF | |
| 22 | PEG-3 | SR39 (2A) | hGM-CSF | |
| 23 | PEG-3 | mIL-12 (2A) | hIL-15 (2A) | |
| 24 | PEG-3 | HSV-TK (2A) | mIL-12 (2A) | hIL-15 |
| 25 | PEG-3 | SR39 (2A) | mIL-12 (2A) | hIL-15 |
| 26 | PEG-3 | cytokine (2A) | checkpoint inhibitor gene* | |
| 27 | PEG-3 | HSV-TK (2A) | cytokine (2A) | checkpoint inhibitor gene* |
| 28 | PEG-3 | SR39 (2A) | cytokine (2A) | checkpoint inhibitor gene* |
| 29 | PEG-3 | checkpoint inhibitor gene* | Cytokine | |
| 30 | PEG-3 | One of (a)-(d)** | PD-1 Fc | |
| 31 | PEG-3 | HSV1-TK (2A) | One of (a)-(d)** | PD-1 Fc |
| 32 | PEG-3 | SR39 (2A) | One of (a)-(d)** | PD-1 Fc |
| 33 | PEG-3 | Cytokine | One of (a)-(d)** | |
| 34 | PEG-3 | One of (a)-(d)** | Cytokine | |
| 35 | PEG-3 | HSV1-TK (2A) | One of (a)-(d)** | Cytokine |
| 36 | PEG-3 | SR39 (2A) | One of (a)-(d)** | Cytokine |

*where the checkpoint inhibitor gene encodes molecules such as an anti-CTLA4, anti-PD1, anti-PD-L1 monoclonal or PD-1 Fc fusion (2A)
**where (a) is a tumor associated antigen, (b) is a heavy and light chain of an antibody, or fragments thereof, (c) is a molecule that induces apoptosis, and (d) is a molecular pattern gene (2A)

The vector compositions (preparations) of the present technology are typically administered systemically, although this need not always be the case, as localized administration (e.g. intratumoral, or into an external orifice such as the vagina, the nasopharyngeal region, the mouth; or into an internal cavity such as the thoracic cavity, the cranial cavity, the abdominal cavity, the spinal cavity, etc.) is not excluded. For systemic distribution of the vector, routes of administration include but are not limited to: intravenous, by injection, transdermal, via inhalation or intranasally, or via injection or intravenous administration of a cationic polymer-based vehicle (e.g. in vivo-jetPEI®), liposomal delivery, which when combined with targeting moieties will permit enhanced delivery. The ultrasound-targeted microbubble-destruction technique (UTMD) may also be used to deliver therapeutic agents (Dash, et al. Proc Natl Acad Sci USA. 108:8785-90, 2011); hydroxyapatite-chitosan nanocomposites (Venkatesan, et al. Biomaterials. 32:3794-806, 2011); and others (Dash, et al. Discov Med. 11:46-56, 2011); etc. Any method that is known to those of skill in the art, and which is commensurate with the type of construct that is employed, may be utilized. In addition, the compositions may be administered in conjunction with other treatment modalities known in the art, such as various chemotherapeutic agents such as Pt drugs, substances that boost the immune system, antibiotic agents, and the like; or with other detection or imaging methods (e.g. to confirm or provide improved or more detailed imaging, e.g. in conjunction with mammograms, X-rays, Pap smears, prostate specific antigen (PSA) tests, etc.

In some embodiments, the nucleic acid will be formulated into nanoparticles using the cationic polymer linear PEI at N/P ratio of 4 or 6. In some embodiments the nanoparticles are lyophilized in a cryoprotectant sugar solution, such as 9.5% Trehalose.

Those of skill in the art will recognize that the amount of a construct or vector that is administered will vary from patient to patient, and possibly from administration to administration for the same patient, depending on a variety of factors, including but not limited to: weight, age, gender, overall state of health, the particular disease being treated, and concomitant treatment, thus the amount and frequency of administration is best established by a health care professional such as a physician. Typically, optimal or effective tumor-inhibiting or tumor-killing amounts are established e.g. during animal trials and during standard clinical trials. Those of skill in the art are familiar with conversion of doses e.g. from a mouse to a human, which is generally done according to body surface area, as described by Freireich, et al. (Cancer Chemother Rep 50:219-244, 1996); and see Tables 2 and 3 below, which are taken from the website located at dtp,nci.nih.gov.

TABLE 2

| Conversion factors in mg/kg | | | | | |
|---|---|---|---|---|---|
| | Mouse wt. 20 g | Rat wt 150 g | Monkey wt 3 kg | Dog wt 8 kg | Human wt 60 kg |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 1 2/3 | 1 | 1/2 |
| Man | 12 | 7 | 3 | 2 | 1 |

For example, given a dose of 50 mg/kg in the mouse, an appropriate dose in a monkey would be 50 mg/kg×¼=13 mg/kg/; or similarly a dose of about 1.2 mg/kg in the mouse is about 0.1 mg/kg for a human.

TABLE 3

| Representative Surface Area to Weight Ratios | | | |
|---|---|---|---|
| Species | Body Weight (kg) | Surface Area (sq. m.) | Km factor |
| Mouse | 0.02 | 0.0066 | 3.0 |
| Rat | 0.15 | 0.025 | 5.9 |
| Monkey | 3.0 | 0.24 | 12 |
| Dog | 8.0 | 0.4 | 20 |
| Human, child | 20 | 0.8 | 25 |
| Human, adult | 60 | 1.6 | 37 |

To express the dose as the equivalent mg/sq.m. dose, multiply the dose by the appropriate factor. In adult humans, 100 mg/kg is equivalent to 100 mg/kg×37 kg/sq.m.=3700 mg/sq.m.

In general, for treatment methods, the amount of a vector such as a plasmid will be in the range of from about 0.01 to about 5 mg/kg or from about 0.05 to about 1 mg/kg (e.g. about 0.3 mg/kg) of plasmid, and from about $10^5$ to about $10^{20}$ infectious units (IUs), or from about $10^8$ to about $10^{13}$ IUs for a viral-based vector.

Typically, cancer treatment requires repeated administrations of the compositions. For example, administration may be daily or every few days, (e.g. every 2, 3, 4, 5, or 6 days), or weekly, bi-weekly, or every 3-4 weeks, or monthly, or any combination of these, or alternating patterns of these. For example, a "round" of treatment (e.g. administration one a week for a month) may be followed by a period of no administration for a month, and then followed by a second round of weekly administration for a month, and so on, for any suitable time periods, as required to optimally treat the patient.

The subjects or patients to whom the compositions of the present technology are administered are typically mammals, frequently humans, but this need not always be the case. Veterinary applications are also contemplated, such as dogs, for example.

The constructs and methods of the present technology are not specific for any one type of cancer. As will be understood by one of skill in the art, "cancer" refers to malignant neoplasms in which cells divide and grow uncontrollably, forming malignant tumors, and invade nearby parts of the body. Cancer may also spread or metastasize to more distant parts of the body through the lymphatic system or bloodstream. The constructs and methods of the present technology may be employed to image, diagnose, treat, monitor, etc. any type of cancer, tumor, neoplastic or tumor cells including but not limited to: osteosarcoma, ovarian carcinoma, breast carcinoma, melanoma, hepatocarcinoma, lung cancer, brain cancer, colorectal cancer, hematopoietic cell, prostate cancer, cervical carcinoma, retinoblastoma, esophageal carcinoma, bladder cancer, neuroblastoma, renal cancer, gastric cancer, pancreatic cancer, and others.

In addition, the present technology may also be applied to the treatment of benign tumors, which are generally recognized as not invading nearby tissue or metastasizing. Illustrative benign tumors include but are not limited to moles, uterine fibroids, etc.

Combinatorial Therapies

The constructs and methods of the present technology may be used in combination with one or more additional cancer treatments as known in the art. For example, treatments comprising the administration of molecules that inhibit pathways such as BRAF/MEK, AKT-PI3K-mTOR, Wnt-β-catenin, EGF/EGFR, chemotherapy agents, radiotherapy or inhibitors of checkpoint molecules, angiogenesis or indoleamine 2,3-dioxygenase, or inhibitors of FOXP3 for example (Lozano, et al., Oncotarget, 8, 71709-71724, 2017; immunotherapy combinations reviewed by Ott, et al., Journal for ImmunoTherapy of Cancer, 5:16, 2017; interleukin 12 combinations reviewed by Lasek and Jakóbisiak, Interleukin 12: Antitumor Activity and Immunotherapeutic Potential in Oncology, SpringerBriefs in Immunology, Springer International Publishing AG ISBN 978-3-319-46906-5, 2016).

Methods and compositions of the present technology and one or more additional cancer treatments may be administered to subject in need thereof separately, simultaneously, or sequentially.

EXAMPLES

Example 1: Cloning of Therapeutic Constructs

Removal of CpG sites from a therapeutic plasmid is not an obvious requirement in cancer therapeutics. It has been reported that formulated plasmids containing IL-12 and LacZ (4.5% and 7.4% CpG, respectively) expressed from a CMV promoter and delivered using linear PEI had a similar response to each other in a model of LLC (LL/2) tumors in C57BL/6 mice, therefore demonstrating the immune-stimulatory effect of CpG sites irrespective of payload (Rodrigo-Garzon, et al., Cancer Gene Therapy, 17; 20-27, 2010). In that study, the reduction of CpG sites was not investigated and it was concluded that in the case of a lung cancer model using LLC (LL/2) cells, the antitumoral activity is mainly driven by the activation of the innate immune system by the CpG motifs. This activation was not specifically directed at the tumors as the particles were not targeted nor was the gene expression selective for cancerous cells. Therefore, expression from the plasmid payload could occur outside of the region of the tumor, potentially introducing toxicity associated with high systemic levels of cytokine.

It is the intention of the work described within this current application to limit the biological effects to the expressed payload produced within the tumor microenvironment, i.e., to the proteins expressed under the control of the PEG-3 promoter, which is activated within tumor cells, rather than to innate immunity driven solely by the CpG content of the DNA encapsulated within the particles. Hence, CpG-free ORFs (open reading frames) were designed and cloned into the plasmid and subsequently formulated into nanoparticles.

All therapeutic constructs were modified to remove CpG motifs and codon optimized. For all expression cassettes, the termini of the sequences were modified to include a 5' restriction enzyme site compatible with the plasmid/PEG-3 promoter sequence and a stop codon followed by a NheI site at the 3' end, to insert into CpG free expression plasmids, such as pCpGfree-N-mcs (Invivogen, San Diego, California, US), or other CpG free plasmids, in which the PEG-3 promoter was cloned in place of the mCMV enhancer and EF1 promoter.

Cytokines were cloned in isolation or in combination with additional gene payloads such as CpG-free HSV-1 TK (TK) (SEQ ID NO: 1) or modified CpG-free thymidine kinase (SR39) (SEQ ID NO: 2) expressed from a single PEG-3 promoter. These cytokines include: murine IL-12 (mIL12); TK and murine IL-12 (TK-mIL12); human IL-12 (hIL12); TK and human IL-12 (TK-hIL12); murine IL-2 and murine IL-12 (mIL2-mIL12); TK and murine IL-2 and murine IL-12 (TK-mIL2-mIL12); TK and human IL-2 and murine IL-12 (TK-hIL2-mIL12); human IL-12 and human IL-2 (hIL12-hIL2); human IL-24 (hIL24); TK and murine GM-CSF (TK-mGM-CSF); TK and human GM-CSF (TK-hGM-CSF); mIL-12 and hIL-15 (mIL12-hIL15); TK and mIL-12 and hIL-15 (TK-mIL12-hIL15); TK and murine IL-12 and flagellin (FliC) (TK-mIL12-Flag).

Figure 1B:
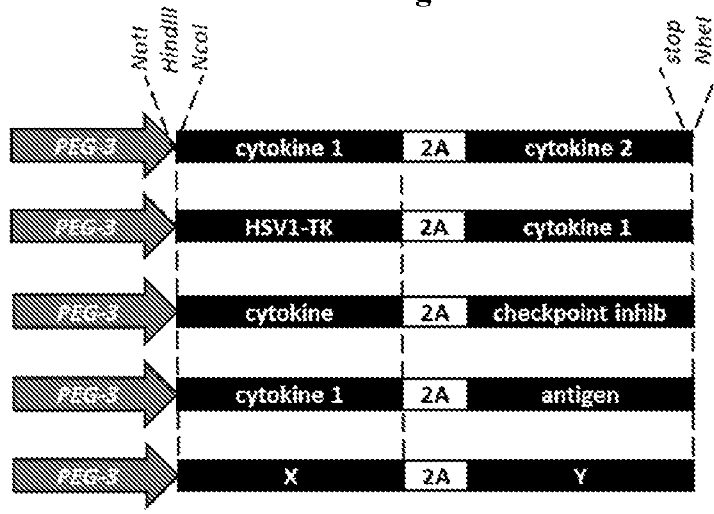
Figure 1C:
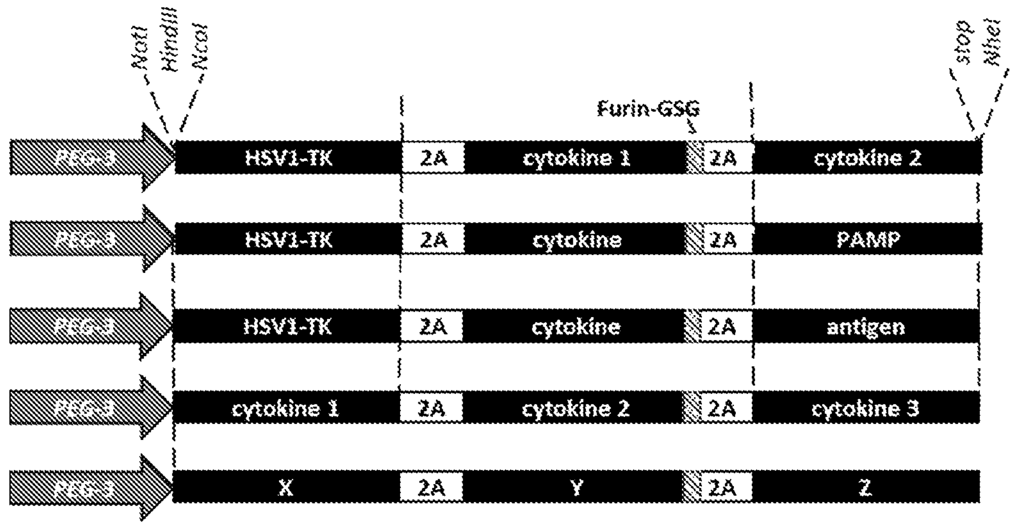
Figure 2A:
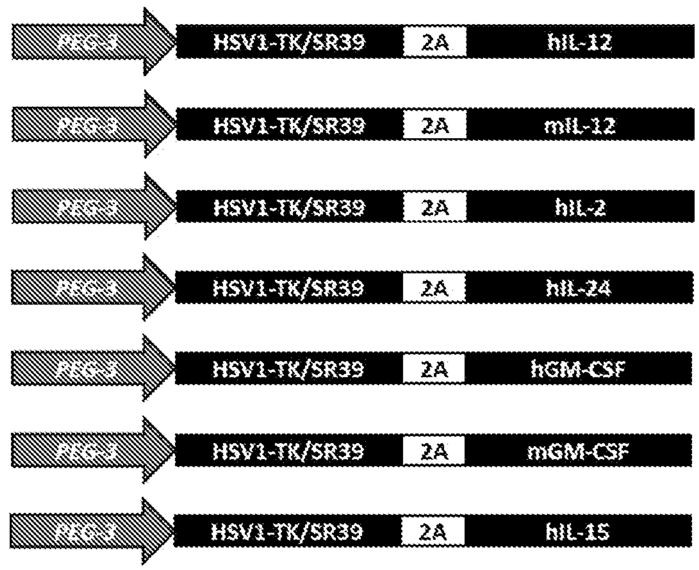
FIGS. 2A-2B show expression of cytokine gene constructs in CpG-free plasmid backbone, formulated into nanoparticles with linear polyethylenimine and expressed in human lung cancer cell line, NCI-H460. The expression cassettes are shown for each PEG-3-TK/SR39-cytokine plasmid construct used in transfections (FIG. 2A).
Figure 2B:
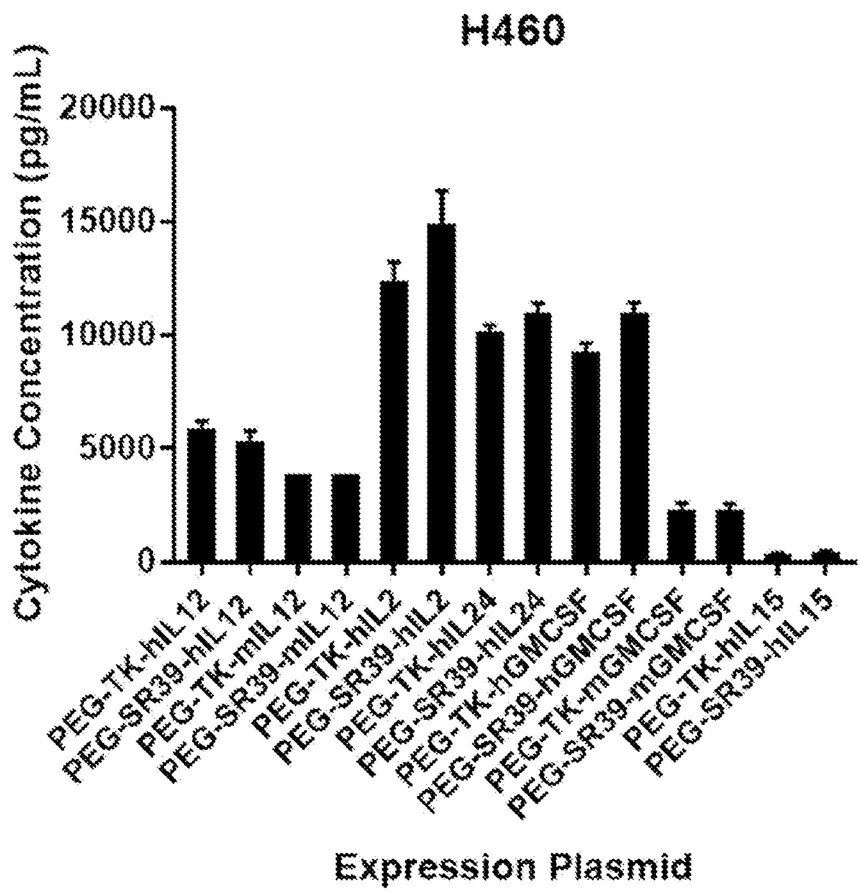
Figure 3A:
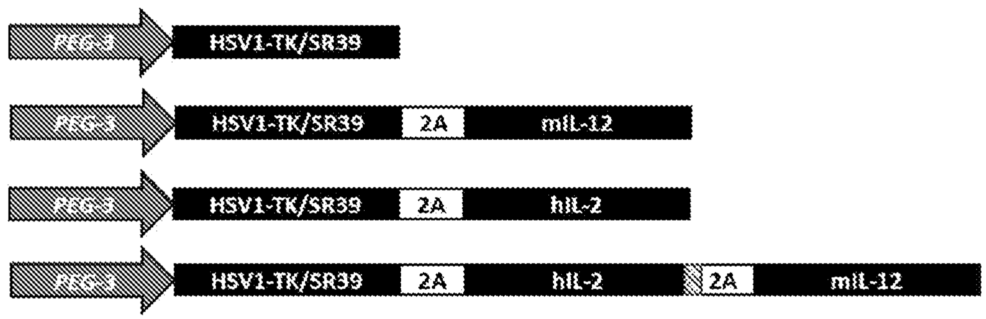
FIGS. 3A-3B show human IL-2 and murine IL-12 expression levels from a cassette containing three payload genes expressed from a single PEG-3 promoter (PEG-TK-hIL2-mIL12) in H460 cells, as determined by ELISA. PEG-TK control (HSV1-TK; no IL2 or IL12) or cassettes containing either PEG-TK-hIL2 or PEG-TK-mIL12 are also shown as controls for the specificity of the antibodies used in the ELISA. Results from the anti-human IL-2 ELISA are shown in the left-hand panel and anti-murine IL-12 ELISA are shown in the panel on the right.
Figure 3B:
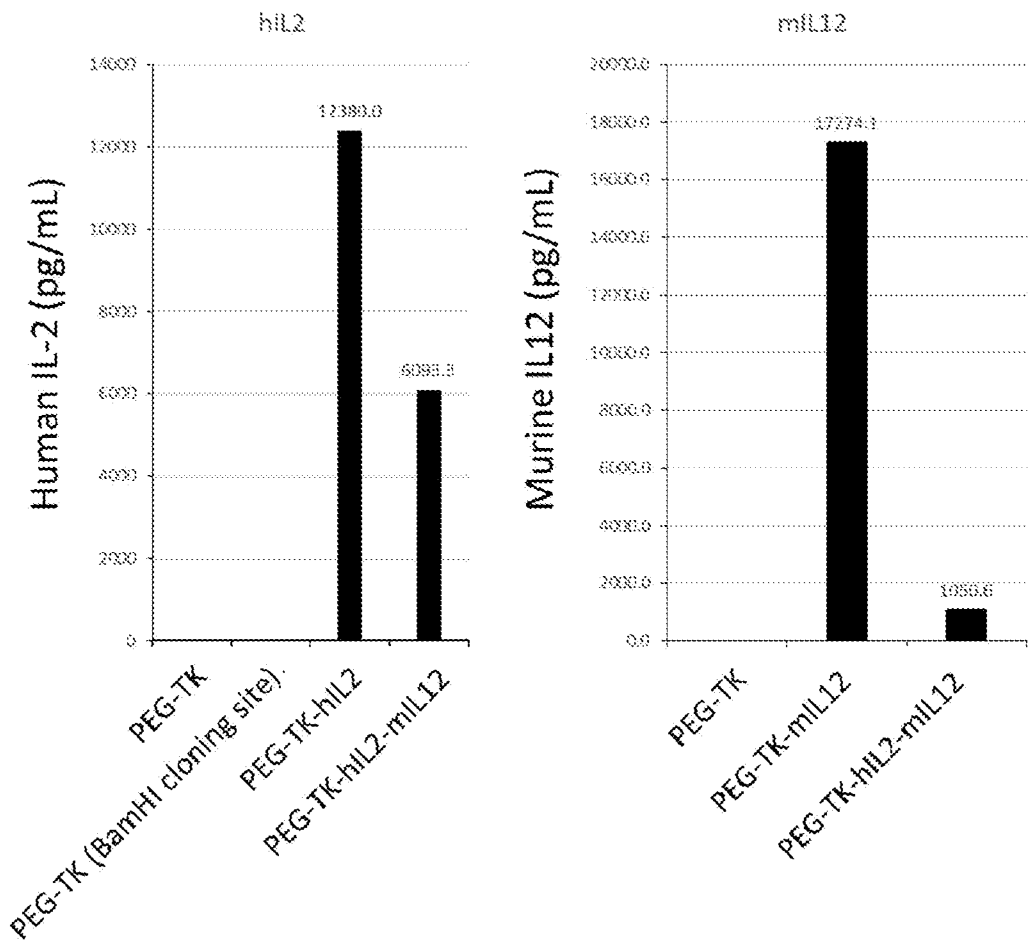
Figure 4A:
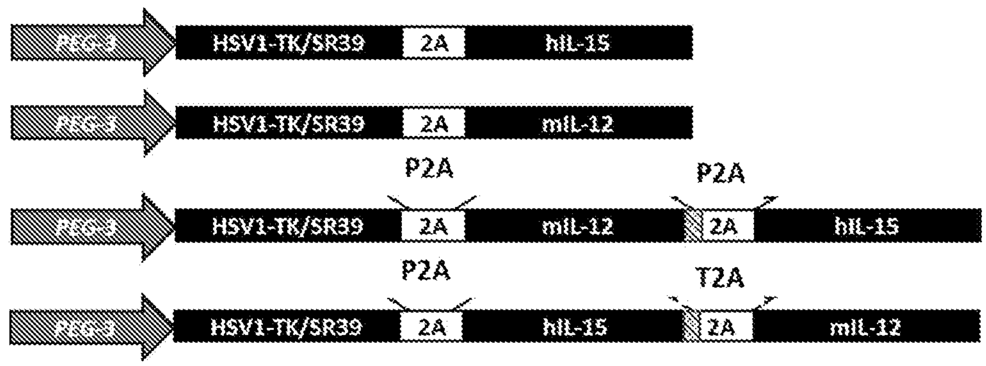
FIGS. 4A-4B show expression levels of murine IL-12 and human IL-15 from a three-gene cassette (PEG-TK-mIL12-hIL15 or PEG-SR39-mIL12-hIL15) cloned into a CpG-free plasmid transfected in H460 cells, as determined by ELISA, FIG. 4B. PEG-TK (PEG-3 HSV1-TK) or PEG-SR39 plasmids are provided as negative controls for each antibody. Cassettes were constructed with two P2A sites (TK-mIL12-hIL15; SR39-mIL12-hIL15) or one P2A and one T2A site (TK-hIL15-mIL12; SR39-hIL15-mIL12). The left-hand panel shows the ELISA data from the anti-murine IL-12 assay, the right-hand panel for the anti-human IL-15 assay.
Figure 4B:
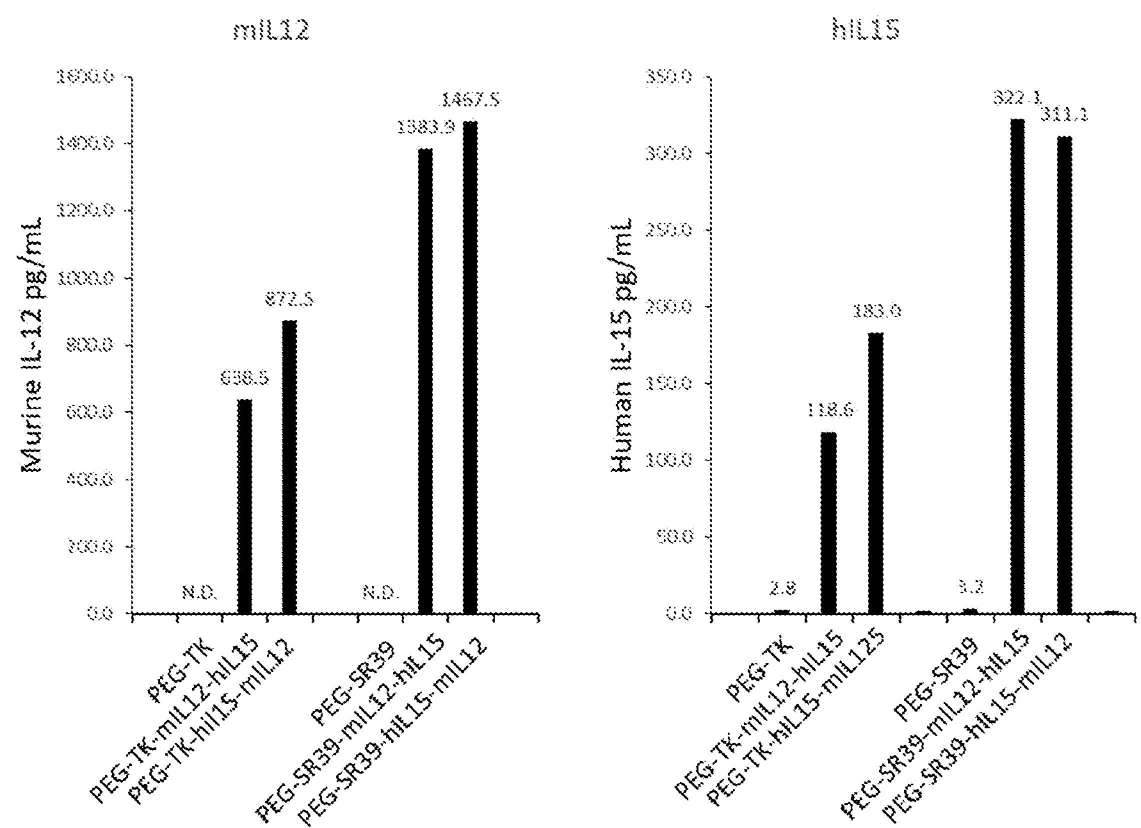

Cytokine sequences: The sequences of human IL-2 (Genbank S77834.1), murine IL-2 (NCBI NM_008366.3); human single chain IL-12 (Human Gene Therapy 1997, 8, 1125-1135), murine single chain IL-12, human IL-15 (Genbank AF031167.1), human MDA 7/IL-24 (NCBI NM_006850.3), human GM-CSF (Genbank M11220.1), murine GM-CSF (GenBank EU366957.1) were analyzed for CpG motifs and rare codons were mutated such that the protein coding sequence was unaffected. These modified sequences were human IL-2 (1 CpG site mutated—SEQ ID NO: 3), murine IL-2 (SEQ ID NO: 4), human single chain IL-12 (30 CpG sites mutated—SEQ ID NO: 5), murine single chain IL-12 (45 CpG sites mutated—SEQ ID NO: 6), human IL-15 containing an IL-2 secretion signal placed upstream of the IL-15 sequence for secretion (3 CpG sites mutated—SEQ ID NO: 7), human MDA 7/IL-24 (9 CpG sites mutated—SEQ ID NO: 8), and human GM-CSF (10 CpG sites mutated—SEQ ID NO: 9), murine GM-CSF (12 CpG sites mutated—SEQ ID NO: 10).

Where the gene ORFs were cloned as a single expression cassette, the gene's coding regions were made with one of the sites NotI, HindIII or NcoI at the 5' end to fit the restriction endonuclease sites of the PEG-3 promoter and a stop codon and NheI site at the 3' terminus for cloning into the plasmid (FIGS. 1A-1B). Where there were two ORFs in the cassette, the first ORF was cloned so that it was made with one of the sites NotI, HindIII or NcoI at the 5' end, a 3' BamHI or a type IIS restriction site such as Esp3I (Esp3I is a type IIS restriction enzyme that cleaves DNA outside of its recognition site and can be used for "scarless" cloning so that no extraneous sequence is introduced) and no stop codon. The second ORF contained a 5' BamHI site or a type IIS restriction site such as Esp3I, followed by a 2A ribosome skipping sequence in frame with the gene sequence, a 3' stop codon and 3' NheI site. Optionally, a furin cleavage site (RRKR) and GSG linker could be placed 5' to the 2A site where post translational removal of the 2A site is required. Where there were 3 genes in a cassette, the first ORF was made with one of the sites NotI, HindIII or NcoI at the 5' end and a 3' BamHI site or type II S restriction site and lacking a stop codon. The second gene contained a 5' BamHI (followed by a 2A sequence) or type IIS site and a 3' Esp3I site (or another appropriate type IIs restriction site) and did not contain a stop codon. The 3' Esp3I site in the second gene was preceded by a furin cleavage site (RRKR) and GSG linker and a 2A ribosome skipping sequence. The third gene was cloned using a 5' Esp3I site, a 3' stop codon and 3' NheI site. Additional genes can be cloned to the construct using type IIS restriction enzymes and expressed as discrete proteins using additional furin cleavage signals, GSG linkers and 2A ribosome skipping sequences in between the genes. The 3'-end of such expression cassettes would encode a stop codon and a NheI site for cloning into the modified pCpG-free-PEG plasmid upstream of the polyA sequence.

PD-1 Fc: The extracellular domain (ECD) of human PD-1 (UniProt Q15116 residues 21-170) was used as a sequence for the design of PD-1-Fc. This sequence was modified to optimize codon usage and remove CpG sites. The PD-1 sequence, to be used in the fusion, encompassed residues 25-170 fused to a signal sequence from human IgG heavy chain 5' to the PD-1 coding region (for secretion from the cells). As an example of cloning, a 5' BamHI restriction endonuclease and a P2A ribosome skipping sequence are placed 5' to the signal sequence. The BamHI site is used for ligation of a first gene containing a 3' BamHI site, for example, to the P2A-signal sequence-PD1ECD cassette following digestion with BamHI of both products, purification and ligation with T4 ligase. In the human PD-1 sequence, Cys 73 is mutated to Ser in order to assist expression and folding (Cheng et al. J. Biol. Chem. 288: 11771-11785, 2013). At the C-terminus of the PD-1 sequence, the Fc sequence (hinge region/CH2/CH3 domains) of IgG4 heavy chain are joined. In this example, human IgG4 is used so that there is reduced binding to Fcγ receptors. Other IgG isotypes can be used such as IgG1 from human or from other species, such as mouse IgG2a. Mutations within the hinge region (at position 228 (serine to proline) and at 235 (leucine to glutamic acid) (EU numbering)) of the heavy chain are introduced to stabilize the hinge and reduced binding to FcγRI, respectively. The IgG4 sequence 216-447 (EU numbering) is followed at the 3' end by a furin cleavage site (RRKR) and GSG linker and T2A ribosome skipping sequence and a Esp3I site to enable "scarless" cloning of the third protein onto the P2A-signal sequence-PD1ECD-Fc-FurinGCGT2A fragment (50 CpG sites removed—SEQ ID NO: 11).

The known TLR5 stimulatory epitopes of flagellin (FliC) from *Salmonella typhimurium* (Genbank D13689.1) (76 CpG sites removed—SEQ ID NO: 12) were synthesized as codon optimized and CpG-free sequences. The primary sequences of these regions were not altered to remove the potential glycosylation sites, although this may be a consideration as native FliC is not glycosylated. Flagellin DNA sequence encoding amino acids 1-191 and 336-495 were synthesized (although full-length protein can be used) with a 5' Esp3I site and a 3' stop codon and NheI site for cloning downstream of a first and second gene.

Monoclonal, bispecific or fragments of antibodies can be expressed alone or within a construct expressing murine or human IL-12, for example they can be cloned downstream of the IL-12 sequence, a furin cleavage site a BamHI cloning site and a 2A ribosomal skipping sequence. CpG-free constructs were designed through reverse translation of the peptide sequence using a codon optimized CpG-free human biased genetic code matrix. The expression cassette is exemplified for monoclonal antibodies in an expression cassette with IL-12 such as hIL12-ipilimumab (Drug Bank DB06186) (SEQ ID NO: 13), hIL12-pembrolizumab (Drug Bank DB09037) (SEQ ID NO: 14), hIL12-nivolumab (Drug Bank DB09035) (SEQ ID NO: 15), hIL12-bevacizumab (Drug Bank DB00112) (SEQ ID NO: 16), hIL12-durvalumab (Drug Bank DB11714) (SEQ ID NO: 21), hIL12-atezolizumab (Drug Bank DB11595) (SEQ ID NO: 22). This is also exemplified for a bispecific blinatumomab, hIL12-blinatumomab (Drug Bank DB09052) (SEQ ID NO: 17) and Fab ranibizumab (Drug Bank DB01270) (hIL12-ranibizumab, SEQ ID NO: 18) and anti-murine PD-1 monoclonal, iTME (WO2016/170039) (mIL12-iTME SEQ ID NO: 19).

Example 2: In Vitro Expression Analysis

Constructs were transfected into cultured cancer cells, such as human lung cancer cell lines H460 (ATCC® HTB-177™) or H1975 (ATCC® CRL-5908™) or murine lung cancer cell line LL/2 (Perkin Elmer, Watham, MA), and tested for expression of the individual proteins by ELISA. Plasmids were formulated with jetPRIME (Polyplus Transfection, Illkirch, FRANCE) according to the manufacturer's instructions. For example, LL/2 cells were plated at a density of 10e5 cells/well in a 12 well plate in DMEM. 1 μg of plasmid was diluted into 25 μL of serum free media and vortexed gently. 4 μL PEIpro was added into 25 μL of serum free media and the PEIpro solution was added to the DNA solution and vortexed gently, followed by 15 min incubation at room temperature. The cells were incubated at 37° C. in 5% $CO_2$ for 48 hours. Culture supernatant was then removed and stored at −20° C. until testing by ELISA using the relevant anti-cytokine Quantikine ELISA kit (R & D Systems, Minnesota, USA) according to the manufacturer's instructions. Dilutions of the culture supernatants were made in duplicate and quantitation of cytokine expression was measured against standard curves of known standards (FIGS. 2A-2B, 3A-3B, 4A-4B).

Figure 5:
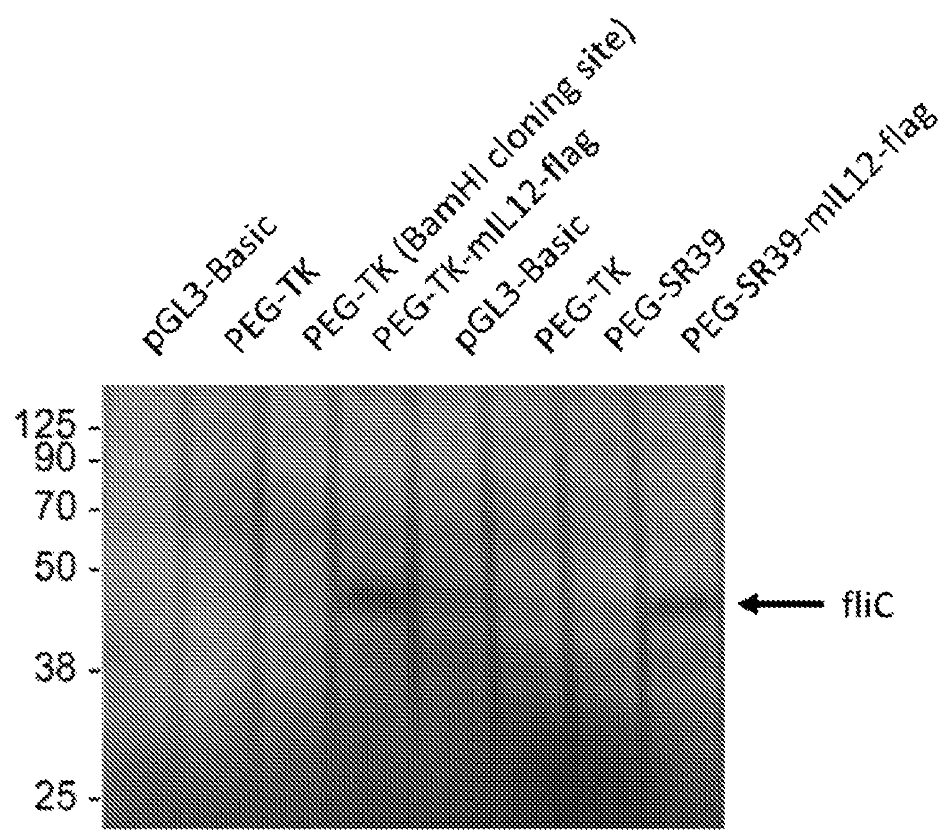
FIG. 5 shows the expression of FliC domains from a cassette containing murine IL-12 and flagellin domains, as determined by Western blot using anti-FliC antibody. The expression of FliC can be seen as a obvious band in lanes PEG-TK-mIL12-flag and PEG-SR39-mIL12-flag. The predicted unglycosylated molecular weight is 39.5 kDa. Non-expressing empty plasmid pGL3 or constructs containing PEG-3 HSV1-TK (PEG-TK or PEG-TK with a 3' BamHI cloning site) or PEG-SR39 are shown as negative controls.

FliC expression was monitored by Western blot analysis in the following manner. Cells were lysed by adding T-per® Tissue Protein Extraction Reagent (#78510, Thermo Fisher, Waltham, MA, USA) and incubating in ice for 15 min. After clarifying by centrifugation, the total amount of protein was determined by Coomassie (Bradford) Protein assay. A total of 30 μg of cell extract (per well) were loaded on to SDS-PAGE gel. After electrophoresis, proteins were transferred to a polyvinylidenefluoride membrane (Bio-Rad) using a Trans-Blot® TURBO transfer (Bio-Rad). The membrane was blocked with 5% BSA in TBS-T (10 mM Tris-Cl pH 8.0, 150 mM NaCl, 0.01% Tween-20) for 1 hour at room temperature and incubated overnight with 1:1000 dilution of anti-FliC primary antibody (#629701, BioLegend, San Diego, CA, USA) at 4° C. in the same buffer. After washing the membrane four times with TBS-T for 10 minutes, the membrane was incubated with goat anti-mouse HRP secondary antibody (#31430, Thermo Fisher, Waltham, MA, USA) diluted 1:10,000 in 5% BSA TBS-T for 1 h at room temperature followed by four washes with TBS-T for 10 minutes. The membrane was visualized by Clarity™ Western ECL kit (BIO-RAD) and ChemiDoc™ XRS+ imaging system (BIO-RAD) (FIG. 5).

Figure 6A:
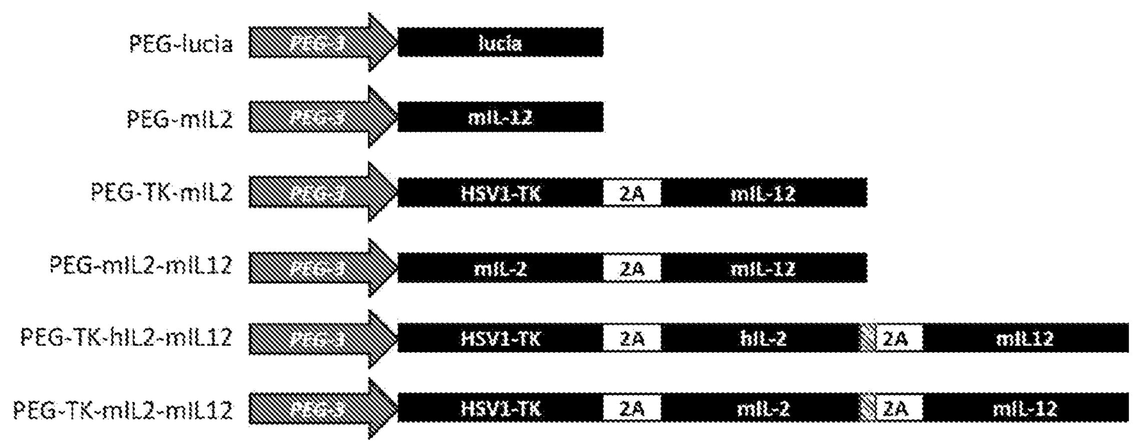
FIGS. 6A-6D. Plasmid expression cassettes that were ligated into a CpG-free plasmid backbone and formulated into nanoparticles are shown in FIG. 6A. The biological activity of the formulated nanoparticles was tested in in vitro assays.
Figure 6B:
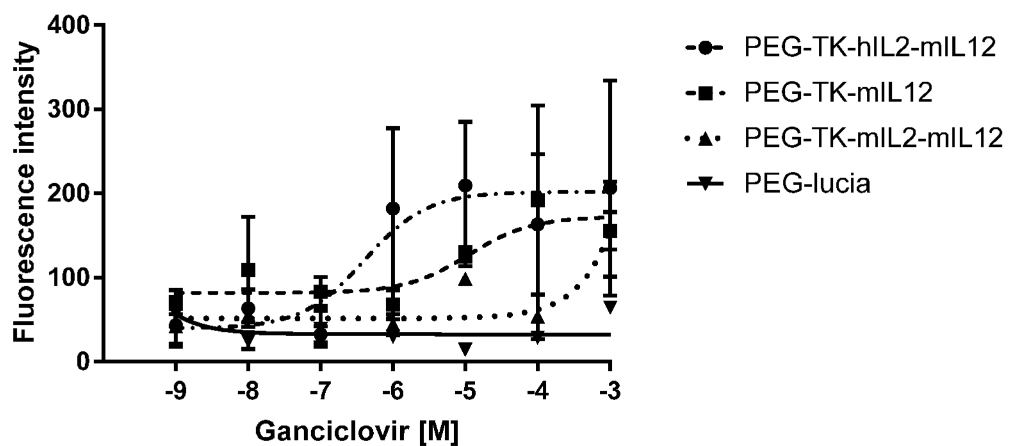

Example 3: Thymidine Kinase Activity 1.5 μg of PEG-TK-hIL2-mIL12, PEG-TK-mIL12, PEG-mIL12 or PEG-lucia plasmid (FIG. 6A) were diluted in 75 μL of pre-warmed OptiMEM medium and gently vortexed. 12 μL of PEIpro reagent was diluted into 75 μL of OptiMEM. The PEIpro solution was then added to the DNA solution and vortexed gently. The DNA/PEIpro solution was incubated for 15 min at room temperature. 2.5 μL of the DNA/PEIpro solution was added to the 96-well plate. LL/2-Red-FLuc cells (Perkin Elmer, Waltham, MA) were cultured in a T175 flask until 60-70% confluent. The cell monolayer was briefly washed with 20 mL PBS, trypsinized with 3 mL of trypsin/EDTA for 3 min and 7 mL of media was added once the cells were removed from the surface. The suspension was transferred to a 15 mL Falcon tube and centrifuged at 200 g for 5 min. The supernatant was removed and the cell pellet was resuspended in 3 mL of fresh media. Cells were plated at 1,000 or 5,000 (assay dependent) cells/well in a 96-well plate in 100 μL per well of complete DMEM media. Plates were transferred to a 37° C./5% $CO_2$ incubator and allowed to grow for 24 hours prior to compound treatment. A 100 mM stock was prepared in DMSO and used to prepare a 10-fold dilution series from 1000 mM to 0.01 μM in DMSO. The media containing transfection reagent were removed from the transfection plate and replaced with 50 μL/well of respective ganciclovir concentration (triplicate wells for each concentration). The plate was incubated for 48 hours at 37° C. CellTox™ Green Cytotoxicity reagent (Promega, Madison, WI) was made up to 2× with assay buffer and 50 μL of reagent was added to each well of the 96-well plate with the cells incubated with ganciclovir. The plate was incubated for 15 min at room temperature, protected from light and the green fluorescence was read at 485 nm (excitation) and 520 nm (emission). When the cells were treated with escalating doses of ganciclovir, there was a clear increase in fluorescence intensity (which directly correlates to cytotoxicity of the cells) in the particles formulated with PEG-TK-hIL2-mIL12, PEG-TK-mIL2-mIL12, and PEG-TK-mIL12 that expressed HSV1-TK, but not in nanoparticles formulated with PEG-lucia plasmid that did not express HSV1-TK (FIG. 6B).

Example 4: Functional Analysis of Expressed IL-2 and mIL-12 In Vitro

The CTLL-2 cell line (ECACC 93042610) is a cytotoxic T cell line of mouse origin derived from C57BL/6 inbred mice (H-2b) and is dependent upon stimulation from IL-2 for survival and growth. In this assay, proliferation was induced by IL-2 expressed in the culture media of a LL/2 cell line transfected with nanoparticles containing engineered plasmids of the PEG-3 promoter and expressing murine IL-2 or human IL-2 in a cassette with mIL-12 (mIL2-mIL12:). Both human and murine IL-2 can act on CTLL2 cells and mIL-12 has also been shown to have a proliferative effect in the presence of IL-2. As a positive control, lyophilised recombinant hIL-2 (rhIL-2) was reconstituted to 100 μg/mL in 100 mM sterile acetic acid containing 0.1% BSA. Stock rhIL-2 was diluted down to 500 ng/mL in RPMI 1640 without T-Stim, which was used to prepare a 2-fold dilution series from 20 ng/mL to 0.163 ng/mL in a 96-well intermediate plate in a final volume of 100 μL/well. 50 μL of each dilution was transferred into the final cell proliferation plate. A 2-fold dilution series from 1:2 to 1:32 for cell culture supernatants was prepared in RPMI 1640 without T-Stim (125 μL:125 μL media). 50 μL of each dilution was transferred into the final cell proliferation plate.

Figure 6C:
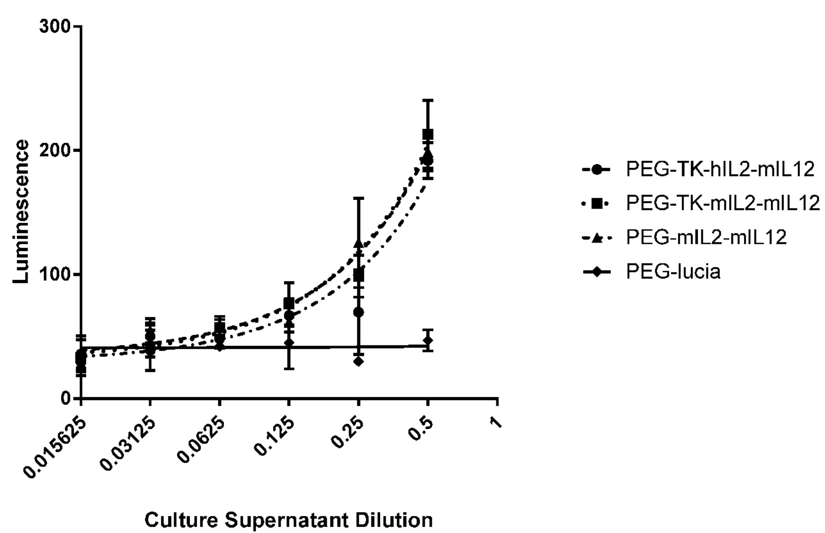

CTLL2 cells that had been maintained at 2×10e5 cells/mL in complete RPMI media (containing T-Stim) were collected and centrifuged at 400 g for 5 min. Cells were resuspended in 20 mL RPMI media containing all additional supplements except T-Stim and cultured for a further 24 hours at 37° C. in 5% $CO_2$. Cells were then plated at 4×10e4 cells/well in a 96-well plate in 50 μL of RPMI media without T-Stim on the final cell proliferation plate. In order to assay proliferation, 100 μL of CellTiter-Glo® Reagent (Luminescent Cell Viability Assay, Promega Corp., Madison, WI) was added to the cells in line with the manufacturer's guidelines for the CellTiter-Glo® Reagent. Cells were incubated at room temperature (with shaking at 500 rpm) for 15 minutes and the luminescence was recorded on a luminometer and quantified using a standard curve as per manufacturer's instructions. The results show that undiluted culture supernatant in LL/2 cell transfected with PEG-mIL2-mIL12 (SEQ ID NO: 20), PEG-TK-mIL2-mIL12, and PEG-TK-hIL2-mIL12 nanoparticles caused proliferation of CTLL2 cells, which demonstrates expression of active IL-2 and mIL-12. (FIG. 6C).

Example 5: Functional Analysis of Expressed IL-12 In Vitro

Peripheral blood mononuclear cells (PBMCs) were isolated from whole blood samples by Ficoll Hypaque gradient centrifugation. 10e7 PBMCs were added to a total of 20 mL supplemented medium in a 75 $cm^2$ culture flask. 20 μL of 10 mg/mL phytohemagglutinin (PHA) (200 μg PHA) was added and the flask was incubated for 3 days at 37° C. in 5% $CO_2$. 20 mL of supplemented media was added and then gently mixed by shaking. 20 mL of the contents were then transferred to a clean 75 $cm^2$ culture flask and human recombinant IL-2 was added to 50 U/mL and further incubated for 24 hours at 37° C. in 5% $CO_2$. PBMCs were diluted to 2×10e5 cells/mL for use in the assay.

Figure 6D:
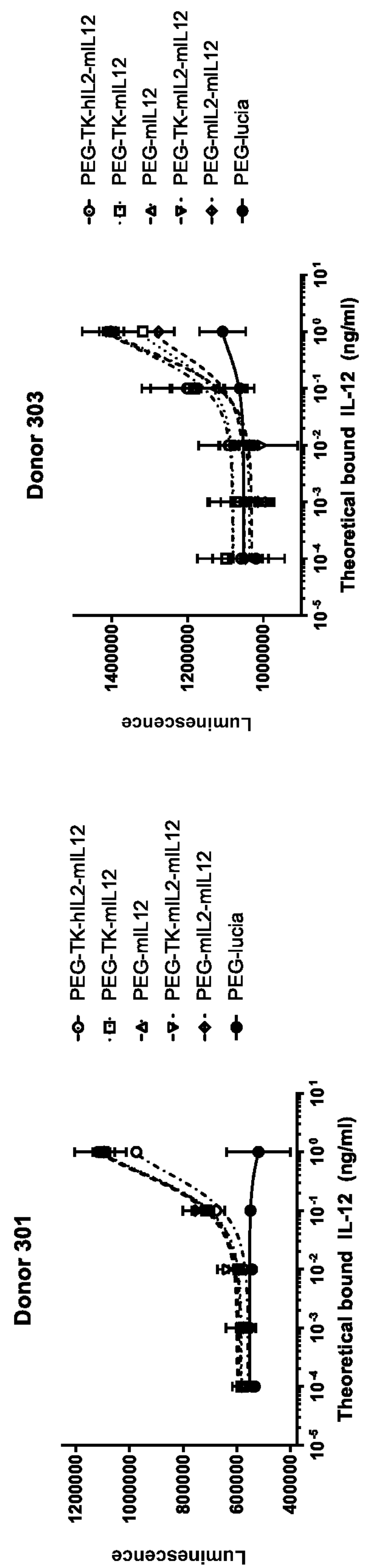

A 96-well plate was coated with 5 μg/mL mouse anti-IL-12 antibody in $NaCO_3$ or PBS buffer and incubated at 4° C. overnight. Plates were washed with buffer and then blocked with 1% BSA/PBS for 1 hour at room temperature. Serial dilutions of mIL-12 reference compound (5 ng/mL to 0.008 ng/mL) and cell supernatant (containing expressed mIL-12) were made and 100 μL of reference or test sample dilutions were added to the wells, followed by incubation for 2.5 to 3 hours at room temperature. The plate was washed with PBS buffer and 100 μL PHA stimulated PBMC cells were added (2×10e4 cells/well). The cells were incubated for 7 days at 37° C. in 5% $CO_2$. Cell proliferation was detected using CellTiter-Glo® Reagent according to the manufacturer's instructions. Cell culture supernatants from LL/2 cells that were transfected with nanoparticles expressing mIL-12 showed a proliferative response from PBMCs isolated from two human donors (FIG. 6D).

Example 6: Activity of PEG-3 Plasmid Formulated Nanoparticles in a Syngeneic In Vivo Model of Mouse Primary Lung Cancer (Orthotopic LL/2 in C57BL/6 Mice)

Tumor Cell Culture and Inoculation—

LL/2-Red-FLuc mouse lung tumor cells (Perkin Elmer, Waltham, MA, USA) were cultured in MEM supplemented with 10% FBS, 1% GlutaMAX™ and 1% penicillin-streptomycin, and grown at 37° C. in a humidified cell culture incubator supplied with 5% $CO_2$ (materials supplied by Invitrogen, Carlsbad, CA, USA). The cells were harvested (Passage 2) by trypsinization, washed twice in HBSS and counted (using trypan blue exclusion). The final cell density was adjusted with HBSS:Matrigel™ (BD Biosciences, East Rutherford, NJ, USA) (1:1, v/v) to 2×10e6 cells/mL. Female C57BL/6 (Envigo, Indianapolis, IN, USA) mice were inoculated while under intraperitoneally injected anesthesia (Ketamine (14 mg/mL)/Xylazine (1.2 mg/mL)) (Clipper Distributing Company, St Joseph, MO, USA). The skin at the injection site was liberally swabbed with alcohol and 20 μL aliquot of cell suspension containing 4×10e4 LL/2-Red-FLuc cells were injected into the pleura. Mice were administered a 200 μL bolus dose of Buprenex (Buprenorphine HCl, 0.01 mg/mL) (Hospira, Inc, Lake Forest, IL, USA) subcutaneously for pain relief at the time of surgery and the following day. The presence of lung tumors was confirmed based on a positive luminescence signal in the thoracic region of whole at Study Day 5. Animals (with positive luminescent signal) were randomized using a matched pair distribution method, based on body weight, into groups of 10, five days post-inoculation (Study Day 5). Procedures involving the care and use of animals in the study were reviewed and approved by the Pennsylvania State College of Medicine Institutional Animal Care and Use Committee prior to conduct. During the study, the care and use of animals was conducted in accordance with the principles outlined in the Guide for the Care and Use of Laboratory Animals, 8th Edition, 2011 (National Research Council).

Monitoring—

Mortality and checks for clinical signs were performed once daily in the morning during the study. Body weights were recorded for all animals on Study Day 5 and then at least twice weekly, including the termination day. Whole body imaging was performed at inoculation (Study Day 0) and then all remaining animals on Study Days 5, 9, 13 and at termination.

Formulation of Nanoparticles for In Vivo Use.

Nanoparticles comprising of the plasmid and a linear PEI polymer (in vivo-jetPEI®, Polyplus Transfection, Illkirch, France) were prepared under high pressure using a confined impinged jet (CIJ) device. In this device, the streams are impinged in the confined chamber at high Reynolds number, thereby causing the water-soluble polycationic polymers and the water-soluble polyanionic nucleic acid to undergo a polyelectrolyte complexation process that continuously generates nanoparticles. The CIJ device and all the fittings were autoclaved on a dry cycle prior to use. A working solution of in vivo-jetPEI® was made in 9.5% Trehalose and combined under pressure with a stock solution of plasmid in 9.5% Trehalose (according to Patent Application US 2017/0042829). PEG-3 plasmids containing CpG-free genes for mIL-12, TK-hIL2-mIL12 (PEG-mIL-12, PEG-TK-hIL12-mIL12, respectively) or lucia luciferase (Invivogen, San Diego, CA, USA) (PEG-lucia) were formulated at a N/P=6 ratio followed by lyophilization in 0.05 mg (DNA) aliquots. 0.05 mg (DNA content) of each formulated plasmid, PEG-TK-hIL2-mIL12, plasmid PEG-mIL12 or PEG-lucia control, was reconstituted in 250 μL of nuclease-free water on the day of dosing. Formulated test articles were stored at 4° C. until use on the same day. 9.5% Trehalose buffer was used as a vehicle control. 0.04 mg of each plasmid formulation were administered via intravenous injection (i.v.) in a fixed volume of 200 μL/animal on Study Days 5, 9, 13, 17, and 21.

Imaging—

In vivo whole-body luminescence imaging was performed on all animals at inoculation (Study Day 0) and then on all remaining animals on Study Days 5, 9, 13, and at termination using the Perkin Elmer IVIS.Lumina XR imaging system. Animals were administered 150 mg/kg D-luciferin (15 mg/mL solution prepared in PBS) via intraperitoneal injection and were imaged 5-10 minutes later while under isoflurane anesthesia. Animals were allowed to recover from anesthesia prior to dosing. Luminescence signal was measured in the region of interest (thoracic region) and images were captured. Images were analyzed using Living Image 4.4 (Caliper Life Sciences, Hopkinton, MA, USA).

Termination Procedure—

All animals were anesthetized for blood collection and euthanized by exsanguination via terminal cardiac bleed by approved standard procedures. The study was terminated on Study Day 23 as the majority of animals had reached the ethical end-point of body weight loss or adverse clinical observations or had died from unknown causes.

Results—

Figure 7:
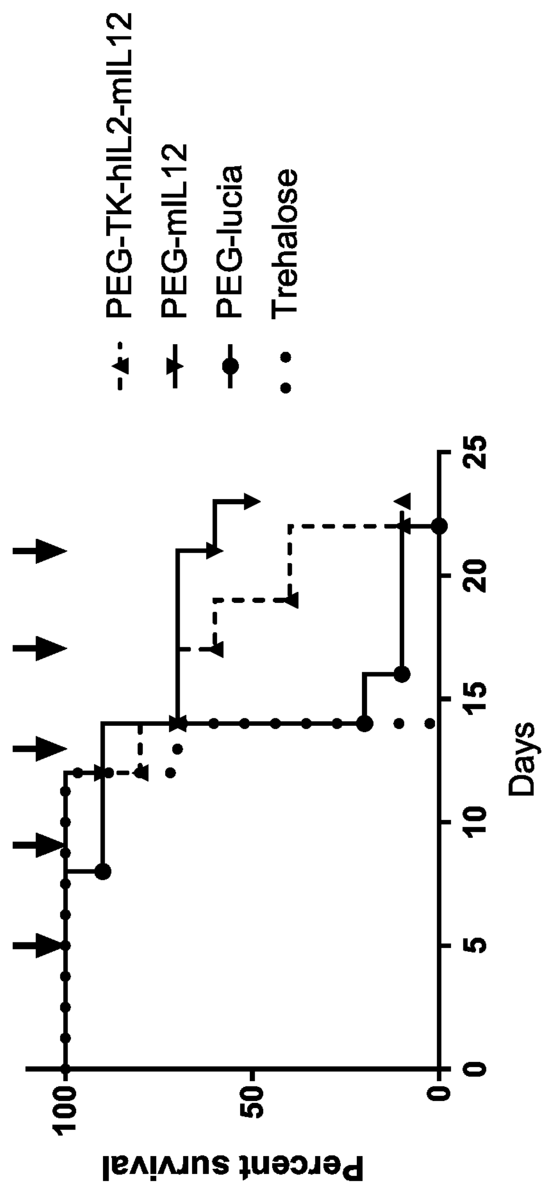
FIG. 7 shows a Kaplan Meier survival plot of anti-tumor activity of the nanoparticles containing the indicated PEG-3 plasmids in C57BL/6 mice inoculated with an orthotopic LL/2 Red-FLuc model of lung cancer. Mice were dosed at 4-day intervals, beginning at day 5 (post tumor cell inoculation), as indicated by the arrows above the chart. The study was terminated on Day 23. Both PEG-TK-hIL2-mIL12 and PEG-mIL12 significantly (Log rank test, $p \leq 0.001$) extended survival in this model compared to the vehicle control (Trehalose) and PEG-lucia.
Figure 8:
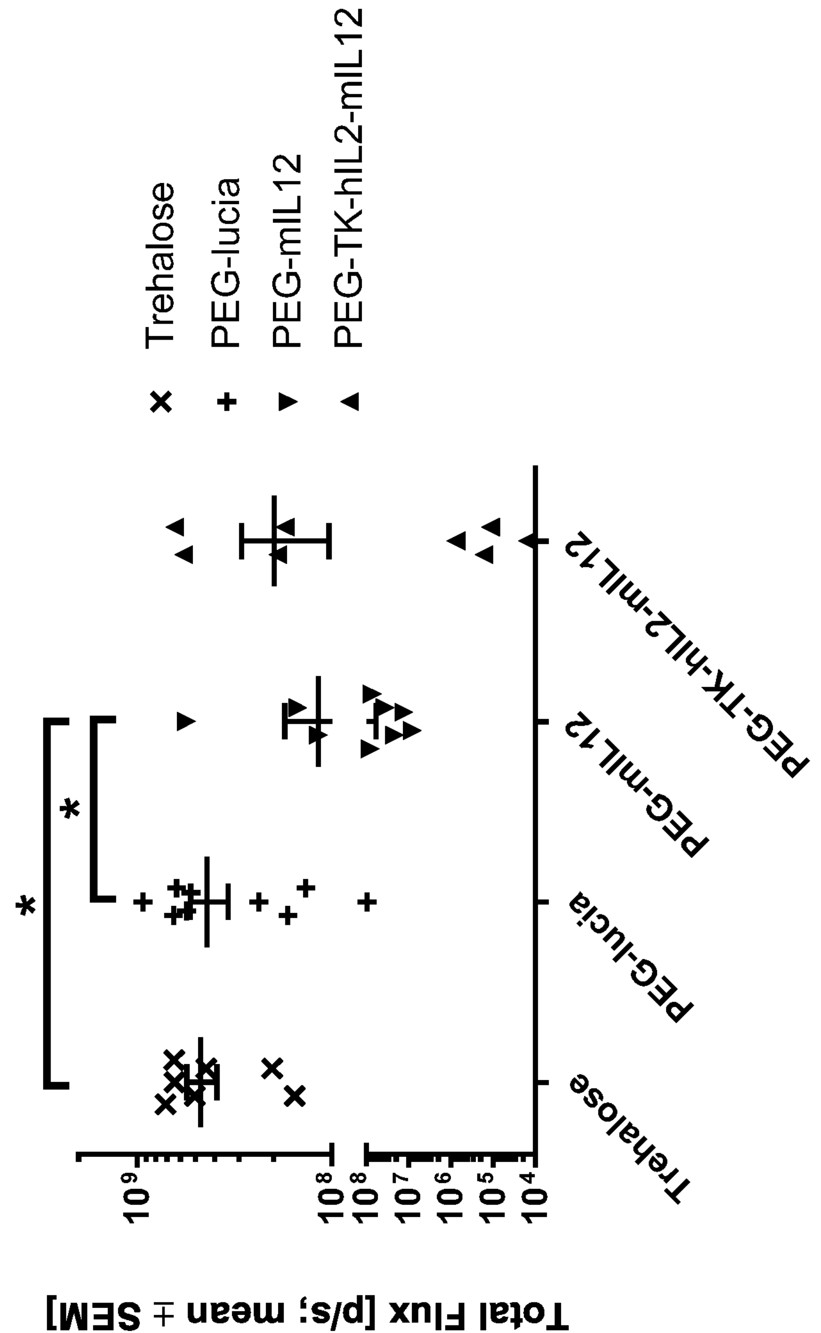
FIG. 8. Anti-tumor activity of PEG-3 nanoparticles used in the study shown in FIG. 7 was assessed through comparison of the mean in vivo luminescence signal±SEM (Total Flux (p/s)) in the lungs of mice at day 13 after implantation of LL/2 Red-FLuc cells orthotopically into the lungs of C57BL/6 mice. The luminescence signal is indicative of tumor cell growth. There was a significant reduction in signal (Dunnett's multiple comparisons test, $p \leq 0.05$) in the PEG-mIL12 group compared to the Trehalose vehicle control group and the PEG-Lucia nanoparticle control, indicating significant inhibition of tumor growth.

The study was terminated at Day 23 when only six animals remained alive, one treated with plasmid PEG-TK-hIL2-mIL12 and five treated with plasmid PEG-mIL12. Survival time was significantly ($p \leq 0.05$) prolonged in animals receiving plasmid PEG-TK-hIL2-mIL12 and PEG-mIL12 compared with vehicle control (9.5% Trehalose), as shown by Kaplan Meier Analysis (FIG. 7). Median survival times were 19 days for PEG-TK-hIL2-mIL12, 23 days for PEG-mIL12 and 14 days for PEG-lucia and the Trehalose groups. Luminescence in vivo imaging on Study Day 13 (after two doses had been administered) showed plasmid PEG-mIL12 to significantly reduce ($p \leq 0.05$; Dunnett's Multiple Comparisons Test) the growth of the lung tumors, as indicated by reduced luminescence in the lung region (corresponding to less LL/2-Red-FLuc tumor cells), compared with 9.5% Trehalose control (FIG. 8).

Therefore, two formulations of nanoparticles made in the CIJ device at N/P=6, the single payload cassette (mIL-12) and the three payload cassette (TK-IL2-IL12), improved survival of mice that had been orthotopically inoculated with tumors in the lungs (FIG. 7). In addition, PEG mIL-12 nanoparticles showed a significant reduction in the luminescence of the tumor cells in vivo at Day 13 post inoculation, which is indicative of reduced tumor growth in the lungs (FIG. 8). Accordingly, these results demonstrate that the formulations of the present technology are useful in methods for treating cancer in a subject in need thereof.

Example 7: Syngeneic Model of Mouse Primary Lung Cancer LL/2

In a second experiment, animals in each group received treatment with either 9.5% Trehalose Control (in a fixed volume of 200 µL/animal) or one of the plasmid-in vivo-jetPEI® formulations (N/P=6) (plasmid PEG-mIL12, plasmid PEG-TK-mGMCSF, plasmid PEG-TK-hIL15-mIL12, plasmid PEG-TK-mIL12-flag and PEG-lucia) each at 2 mg/kg in a dosing volume of 10 mL/kg. All treatments were administered via intravenous injection (i.v.) on Study Days 5, 9, 13, 17, and 21. Methods were as described in Example 6 above for animal treatment and imaging.

Results—

Figure 9:
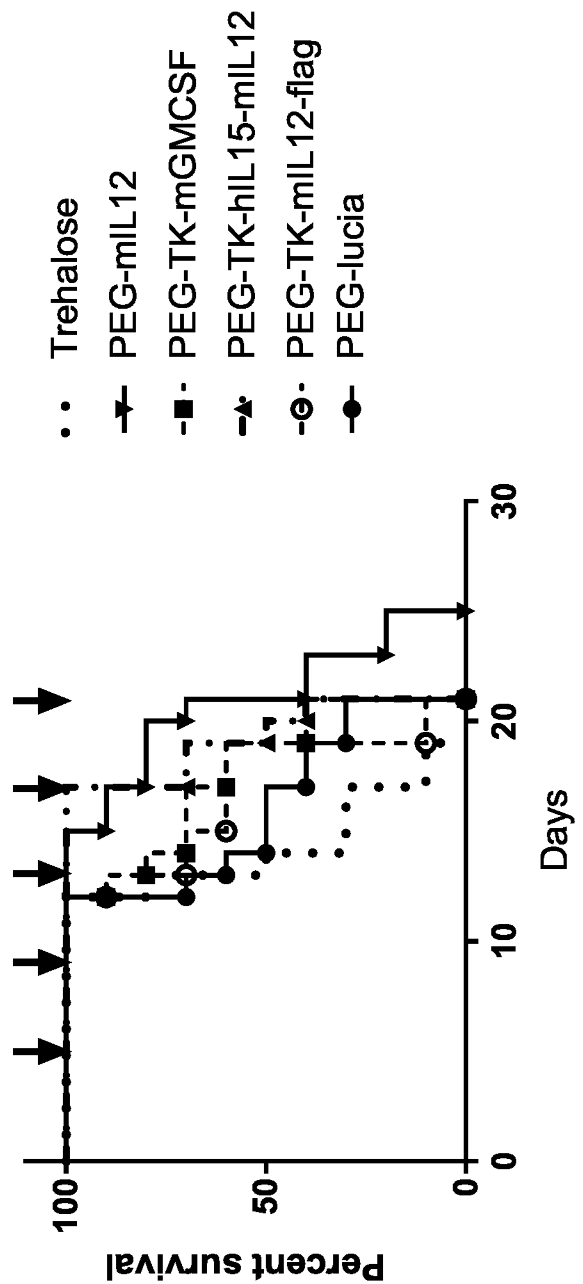
FIG. 9 shows a Kaplan Meier survival plot of anti-tumor activity in vivo of the nanoparticles containing the indicated PEG-3 plasmids in an orthotopic LL/2 Red-Fluc model of lung cancer in mice. Days at which nanoparticles were dosed post tumor cell inoculation are indicated by the arrows above the plot. Nanoparticles PEG-mIL12, PEG-TK-mGMCSF, PEG-TK-hIL15-mIL12 and PEG-TK-IL12-flag, but not PEG-lucia, significantly ($p \leq 0.05$, Log rank test) improved survival of the mice compared to the 9.5% Trehalose vehicle control.

Kaplan Meier survival analysis is shown in FIG. 9. Median survival times for animals treated with nanoparticles PEG-mIL12 (21.0 days), PEG-TK-mGMCSF (19.0 days), PEG-TK-hIL15-mIL12 (19.5 days) and PEG-TK-mIL12-flag (19.0 days) were significantly ($p \leq 0.05$) longer than 9.5% Trehalose Control (13.5 days). There was no significant difference in median survival for animals treated with PEG-lucia control (15.5 days) and 9.5% Trehalose Control. Therefore, formulations of active nanoparticles at N/P=6 were effective at prolonging survival in LL/2 mice. Accordingly, these results demonstrate that the formulations of the present technology are useful in methods for treating cancer in a subject in need thereof.

Example 8: Syngeneic Model of Experimental Metastasis to the Lung Using B16F10-Red-FLuc Cells Tumor Cell Culture and Inoculation—

B16F10-Red-FLuc mouse melanoma cells (Perkin Elmer, Waltham, MA, USA) were cultured in RPMI 1640 cell culture medium supplemented with 10% FBS, 1% GlutaMAX™, and 1% penicillin-streptomycin, and grown at 37° C. in a humidified cell culture incubator supplied with 5% $CO_2$. The cells were harvested by trypsinization, washed twice in HBSS and counted (using trypan blue exclusion). The final cell density was adjusted with HBSS to 3.5×10e6 cells/mL. 100 µL of cell suspension, consisting of 3.5×10e5 cells, was discharged into the tail vein of mice at the start of the study (Day 0). Imaging was performed on study Day 5, when the presence of lung tumors was confirmed in sufficient animals to commence the study. Imaging was performed as described in Example 6.

9.5% Trehalose buffer and nanoparticles containing PEG-lucia, PEG-mIL12, PEG-TK-mIL12, PEG-mIL2-mIL12 and PEG-TK-mIL2-mIL12 (each 60 µg/vial) were reconstituted in 300 µL of nuclease-free water per vial on the day of dosing to give dosing solutions of 200 µg/mL. Formulated test articles were stored at 4° C. and used on day of reconstitution.

9.5% Trehalose buffer and nanoparticles containing PEG-lucia, PEG-mIL12, PEG-TK-mIL12, PEG-mIL2-mIL12 and PEG-TK-mIL2-mIL12 were administered via intravenous injection (i.v.) on Study Days 5, 8, 11, 14 and 17. Treatments were administered at a dose of 2 mg/kg in a dosing volume of 10 mL/kg on Study Days 5, 11, 14 and 17. Due to declining body weight in all groups apart from the vehicle control at Day 6, the dose was reduced to 1 mg/kg in 5 mL/kg for the dose administered on Study Day 8. Dosing then resumed at 2 mg/kg in 10 mL/kg on Study Day 11 as per protocol.

Results—

Figure 10:
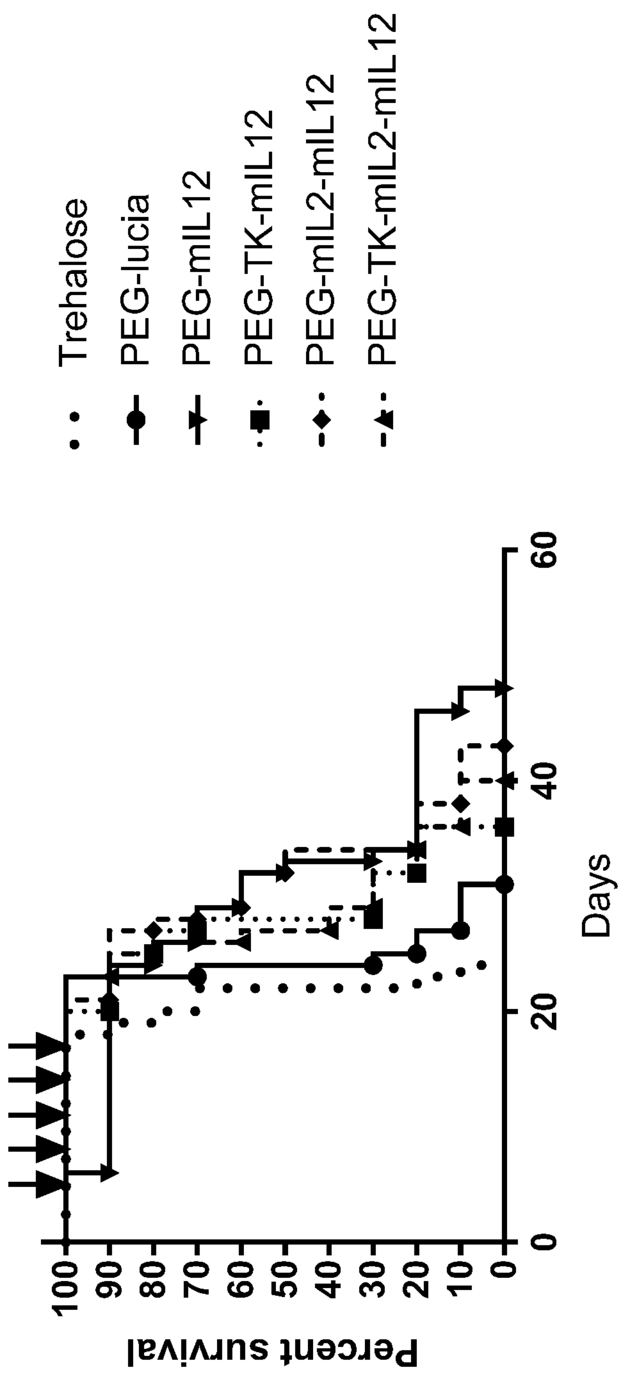
FIG. 10 shows a Kaplan Meier survival plot of anti-tumor activity in vivo of nanoparticles containing the indicated PEG-3 plasmids in a B16F10-Red-FLuc experimental model of metastatic lung cancer. Nanoparticles were dosed at 3-day intervals, beginning at day 5 (post tumor cell inoculation) as indicated by the arrows above the plot. Nanoparticle formulations PEG-mIL12, PEG-TK-mIL12, PEG-mIL2-mIL12, PEG-TK-mIL2-mIL12 significantly extended survival ($p \leq 0.05$, Log rank test) of the mice compared to vehicle control and PEG-lucia. PEG-lucia also significantly extended survival in this study compared to the vehicle control.
Figure 11:
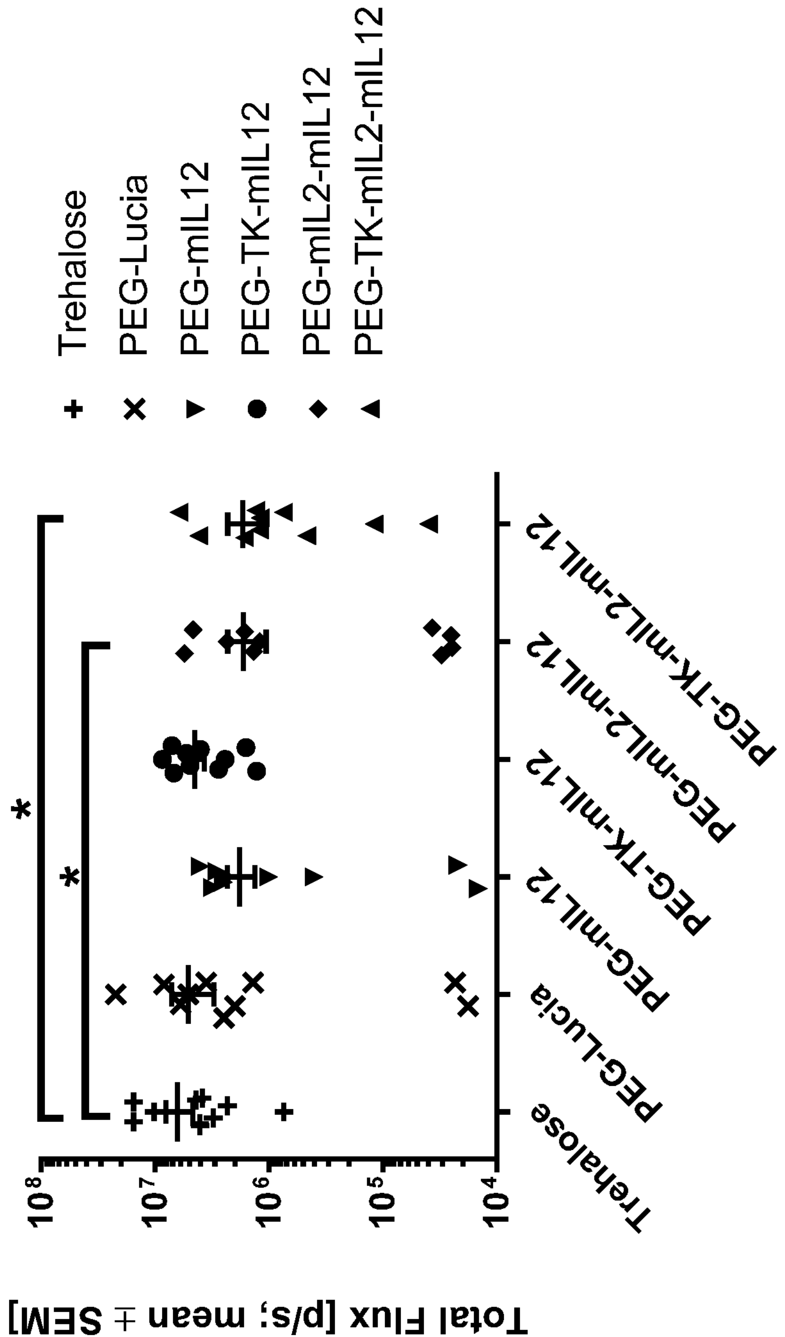
FIG. 11. Anti-tumor activity of PEG-3 nanoparticles used in the experimental metastasis study (shown in FIG. 10) were assessed through comparison of the mean in vivo luminescence signal±SEM (Total Flux (p/s)) in the lungs of C57BL/6 mice 12 days after inoculation of B16F10-Red-FLuc cells. The luminescent signal is indicative of the growth of tumor cells expressing firefly luciferase. There was a significant reduction in signal between PEG-mIL2-mIL12 and the vehicle control group, and PEG-TK-mIL2-mIL12 and the vehicle control group (Dunnett's multiple comparisons test, $p \leq 0.05$).

Median survival times for animals treated with PEG-lucia (24.0 days), PEG-mIL12 (32.5 days), PEG-TK-mIL12 (28.0 days), PEG-mIL2-mIL12 (33.0 days), and PEG-TK-mIL2-mIL12 (27.0 days) were significantly ($p \leq 0.05$, Log-rank test) longer than 9.5% Trehalose control (22.0 days) (FIG. 10). Survival times were significantly extended ($p \leq 0.05$, Log-rank test) for the PEG plasmids expressing IL-12 over PEG-lucia (IL-12 negative control) Luminescence readings on Study Day 12 indicated significant ($p \leq 0.05$) inhibition of tumor growth by treatment with PEG-mIL2-mIL12 compared with 9.5% Trehalose control (FIG. 11) and a trend towards significance for PEG-mIL12 ($p=0.054$). Accordingly, these results demonstrate that the formulations of the present technology are useful in methods for treating cancer in a subject in need thereof.

Example 9: Syngeneic Model of Experimental Metastasis to the Lung Using B16F10-Red-Fluc Cells The anti-tumor effect of nanoparticles containing PEG-mIL12 and expressing mIL-12 was compared to recombinant mIL-12 protein administered subcutaneously. The experimental design was as Example 8 but nanoparticles were prepared at N/P=4 and N/P=6 ratios. Nanoparticles were dosed as before for N/P=6, however, for the N/P=4 formulation the dose was maintained at 2 mg/kg in 10 mL/kg at day 8. For dosing of the recombinant protein, 10 μg of recombinant mIL-12 (PeproTech, Rocky Hill, NJ, USA) were reconstituted in PBS to make a 100 μg/mL stock solution. Dosing of the animals was at 4 μg/kg for the initial dose (Day 5) followed by four subsequent doses 12 μg/kg at the same intervals as the nanoparticles (Day 8, 11, 14 and 17).

Results—

Figure 12:
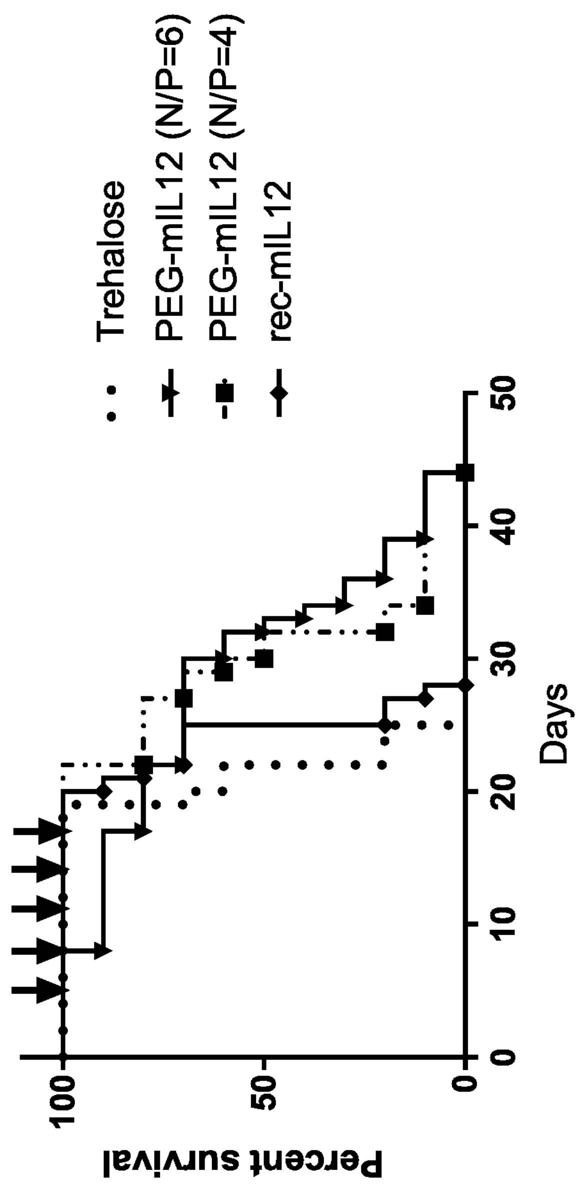
FIG. 12 shows a Kaplan Meier survival plot of anti-tumor activity in vivo of two preparations (N/P=4 and N/P=6) of PEG3-mIL-12 nanoparticles in a B16F10-Red-Fluc experimental model of metastatic lung cancer. Nanoparticles were dosed at 3 day intervals, beginning at day 5 (post tumor cell inoculation) as indicated by the arrows above the plot. The nanoparticle formulations produced a significant survival benefit over vehicle control (Trehalose) ($p \leq 0.01$, Log rank test) and over the recombinant murine IL-12 ($p \leq 0.05$, Log rank test) at the dose tested.
Figure 13:
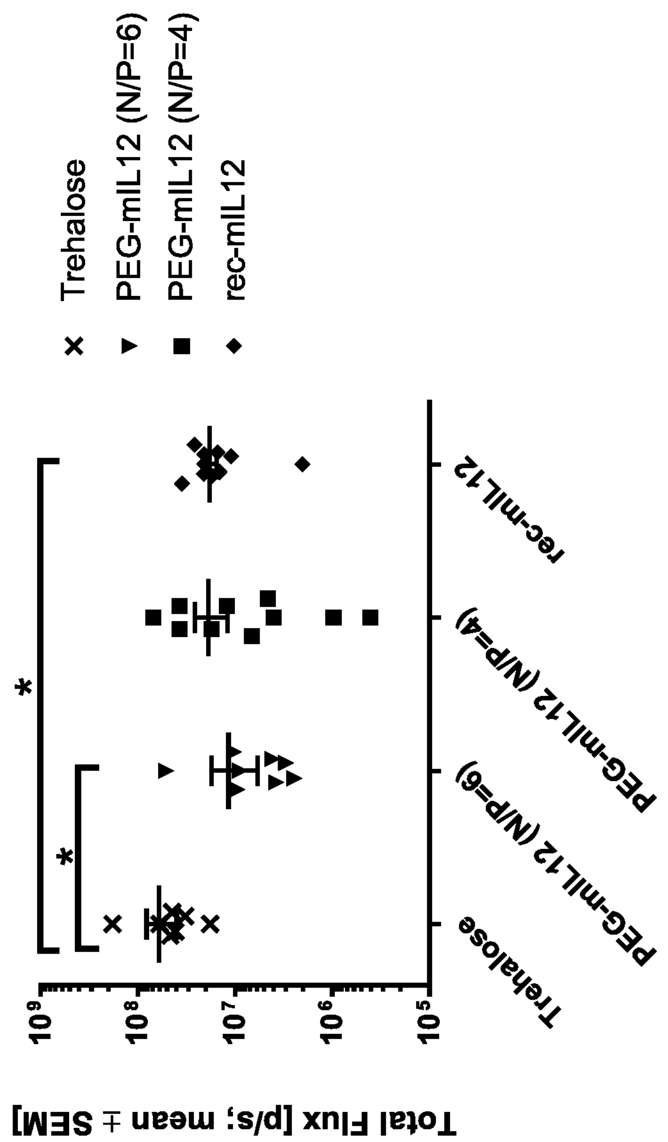
FIG. 13. Anti-tumor activity of PEG-3 nanoparticles used in the experimental metastasis study (shown in FIG. 12) were assessed through comparison of the mean in vivo luminescence signal±SEM (Total Flux (p/s)) in the lungs of C57BL/6 mice 19 days after inoculation of B16F10-Red-FLuc cells. The luminescent signal is indicative of the growth of tumor cells expressing firefly luciferase. There was a significant reduction in signal between PEG-mIL12 (N/P=6) and the vehicle control groups, and recombinant mIL-12 and the vehicle control groups (Dunnett's multiple comparisons test, $p \leq 0.05$) and a trend towards significance ($p=0.0538$) for PEG-mIL12 (N/P=4).

Median survival times for animals treated with PEG-mIL12 nanoparticles (N/P=6) (32.5 days), PEG-mIL12 nanoparticles (N/P=4) (31.0 days) and recombinant mIL-12 (25.0 days) were significantly longer ($p \le 0.01$ for formulations of PEG-mIL12 and $p \le 0.05$ for recombinant mIL-12, Log-rank test) than the Trehalose control (22.0 days). Additionally, the median survival time for the PEG-mIL12 nanoparticles was significantly ($p \le 0.05$, Log-rank test) longer than recombinant mIL-12 at the dose tested (FIG. 12). The dose of recombinant IL-12 protein was chosen so that the toxic side-effects of recombinant IL-12 would be minimized in this study, yet the protein would still be therapeutically effective (Yue et al., 2016, BMC Cancer 16:665; Car et al., 1999, Tox. Pathology 27, 58-63). Luminescence readings on Study Day 19 indicated significant ($p \le 0.05$) inhibition of tumor growth by treatment with PEG-mIL2 (N/P=6) and rec-mIL12 compared with 9.5% Trehalose control and a trend towards significance for PEG-mIL12 (N/P=4) (p=0.0538) (FIG. 13). Accordingly, these results demonstrate that the formulations of the present technology are useful in methods for treating cancer in a subject in need thereof.

Example 10: Evaluation of Anti-PD1 Antibody in an Experimental Metastasis to the Lung Using B16F10-Red-Fluc Cells The murine anti-PD1, iTME-0006-0002 (WO2016/170039), sequence was reverse-translated into a CpG-free DNA sequence and synthesized in fusion with mIL-12 or alone with 5' HindIII site and a 3' stop codon and a NheI site (SEQ ID NO: 19 and SEQ ID NO: 23, respectively). The cassette, iTME, is cloned into a pCpGfree plasmid (Invivogen, Carlsbad, CA, USA) containing the PEG-3 promoter to create PEG-iTME and PEG-mIL12-iTME and formulated into nanoparticles with PEI as described in Example 9. The nanoparticles are administered intravenously as previously described in mice harboring experimental metastases to the lung with B16F10-Red-Fluc cells. The effect of PEG-iTME and PEG-mIL12-iTME nanoparticles on survival and tumor growth is compared against Trehalose vehicle control and anti-murine PD-1, RMP1-14 ((#14-9982-81, Thermofisher Waltham, MA, USA) monoclonal antibody intravenously dosed at 4 mg/kg at each dosing point. It is predicted that the nanoparticles PEG-iTME and PEG-mIL12-iTME prolong survival of mice harboring metastatic tumors in the lung and are as effective or more effective than RMP1-14 monoclonal antibody. The same effect is anticipated in man when using recombinant humanized monoclonal antibodies alone or with human IL-12.

Figure 14:
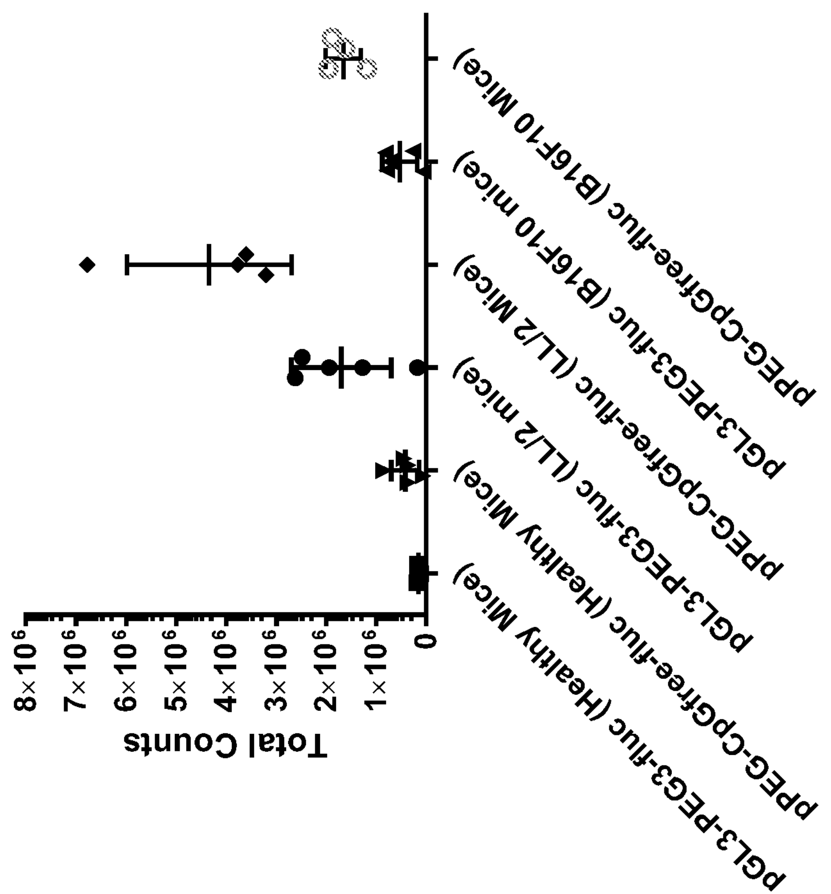
FIG. 14. Two plasmids were used to determine tumor specific expression in the context of CpG burden of the PEG-3 containing plasmids: one plasmid, pGL3-PEG3-fluc, a firefly luciferase gene whose expression is driven by the PEG-3 promoter, contains 357 CpG sites and pCpGfree-PEG-fluc, which is free of CpG sites (including the luciferase gene) with the exception of 43 CpG-sequences within the PEG3 promoter. Formulated nanoparticles were injected into NSG mice or mice, non-tumor bearing or containing LL/2 or B16F10 tumors. BLI imaging was performed 48 h post-injection of the nanoparticles. The region of interest was drawn to cover the entire lung region of each mouse and total flux (photon counts/sec) was calculated to determine the expression of the fLuc. The counts for individual mice treated with either plasmid were grouped. In both the LL/2 and B16F10 models, the pCpGfree-PEG-fluc groups have significantly more counts, corresponding to greater expression of firefly luciferase than in animals treated with the pGL3-PEG3-fluc plasmid. There was no significant difference between the two plasmids in terms of luciferase expression in healthy animals.

Example 11: In Vivo Bioluminescence Imaging in the NSG-LL2 and NSG-B16F10 Models with CpG Containing and CpG-Free Payload Either LL/2 or B16F10 cells were injected via the tail vein into 6-8 week old NSG mice (10e6 cells per mouse) and were left to infect in the lungs for approximately one week for LL/2 and two weeks for B16F10. Two plasmids were used to determine tumor specific expression in the context of CpG burden of PEG-3 containing plasmids: one plasmid, pGL3-PEG3-fluc, contains 357 CpG sites within the plasmid backbone and the luciferase gene whose expression is driven by the PEG-3 promoter, and the second plasmid pPEG-CpGfree-fluc, is CpG free except for 43 CpG-sequences within the PEG3 promoter. The plasmids were formulated with in vivo-jetPEI® (N/P=6) and the nanoparticles were injected into non-tumor bearing NSG mice or mice containing NSG-LL/2 and NSG-B16F10 tumors (40 μg of plasmid per mouse). BLI imaging was performed 48 h post-injection of the nanoparticles as follows: the mice were injected (i.p.) with 100 μL of D-luciferin (25 mg/mL in sterile PBS) and anesthetized with isoflurane (3%). Six minutes after the injection of D-luciferin, the mice were imaged for a duration of 3 min using the IVIS Spectrum Imaging System (Perkin Elmer) for bioluminescence signals. The region of interest was drawn to cover the entire lung region of each mouse and total flux (photon counts/sec) was calculated to determine the expression of the fLuc (FIG. 14). In the LL/2 and B16F10 models, the pPEG-CpGfree-fluc group has significantly ($p \le 0.05$, unpaired T-test) more counts, corresponding to greater expression of firefly luciferase than in animals treated with the pGL3-PEG3-fluc plasmid. There was no significant difference between the luciferase expression of the two plasmid formulations in healthy animals indicating there was no difference in background expression.

Example 12: In Vivo Toxicity of CpGhigh Versus CpGlow Plasmids

To further evaluate the benefit of reducing CpG within the plasmid and payload, an experiment was conducted to determine if there was a significant difference between a plasmid containing 43 CpG sites from the PEG-3 promoter (pCpGfree-PEG-TK) and an alternative plasmid containing 357 CpG sites pGL3-PEG3-fluc (a CpGhigh plasmid). Both plasmids were formulated with in vivo jetPEI® (Polyplus) N/P=6 and were injected into CD1 mice via the tail vein. Inflammatory response was determined by assay of the acute inflammatory cytokines IL-12, TNF-α, and IFN-γ. Although there was a cytokine response from both nanoparticle formulations, the pCpGfree-PEG-TK plasmid (CpGlow) showed a significant reduction in the induction of endogenous IL-12, TNF-α, and IFN-γ in serum compared with those resulting from CpG-containing pCpGfree-PEG-TK (Table 4). In particular, endogenous IL-12 induction was at least 100-fold less and IFN-γ at least 3-fold less, on average, for the CpGlow plasmid compared to the CpGhigh plasmid, therefore demonstrating greater safety for the CpGlow plasmid formulation.

TABLE 4

| Endogenous murine cytokine | Nanoparticle formulation | Mouse1 | Mouse2 | Mouse3 | Mouse4 | Mouse5 | Average | SD |
|---|---|---|---|---|---|---|---|---|
| IL-12 (sensitivity: 7.8 pg/mL) | Non-injected | ND | ND | ND | ND | ND | | |
| | pGL3-PEG3-fluc | 1202.9 | 593.9 | 747 | 989.4 | 972.4 | 901.1 | 235.6 |
| | pCpGfree-PEG-TK | BLQ | ND | ND | ND | BLQ | <7.8 | |
| TNF- α (sensitivity: 10.9 pg/mL) | Non-injected | ND | ND | ND | ND | ND | | |
| | pGL3-PEG3-fluc | 30.3 | 39.9 | 41.8 | 53.2 | 49.4 | 42.9 | 8.9 |
| | pCpGfree-PEG-TK | 21.2 | 30.2 | 26.7 | 38.8 | 27.3 | 28.8 | 6.5 |
| IFN-γ (sensitivity: 9.3 pg/mL) | Non-injected | ND | ND | ND | ND | ND | | |
| | pGL3-PEG3-fluc | 23108.9 | 17320 | 15293.3 | 22882.2 | 20404.4 | 19801.8 | 3437.8 |
| | pCpGfree-PEG-TK | 6091.1 | 8520 | 5848.9 | 5633.3 | 5293.3 | 6277.3 | 1287.5 |

ND: Not detected.
BLQ: Below the limit of quantification.

Example 13: Activity of PEG-hIL12 and PEG-hIL24 in Humanized (CD34+) NSG Mice Twelve animals ($CD34^+$ HU-NSG™ mice) humanized from $CD34^+$ cells from a single human umbilical cord donor (Jackson Laboratory, Bar Harbor, Maine, US) were inoculated while under isoflurane inhalation anesthesia (Study Day 0) with 10e6 MDA-MB-231-luc2 cells (Perkin Elmer, Waltham, Massachusetts, US) via the tail vein. Animals were randomized using a matched pair distribution method based on body weight prior to administration of the test articles on day 4. Imaging for in vivo luminescence signal in the thoracic region on Day 8 confirmed the presence of lung tumors. The nanoparticles that were tested were formulated with PEG-lucia, PEG-hIL12 and PEG-IL24 and invivo-jetPEI. Nanoparticles were administered at 1.5 mg/mL following reconstitution in ultrapure nuclease free water in a dosing volume of 7.5 mL/kg. on study days 4, 7, 10, 13, 16, and 19.

Figure 15:
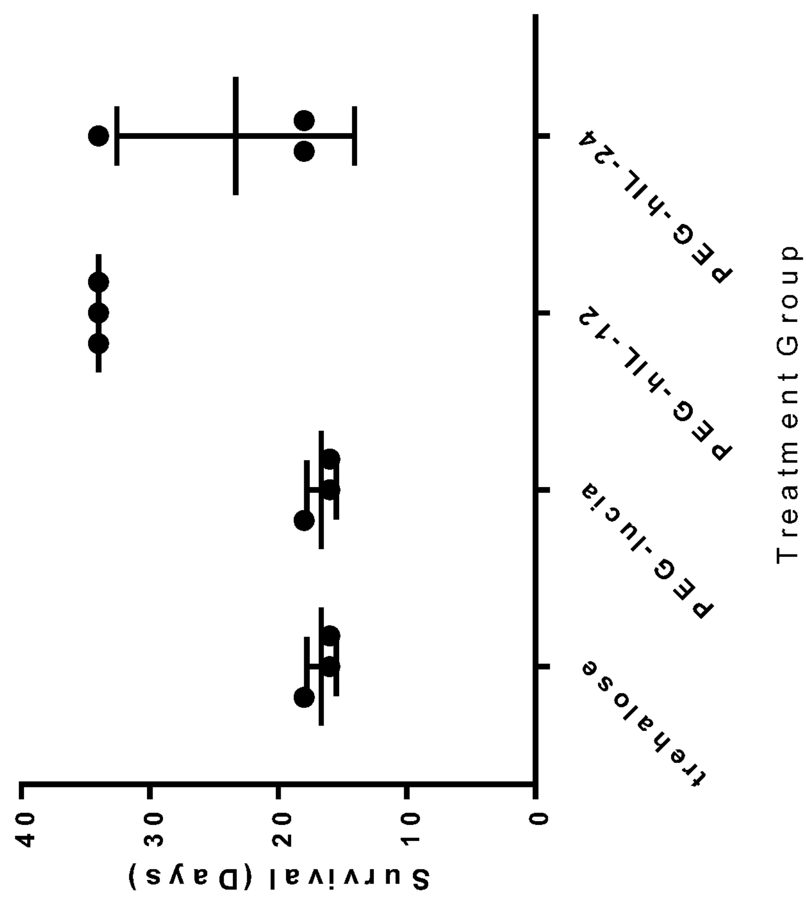
FIG. 15. Twelve animals ($CD34^{+}$ HU-NSG™ mice from a single human umbilical cord donor) were inoculated with of $10^{6}$ MDA-MB-231-luc2 cells and tumor growth was confirmed on Day 8 using BLI imaging of the lungs. PEG-lucia, PEG-hIL12 and PEG-IL24 nanoparticles were dosed on study days 4, 7, 10, 13, 16, and 19 and the animals were monitored over a period of 32 days and survival was noted. As observed from the survival data, individual animals treated with nanoparticles containing the human IL-12 and human IL-24 plasmids (PEG-hIL12 and PEG-hIL24, respectively) survived longer compared to animals in the control groups.

Animals were assessed daily for clinical condition and body weight loss in accordance with ethical guidelines: body weight loss exceeding 15% of initial body weight, or the presence of severe adverse clinical and/or physical signs of toxicity in any animal were considered as criteria for cessation of treatment to the entire group. The animals were monitored over a period of 32 days and survival was noted. As observed from the survival data, individual animals treated with nanoparticles harbouring the PEG-hIL12 and PEG-hIL24 plasmids survived longer compared to animals in the control groups (FIG. 15).

Example 14: Expression of Promiscuous T Cell Epitopes to Enhance Immunogenicity of Tumor Associated Antigens or Neoantigens This example will demonstrate that the expression of promiscuous T cell epitopes to enhance immunogenicity of tumor associated antigens or neoantigens for the treatment of cancer in subject in need thereof.

A cassette is designed to express the promiscuous T cell epitopes derived from tetanus toxin and measles virus fusion protein. These antigens are known T helper MHC II antigens that overcome haplotype restrictions and can elicit $CD4^+$ responses in mice and humans (Lairmore, et al., J. Virol. 69: 6077-6089, 1995). The fusion construct includes an expression cassette driven by PEG-3 promoter, cloned into pCpG-free-N-mcs (Invivogen), containing DNA encoding measles virus fusion protein epitope 288-302 (GenBank: AAA56641.1), tetanus toxin 580-599 (*Clostridium tetani* ATCC 9441), and tetanus toxin 830-844 (Valmori et al., 1992 J. Immunol 149: 717-721), each separated by the lysosomal protein cathepsin S cleavage sequence PMGLP (Fraser, et al., Vaccine, 32: 2896-2903, 2014) (SEQ ID NO: 24). The cassette is cloned 3' to the PEG-3 promoter using HindIII and NheI sites resulting in plasmid PEG-MVFTT. An additional plasmid was created containing the murine IL-12 sequence, as a single chain molecule, by appending the CpG-free codon sequence for murine IL-12, a furin cleavage sequence, a GSG linker and a P2A ribosomal skipping sequence onto the 5' of the MVFTT cassette (SEQ ID NO: 25) followed by cloning into a CpG-free PEG-3 plasmid using HindIII-NheI sites. This plasmid is known as PEG-mIL12-MVFTT.

Nanoparticles comprising the plasmids and a linear PEI polymer (in vivo-jetPEI®, Polyplus Transfection, Illkirch, France) are prepared under high pressure using a confined impinged jet (CIJ) device. The CIJ device and all the fittings are autoclaved on a dry cycle prior to use. A working solution of in vivo-jetPEI® is made in 9.5% Trehalose and combined under pressure with a stock solution of plasmid in 9.5% Trehalose (according to US Patent Application Publication No. 2017/0042829). The plasmids are formulated at a N/P=4 ratio followed by lyophilization in 0.06 mg (DNA) aliquots. Each formulated plasmid is reconstituted in 0.06 mg of 300 μL of nuclease-free water on the day of dosing.

Tumor Cell Culture and Inoculation—

B16F10-Red-FLuc mouse melanoma cells (Perkin Elmer, Waltham, MA, USA) are cultured in RPMI 1640 cell culture medium supplemented with 10% FBS, 1% GlutaMAX™, and 1% penicillin-streptomycin, and grown at 37° C. in a humidified cell culture incubator supplied with 5% $CO_2$. The cells are harvested by trypsinization, washed twice in HBSS and counted (using trypan blue exclusion). The final cell density is adjusted with HBSS to 3.5×10e6 cells/mL. 100 μL of cell suspension, consisting of 3.5×10e5 cells, is discharged into the tail vein of mice at the start of the study (Day 0). Imaging is performed on study Day 5, when the presence of lung tumors is confirmed in sufficient animals to commence the study.

Nanoparticle Dosing—

9.5% Trehalose buffer and nanoparticles containing pPEG-MVFTT, pPEG-mIL12-MVFTT, and pPEG-lucia (each 60 μg/vial) are reconstituted in 300 μL of nuclease-free water per vial on the day of dosing to give dosing solutions of 200 μg/mL. Formulated test articles are stored at 4° C. and used on day of reconstitution. 9.5% Trehalose buffer and nanoparticles containing PEG-MVFTT, PEG-mIL12-MVFTT, and PEG-lucia are administered via intravenous injection (i.v.) at a dose of 2 mg/kg in a dosing volume of 10 mL/kg on Study Days 5, 8, 11, 14, and 17.

Anticipated Results—

It is predicted that the expression of the promiscuous MHCII antigens will cause an immune response against the cells transfected with nanoparticles formulated with plasmids PEG-MVFTT and PEG-mIL12-MVFTT augmenting proliferation of $CD8^{+}$ cells. Release of tumor antigens from tumor cell destruction will lead to further stimulation of the immune system, which provides improved survival compared to the vehicle control or PEG-lucia plasmid nanoparticle control. Therefore, median survival times for animals treated with PEG-MVFTT or PEG-mIL12-MVFTT are improved over PEG-lucia and 9.5% Trehalose. These results will demonstrate the utility and efficacy of compositions and methods of the present technology for the treatment of cancer in subject in need thereof.

Example 15: Preparation of Plasmids for Expression of Tumor Associated Antigens/Neoantigens in a Cancer Cell This example will demonstrate the preparation of plasmids for expression of tumor associated antigens/neoantigens in a cancer cell.

A cassette is designed to improve the antigenicity of tumors by directing therapeutic monoclonal antibodies or chimeric antigen receptor (CAR) T cell therapies to recognize cancer cells and enhance tumor eradication. Cassettes were designed to be CpG-free and express human EGFRvIII (NCBI: NP_001333870.1 residues 1-377) or human HER2 domain IV (P04626-ERBB2 HUMAN, residues 1-22 and 510-652) truncated proteins as fusions with either native transmembrane (TM) or the TM domain of PDGFR (GenBank: AAA36427.1, residues 513-561) under the control of the PEG-3promoter. The PDGFR TM domain is used to replace the native Erb TM regions to prevent self-association with other Erb TM domains (Medrola et al., 2002, J. Biol. Chem., 4704-4712). Both EGFRvIII and HER2 domain IV lacked growth factor binding regions and cytoplasmic kinase domains so that these proteins would be inactive. Furthermore, Cys40 in EGFRvIII was mutated to serine to prevent disulphide-linked dimers (Stec et al., 2018, Oncotarget, 8560-8572). The CpG-free cassettes (SEQ ID NO: 26 and SEQ ID NO: 27) are cloned using HindIII-NheI or NcoI-NheI sites (for EGFRvIII and HER2 domain IV, respectively) into CpG-free plasmids containing PEG-3 promoter and these are named PEG-HERd4 and PEG-EGFRv3 for HER2 domain IV (HERd4) and EGFRvIII (EGFRv3) domains, respectively. In addition, the sequences for EGFRvIII and Her2 domain IV may be individually fused downstream of CpG-free murine IL-12, a furin cleavage site, GSG linker, and a P2A ribosome skipping sequence (SEQ ID NO: 28 and SEQ ID NO: 29, respectively) to form plasmids PEG-mIL12-EGFRv3 and PEG-mIL12-HERd4. Nanoparticles of the plasmids are made as described for the previous example, at a N/P=4 ratio followed by lyophilization in 0.06 mg (DNA) aliquots in 9.5% Trehalose. Each formulated plasmid is reconstituted in 0.06 mg of 300 μL of nuclease-free water on the day of dosing.

Example 16: Treatment of Tumors with PEG-3 Promoter Driven Expression of Antigen and a Therapeutic Monoclonal Antibody This example will demonstrate the treatment of tumors with PEG-3 promoter driven expression of antigen and a therapeutic monoclonal antibody.

Tumor Cell Culture and Inoculation—

B16F10-Red-FLuc mouse melanoma cells (Perkin Elmer, Waltham, MA, USA) are cultured in RPMI 1640 cell culture medium supplemented with 10% FBS, 1% GlutaMAX™, and 1% penicillin-streptomycin, and grown at 37° C. in a humidified cell culture incubator supplied with 5% $CO_2$. The cells are harvested by trypsinization, washed twice in HBSS and counted (using trypan blue exclusion). The final cell density is adjusted with HBSS to 3.5×10e6 cells/mL. 100 μL of cell suspension, consisting of 3.5×10 e5 cells, is discharged into the tail vein of mice at the start of the study (Day 0). Imaging is performed on study Day 5, when the presence of lung tumors is confirmed in sufficient animals to commence the study.

Nanoparticle Dosing—

9.5% Trehalose buffer and nanoparticles containing PEG-HERd4, PEG-mIL12-HERd4, and PEG-lucia (each 60 μg/vial) are reconstituted in 300 μL of nuclease-free water per vial on the day of dosing to give dosing solutions of 200 μg/mL. Formulated test articles are stored at 4° C. and used on day of reconstitution. 9.5% Trehalose buffer and nanoparticles containing PEG-HERd4, PEG-mIL12-HERd4, and PEG-lucia are administered via intravenous injection (i.v.) in a dosing volume of 10 mL/kg into different groups of mice. Treatments are administered at a dose of 2 mg/kg in a dosing volume of 10 mL/kg on Study Days 5, 8, 11, 14, and 17. Monoclonal antibody treatments of anti-human HER2 mouse monoclonal 4D5 (ATCC CRL-10463) are administered intraperitoneally at Day 5, 11, and 17 at 30 mg/kg in PBS.

Anticipated Results—

The human HER2 domain 4 sequence encompasses the epitope recognized by the mouse monoclonal antibody 4D5 (mAb4D5) and its humanized counterpart, trastuzumab (Herceptin). In this experiment, mAb4D5 antibody recognizes the HERd4 antigen expressed from the plasmid PEG-HER4d and PEG-mIL12-HER4d specifically in a cancer cell due to the activity of the cancer cell promoter, and binds to the surface of the cells. This elicits an antibody-dependent cell-mediated cytotoxicity response against those cells. Therefore, it is anticipated that median survival times for animals treated with nanoparticles formulated with PEG-HERd4, or PEG-mIL12-HERd4 combined with mAb4D5 treatment are improved over mice treated with the control nanoparticles containing PEG-lucia or vehicle control 9.5% Trehalose, and treated with murine mAb4D5. mAb4D5 is the non-humanized equivalent of trastuzumab (Herceptin) and it is anticipated that the same effect would be achieved in humans using the same HERd4 epitope with trastuzumab.

These results will show that the combination of the nucleic acid expression constructs of the present technology and therapeutic antibodies is useful in methods for treating cancer in a subject in need thereof.

Example 17: Treatment of Tumors with Murine CAR (mCAR) T-Cells and PEG-3 Promoter Driven Expression of Antigen This example will demonstrate the treatment of tumors with murine CAR (mCAR) T-cells and PEG-3 promoter driven expression of antigen.

Tumor Cell Culture and Inoculation—

B16F10-Red-FLuc mouse melanoma cells (Perkin Elmer, Waltham, MA, USA) are cultured in RPMI 1640 cell culture medium supplemented with 10% FBS, 1% GlutaMAX™, and 1% penicillin-streptomycin, and grown at 37° C. in a humidified cell culture incubator supplied with 5% $CO_2$. The cells are harvested by trypsinization, washed twice in HBSS and counted (using trypan blue exclusion). The final cell density is adjusted with HBSS to 3.5×10e6 cells/mL. 100 μL of cell suspension, consisting of 3.5×10e5 cells, is discharged into the tail vein of mice at the start of the study (Day 0). Imaging is performed on study Day 5, when the presence of lung tumors is confirmed in sufficient animals to commence the study.

CAR T-Cell Preparation—

Murine CAR T-Cells are developed according to Sampson, et al. (Clin Cancer Res; 1-13, 2013) in which mAb139 scFv is inserted in tandem with mCD8 trans-membrane, mCD28, m4-1BB, and mCD3z intracellular regions in the MSGV1 retroviral vector. mAb139 scFv is isolated from a human antibody clone specific for human EGFRvIII. Retroviral supernatant is generated by transient co-transfection of HEK 293T cells by Lipofectamine 2000 Transfection Reagent (Thermofisher, Carlsbad, CA, USA), along with pCL-Eco helper plasmid (Novus Biologicals, Littleton, CO, USA). The resulting retroviral supernatant is used to transduce murine splenocytes by collecting spleens from C57BL/6 mice, disaggregating, and passing through a 70-μm mesh filter to generate a single-cell suspension. Cells are cultured in complete R10 mouse T-cell media supplemented with 1 ng/mL rmIL-7 and activated on day 0 with 2.5 mg/mL Concanavalin A (ConA). T-cells are transduced on RetroNectin-coated plates (Takara Inc., Mountain View, CA, USA) at a density of 10e6/mL on day 2 after stimulation. Cells are then maintained at 1 to 2×10e6/mL in mouse T-cell media with 50 IU/mL rhIL-2 for 4 to 7 days. Surface expression of the anti-EGFRvIII mCAR is tested on B16F10 cells transfected with PEG-EGFRv3 plasmid in vitro and using an Alexa Fluor labelled peptide of the known EGFRvIII peptide epitope (LEEKKGNYVVTDHC) (SEQ ID NO: 30) and detected by fluorescent microscopy or FACS.

Car T Implantation—

Five days following tumor cell implantation, mice are treated with 10e7 mCAR C57BL/6 T-cells (absolute number) delivered systemically via tail vein injection. Mice are conditioned with 5 Gy total body irradiation (TBI) immediately before T-cell transfer.

Nanoparticle Dosing—

9.5% Trehalose buffer and nanoparticles containing PEG-EGFRv3, PEG-mIL12-EGFRv3, and PEG-lucia are administered via intravenous injection (i.v.) at a dose of 2 mg/kg on Study Days 8, 11, 14, and 17 in a dosing volume of 10 mL/kg into groups of anti-EGFRv3 mCAR treated mice. The groups are as follows to elucidate the benefit of antigen expression in the tumor for localizing the CAR T-Cell response: anti-EGFRvIII mCAR+9.5% Trehalose (vehicle control); anti-EGFRvIII mCAR+PEG-lucia (plasmid control); anti-EGFRvIII mCAR+PEG-EGFRv3; anti-EGFRvIII mCAR+mIL12-EGFRv3.

Anticipated Results—

It is anticipated that treatment with anti-EGFRvIII CAR and nanoparticles containing the plasmids PEG-mIL12-EGFRv3 and PEG-EGFRv3 will increase the survival of mice harboring B16F10 tumors in the lung as a result of expression of the EGFRvIII specifically in cancer cells transfected by the nanoparticles. The antigen is recognized by the murine CAR T-Cells, which are activated to elicit an immune response against these cancer cells and not cells that are transfected with the control plasmid or those treated with Trehalose vehicle control. Therefore, it is predicted that survival times for animals treated with anti-EGFRvIII mCAR+PEG-mIL12-EGFRv3 or anti-EGFRvIII mCAR+PEG-EGFRv3 will be improved over anti-EGFRvIII mCAR+PEG-lucia and anti-EGFRvIII mCAR+9.5% Trehalose controls. It is further anticipated that administration of the nucleic acid expression constructs, PEG-mIL12-EGFRv3 or PEG-EGFRv3 in combination with the anti-EGFRvIII mCAR T-Cells (i.e., anti-EGFRvIII mCAR+PEG-mIL12-EGFRv3 or anti-EGFRvIII mCAR+PEG-EGFRv3) will have synergistic effects in this regard compared to that observed with either the expression constructs or mCAR T-Cells alone.

These results will show that the combination of the nucleic acid expression constructs of the present technology with CAR T-Cell immunotherapy is useful in methods for treating cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a nonlimiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

SEQUENCE LISTING
For the sequences provided herein:
*BOLD ITALICS* = restriction endonuclease cleavage sites used for cloning.
HSV1-TK CpGfree (NcoI-BamHI-NheI)

>SEQ ID NO: 1

*CCATGG*CTTCTTACCCTGGACACCAGCATGCTTCTGCCTTTGACCAGGCTGCCAG

ATCCAGGGGCCACTCCAACAGGAGAACTGCCCTAAGACCCAGAAGACAGCAGG

AAGCCACTGAGGTGAGGCCTGAGCAGAAGATGCCAACCCTGCTGAGGGTGTACA

TTGATGGACCTCATGGCATGGGCAAGACCACCACCACTCAACTGCTGGTGGCACT

GGGCTCCAGGGATGACATTGTGTATGTGCCTGAGCCAATGACCTACTGGAGAGT

GCTAGGAGCCTCTGAGACCATTGCCAACATCTACACCACCCAGCACAGGCTGGA

CCAGGGAGAAATCTCTGCTGGAGATGCTGCTGTGGTGATGACCTCTGCCCAGATC

ACAATGGGAATGCCCTATGCTGTGACTGATGCTGTTCTGGCTCCTCACATTGGAG

GAGAGGCTGGCTCTTCTCATGCCCCTCCACCTGCCCTGACCCTGATCTTTGACAG

ACACCCCATTGCAGCCCTGCTGTGCTACCCAGCAGCAAGGTACCTCATGGGCTCC

ATGACCCCACAGGCTGTGCTGGCTTTTGTGGCCCTGATCCCTCCAACCCTCCCTG

GCACCAACATTGTTCTGGGAGCACTGCCTGAAGACAGACACATTGACAGGCTGG

CAAAGAGGCAGAGACCTGGAGAGAGACTGGACCTGGCCATGCTGGCTGCAATCA

GAAGGGTGTATGGACTGCTGGCAAACACTGTGAGATACCTCCAGTGTGGAGGCT

CTTGGAGAGAGGACTGGGGACAGCTCTCTGGAACAGCAGTGCCCCCTCAAGGAG

CTGAGCCCCAGTCCAATGCTGGTCCAAGACCCCACATTGGGGACACCCTGTTCAC

CCTGTTCAGAGCCCCTGAGCTGCTGGCTCCCAATGGAGACCTGTACAATGTGTTT

GCCTGGGCTCTGGATGTTCTAGCCAAGAGGCTGAGGTCCATGCATGTGTTCATCC

TGGACTATGACCAGTCCCCTGCTGGATGCAGAGATGCTCTGCTGCAACTAACCTC

TGGCATGGTGCAGACCCATGTGACCACCCCTGGCAGCATCCCCACCATCTGTGAC

CTAGCCAGAACCTTTGCCAGGGAGATGGGAGAGGCCAAT*GGATCC*TGATAA*GCT*

*GCT*

SR39 (NcoI-BamHI-NheI)

>SEQ ID NO: 2

*CCATGG*CTTCTTACCCTGGACACCAGCATGCTTCTGCCTTTGACCAGGCTGCCAG

ATCCAGGGGCCACTCCAACAGGAGAACTGCCCTAAGACCCAGAAGACAGCAGG

AAGCCACTGAGGTGAGGCCTGAGCAGAAGATGCCAACCCTGCTGAGGGTGTACA

TTGATGGACCTCATGGCATGGGCAAGACCACCACCACTCAACTGCTGGTGGCACT

GGGCTCCAGGGATGACATTGTGTATGTGCCTGAGCCAATGACCTACTGGAGAGT

GCTAGGAGCCTCTGAGACCATTGCCAACATCTACACCACCCAGCACAGGCTGGA

CCAGGGAGAAATCTCTGCTGGAGATGCTGCTGTGGTGATGACCTCTGCCCAGATC

ACAATGGGAATGCCCTATGCTGTGACTGATGCTGTTCTGGCTCCTCACATTGGAG

GAGAGGCTGGCTCTTCTCATGCCCCTCCACCTGCCCTGACCATTTTCCTGGACAG

ACATCCCATTGCCTTCATGCTGTGCTACCCAGCAGCAAGGTACCTCATGGGCTCC

ATGACCCCACAGGCTGTGCTGGCTTTTGTGGCCCTGATCCCTCCAACCCTCCCTG

GCACCAACATTGTTCTGGGAGCACTGCCTGAAGACAGACACATTGACAGGCTGG

CAAAGAGGCAGAGACCTGGAGAGAGACTGGACCTGGCCATGCTGGCTGCAATCA

-continued

GAAGGGTGTATGGACTGCTGGCAAACACTGTGAGATACCTCCAGTGTGGAGGCT

CTTGGAGAGAGGACTGGGGACAGCTCTCTGGAACAGCAGTGCCCCCTCAAGGAG

CTGAGCCCCAGTCCAATGCTGGTCCAAGACCCCACATTGGGGACACCCTGTTCAC

CCTGTTCAGAGCCCCTGAGCTGCTGGCTCCCAATGGAGACCTGTACAATGTGTTT

GCCTGGGCTCTGGATGTTCTAGCCAAGAGGCTGAGGTCCATGCATGTGTTCATCC

TGGACTATGACCAGTCCCCTGCTGGATGCAGAGATGCTCTGCTGCAACTAACCTC

TGGCATGGTGCAGACCCATGTGACCACCCCTGGCAGCATCCCCCACCATCTGTGAC

CTAGCCAGAACCTTTGCCAGGGAGATGGGAGAGGCCAAT*GGATCC*TGATAA*GCT*

*AGC* human IL-2 (HindIII-NheI)

>SEQ ID NO: 3

*AAGCTT*GGCATTCCGGTACTGTTGGTAAAGCCACCATGTACAGGATGCAACTCCT

GTCTTGCATTGCACTGAGTCTTGCACTTGTCACAAACAGTGCACCTACTTCAAGT

TCTACAAAGAAAACACAGCTGCAACTGGAGCATCTCCTGCTGGATCTGCAGATG

ATCTTGAATGGAATTAATAATTACAAGAATCCCAAACTCACCAGGATGCTCACAT

TTAAGTTTTACATGCCCAAGAAGGCCACAGAACTGAAACATCTTCAGTGTCTGGA

AGAAGAACTCAAACCTCTGGAGGAAGTGCTCAATCTGGCTCAAAGCAAAAACTT

TCACCTGAGACCCAGGGACCTGATCAGCAATATCAATGTAATTGTTCTGGAACTC

AAGGGATCTGAAACAACATTCATGTGTGAATATGCTGATGAGACAGCAACCATT

GTGGAATTTCTGAACAGATGGATTACCTTTTGTCAAAGCATCATCTCAACACTGACTTAAA

CCTGA*GCTAGC* murine IL-2 (HindIII-NheI)

>SEQ ID NO: 4

*AAGCTT*GGCATTCCGGTACTGTTGGTAAAGCCACCATGTACAGCATGCAGCTGGC

CTCCTGTGTGACACTGACACTGGTGCTGCTGGTGAACTCTGCACCCACTTCAAGC

TCCACCTCAAGCTCTACAGCTGAAGCCCAGCAGCAGCAGCAGCAGCAGCAGCAG

CAGCAGCAGCACCTGGAGCAGCTGCTGATGGACCTGCAGGAGCTGCTGAGCAGG

ATGGAGAATTACAGGAACCTGAAACTCCCCAGGATGCTGACCTTCAAATTTTACT

TGCCCAAGCAGGCCACAGAACTGAAGGATCTGCAGTGCCTGGAAGATGAACTTG

GACCTCTGAGGCATGTGCTGGATCTGACTCAAAGCAAGAGCTTTCAACTGGAAG

ATGCTGAGAATTTCATCAGCAATATCAGAGTGACTGTGGTCAAACTGAAGGGCT

CTGACAACACATTTGAGTGCCAATTTGATGATGAGTCAGCCACTGTGGTGGACTT

TCTGAGGAGATGGATTGCCTTCTGTCAAAGCATCATCTCAACAAGCCCTCAATAAACCTGA

*GCTAGC* human scIL-12 (NotI-NheI)

>SEQ ID NO: 5

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

-continued

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCTAAACCTGA

*GCTAGC* murine scIL-12 (HindIII-NheI)

>SEQ ID NO: 6

*AAGCTT*GGCATTCCGGTACTGTTGGTAAAGCCACCATGTGTCCTCAGAAGCTCAC

CATCTCCTGGTTTGCCATTGTTTTGCTGGTGTCTCCACTCATGGCCATGTGGGAGC

TGGAGAAAGATGTTTATGTTGTGGAGGTGGACTGGACTCCTGATGCCCCTGGAGA

AACAGTGAACCTCACCTGTGACACCCCTGAAGAAGATGACATCACCTGGACCTC

AGACCAGAGACATGGAGTCATAGGCTCTGGAAAGACCCTGACCATCACTGTCAA

AGAGTTTCTGGATGCTGGCCAGTACACCTGCCACAAAGGAGGGGAGACTCTGAG

CCACTCACATCTGCTGCTCCACAAGAAGGAAAATGGAATTTGGTCCACTGAAATT

CTGAAAAATTTCAAAAACAAGACTTTCCTGAAGTGTGAAGCACCAAATTACTCTG

GAAGGTTCACCTGCTCATGGCTGGTGCAAAGAAACATGGACTTGAAGTTCAACA

TCAAGAGCAGTAGCAGTTCCCCTGACTCTAGGGCAGTGACATGTGGAATGGCCT

CTCTGTCTGCAGAGAAGGTCACACTGGACCAAAGGGACTATGAGAAGTATTCAG

TGTCCTGCCAGGAGGATGTCACCTGCCCAACTGCTGAGGAGACCCTGCCCATTGA

ACTGGCCTTGGAAGCAAGGCAGCAGAATAAATATGAGAACTACAGCACCAGCTT

CTTCATCAGGGACATCATCAAACCAGACCCTCCCAAGAACTTGCAGATGAAGCC

TTTGAAGAACTCACAGGTGGAGGTCAGCTGGGAGTACCCTGACTCCTGGAGCAC

-continued

TCCCCATTCCTACTTCTCCCTCAAGTTCTTTGTTAGAATCCAGAGGAAGAAAGAA

AAGATGAAGGAGACAGAGGAGGGGTGTAACCAGAAAGGTGCCTTCCTGGTGGA

GAAGACATCTACAGAAGTCCAATGCAAAGGAGGGAATGTCTGTGTGCAAGCTCA

GGATAGGTATTACAATTCCTCATGCAGCAAGTGGGCATGTGTTCCCTGCAGGGTC

AGATCTGGTGGAGGTGGAAGTGGAGGTGGTGGATCTGGGGGTGGAGGCAGCAG

GGTCATTCCAGTCTCTGGACCTGCCAGGTGTCTTAGCCAGTCCAGAAACCTGCTG

AAGACCACAGATGACATGGTGAAGACTGCCAGAGAAAAACTGAAACATTATTCC

TGCACTGCTGAAGACATTGATCATGAAGACATCACAAGGGACCAAACCAGCACA

TTGAAGACCTGTCTGCCACTGGAACTGCACAAGAATGAGAGTTGCCTGGCTACTA

GAGAGACTTCTTCCACAACAAGAGGGAGCTGCCTGCCCCCACAGAAGACCTCTT

TGATGATGACCCTGTGCCTTGGTAGCATCTATGAGGACTTGAAGATGTACCAGAC

AGAGTTCCAGGCCATCAATGCAGCACTTCAGAATCACAACCATCAGCAGATCAT

TCTGGACAAGGGCATGCTGGTGGCCATTGATGAGCTGATGCAGTCTCTGAATCAT

AATGGAGAGACTCTGAGACAGAAACCTCCTGTGGGAGAAGCAGACCCTTACAGA

GTGAAAATGAAGCTCTGCATCCTGCTTCATGCCTTCAGCACCAGAGTGGTGACCA

TCAACAGGGTGATGGGCTATCTGAGCTCTGCCTAAACCTGA*GCTAGC* human IL-15 (Esp3I-NheI)

>SEQ ID NO: 7

*CGTCTCAGACC*TATGTACAGGATGCAACTCCTGTCTTGCATTGCACTGAGTCTTGC

ACTTGTCACAAACAGTGCAGGAGCCAACTGGGTGAATGTGATCAGTGATTTGAA

AAAAATTGAAGATCTTATTCAATCTATGCATATTGATGCTACTTTGTATACAGAA

AGTGATGTTCACCCCAGTTGCAAAGTGACAGCAATGAAGTGCTTTCTCTTGGAGC

TGCAAGTTATTTCACTTGAGTCTGGAGATGCAAGTATTCATGATACAGTGGAAAA

TCTGATCATC CTGGCAAACAACAGTTTGTCTTCTAATGGGAATGTGACAGAATCT

GGATGCAAAGAATGTGAGGAACTGGAGGAAAAAAATATTAAAGAATTTTTGCAG

AGTTTTGTGCATATTGTCCAAATGTTCATCAACACTTCTTAAACCTGA*GCTAGC* human IL-24 (HindIII-NheI)

>SEQ ID NO: 8

*AAGCTT*GGCATTCCGGTACTGTTGGTAAAGCCACCATGAATTTTCAACAGAGGCT

GCAAAGCCTGTGGACTCTGGCCAGACCCTTCTGCCCTCCTTTGCTGGCCACAGCC

TCTCAAATGCAGATGGTTGTGCTCCCTTGCCTGGGTTTTACCCTGCTTCTCTGGAG

CCAGGTGTCAGGGGCCCAGGGCCAAGAATTCCACTTTGGGCCCTGCCAAGTGAA

GGGGGTTGTTCCCCAGAAACTGTGGGAAGCCTTCTGGGCTGTGAAAGACACTAT

GCAAGCTCAGGATAACATCACCAGTGCCAGGCTGCTGCAGCAGGAGGTTCTGCA

GAATGTCTCTGATGCTGAGAGCTGTTACCTTGTCCACACCCTGCTGGAGTTCTAC

TTGAAAACTGTTTTCAAAAACTACCACAATAGAACAGTTGAAGTCAGGACTCTG

AAGTCATTCTCTACTCTGGCCAACAACTTTGTTCTCATTGTGTCACAACTGCAACC

CAGTCAAGAAAATGAGATGTTTTCCATCAGAGACAGTGCACACAGGAGGTTTCT

GCTGTTCAGAAGAGCATTCAAACAGTTGGATGTGGAAGCAGCTCTGACCAAAGC

CCTTGGGGAAGTGGACATTCTTCTGACCTGGATGCAGAAATTCTACAAGCTCTAAACCTGA

*GCTAGC*

-continued

P2A-human GM-CSF (BamHI-NheI)

>SEQ ID NO: 9

*GGATCC*TCTGGAAGTGGAGCTACTAACTTCAGCCTGCTGAAGCAGGCTGGAGAT

GTGGCTGCAGAGCCTGCTGCTCTTGGGCACTGTGGCCTGCAGCATCTCTGCACCT

GCCAGAAGCCCCAGCCCCAGCACCCAGCCCTGGGAGCATGTGAATGCCATCCAG

GAGGCCAGGAGGCTCCTGAACCTGAGTAGAGACACTGCTGCTGAGATGAATGAA

ACAGTGGAAGTCATCTCAGAAATGTTTGACCTCCAGGAGCCCACCTGCCTCCAGA

CCAGGCTGGAGCTGTACAAGCAGGGCCTGAGGGGCAGCCTCACCAAGCTCAAGG

GCCCCTTGACCATGATGGCCAGCCACTACAAGCAGCACTGCCCTCCAACCCCTGA

AACTTCCTGTGCAACCCAGATTATCACCTTTGAAAGTTTCAAAGAGAACCTGAAG

GACTTTCTGCTTGTCATCCCCTTTGACTGCTGGGAGCCAGTCCAGGAGTGAACCTGA

*GCTAGC*

P2A-murine GM-CSF (BamHI-NheI)

>SEQ ID NO: 10

*GGATCC*TCTGGAAGTGGAGCTACTAACTTCAGCCTGCTGAAGCAGGCTGGAGAT

GTGGAGGAGAACCCTGGACCTATGTGGCTGCAGAATCTGCTTTTCCTGGGCATTG

TGGTCTACAGCCTCTCAGCACCCACCAGGTCACCCATCACTGTCACCAGACCTTG

GAAGCATGTAGAGGCCATCAAAGAAGCCCTGAACCTCCTGGATGACATGCCTGT

CACCTTGAATGAAGAGGTAGAAGTGGTCTCTAATGAGTTCTCCTTCAAGAAGCTG

ACATGTGTGCAGACCAGACTGAAGATATTTGAGCAGGGTCTAAGGGGCAATTTC

ACCAAACTCAAGGGAGCCTTGAACATGACAGCCAGCTACTACCAGACATACTGC

CCCCCAACTCCTGAAACAGACTGTGAAACACAAGTTACCACCTATGCTGATTTCA

TAGACAGCCTTAAAACCTTTCTGACTGATATCCCCTTTGAATGCAAAAAACCAGGCCAAAA

ATGAACCTGA*GCTAGC*

P2A-PD1ECD-FcFurin (BamHI-Esp3I)

>SEQ ID NO: 11

*GGATCC*TCTGGAAGTGGAGCTACTAACTTCAGCCTGCTGAAGCAGGCTGGAGAT

GTGGAGGAGAACCCTGGACCTATGGACTGGACCTGGAGGGTCTTCTGTTTGCTGG

CTGTAACTCCAGGTGCCCACCCCCTGGACTCCCCAGACAGGCCCTGGAACCCCCC

CACCTTCTCCCCAGCCCTGCTGGTGGTGACTGAAGGGGACAATGCCACCTTCACC

TGCAGCTTCTCCAACACATCTGAGAGCTTTGTGCTGAACTGGTACAGGATGAGCC

CCAGCAACCAGACTGACAAGCTGGCTGCCTTCCCTGAGGACAGGAGCCAGCCTG

GCCAGGACTGCAGATTCAGGGTCACACAACTGCCCAATGGGAGGGACTTCCACA

TGAGTGTGGTCAGGGCCAGGAGAAATGACAGTGGCACCTACCTCTGTGGGGCCA

TCTCCCTGGCCCCCAAGGCCCAGATCAAAGAGAGCCTGAGGGCAGAGCTCAGGG

TGACAGAGAGAAGGGCAGAAGTGCCCACAGCCCACCCCAGCCCCTCACCCAGGT

CAGCTGGCCAGTTCCAAACCCTGGTGGAGTCCAAATATGGTCCCCCATGCCCACC

ATGCCCAGCACCTGAGTTTGAGGGGGGACCATCAGTCTTCCTGTTCCCCCCAAAA

CCCAAGGACACTCTCATGATCTCCAGGACCCCTGAGGTCACCTGTGTGGTGGTGG

ATGTGAGCCAGGAAGACCCTGAGGTCCAGTTCAACTGGTATGTGGATGGGGTGG

AGGTGCATAATGCCAAGACAAAGCCTAGGGAGGAGCAGTTCAACAGCACCTACA

GAGTGGTCAGTGTCCTCACAGTCCTGCACCAGGACTGGCTGAATGGCAAGGAGT

ACAAGTGCAAGGTCTCCAACAAAGGCCTCCCCTCCTCCATTGAGAAAACCATCTC

CAAAGCCAAAGGGCAGCCCAGAGAGCCACAGGTGTACACCCTGCCCCCATCCCA

-continued

GGAGGAGATGACCAAGAACCAGGTCAGCCTGACCTGCCTGGTCAAAGGCTTCTA

CCCCAGTGACATTGCTGTGGAGTGGGAGAGCAATGGGCAGCCTGAGAACAACTA

CAAGACCACACCTCCAGTGCTGGACTCTGATGGCTCCTTCTTCCTCTACAGCAGG

CTCACAGTGGACAAGAGCAGGTGGCAGGAGGGGAATGTCTTCTCATGCTCTGTG

ATGCATGAGGCTCTGCACAACCACTACACACAGAAGAGCCTCTCCCTGTCTCTGG

GTAAAAGAAGGAAGAGGGGAAGTGGAGAGGGCAGAGGAAGTCTGCTAACATGTGGTGATGT

GGAGGAGAATCCTG*GGACCTGAGACG*

FliC Esp3I-NheI

>SEQ ID NO: 12

*CGTCTCAGACC*TATGGAGACAGACACACTCCTGCTGTGGGTGCTGCTGCTCTGGG

TTCCAGGTTCCACTGGTGACATGGCACAAGTCATTAATACAAACAGCCTGTCTCT

GTTGACCCAGAATAACCTGAACAAATCCCAGTCAGCTCTGGGCACAGCTATTGA

GAGACTGTCTTCTGGTCTGAGGATCAACAGTGCCAAAGATGATGCTGCAGGTCA

GGCCATTGCTAACAGGTTTACTGCCAACATCAAAGGTCTGACTCAGGCTTCCAGA

AATGCTAATGATGGTATCTCCATTGCCCAGACCACTGAAGGAGCTCTGAATGAA

ATCAACAACAACCTGCAGAGAGTGAGGGAACTGGCTGTTCAGTCTGCTAACAGC

ACCAACTCCCAGTCTGACCTGGACTCCATCCAGGCTGAAATCACCCAGAGACTG

AATGAAATTGACAGAGTGTCTGGCCAGACTCAGTTCAATGGAGTGAAAGTCCTG

GCCCAGGACAACACCCTGACCATCCAGGTTGGTGCCAATGATGGTGAAACTATT

GATATTGATCTGAAGCAGATCAACTCTCAGACCCTGGGTCTGGATACCCTGAATG

TGCAACAAAAATATAAGGTCAGTGATACAGCTGCAACTGTTACAGGATATACTC

AAAATAAAGATGGTTCCATCAGTATTAATACTACAAAATACACTGCAGATGATG

GTACATCCAAAACTGCACTGAACAAACTGGGTGGGGCAGATGGCAAAACAGAA

GTTGTTTCTATTGGTGGTAAAACTTATGCTGCAAGTAAAGCTGAAGGTCACAACT

TTAAAGCACAGCCTGATCTGGCTGAAGCTGCTGCTACAACCACAGAAAACCCTCT

GCAGAAAATTGATGCTGCTTTGGCACAGGTTGACACCCTGAGATCTGACCTGGGT

GCTGTGCAGAACAGGTTCAACTCTGCTATTACCAACCTGGGCAACACAGTGAAC

AACCTGACTTCTGCCAGAAGCAGGATTGAAGATTCTGACTATGCCACAGAAGTTT

CCAACATGTCTAGAGCCCAGATTCTGCAGCAGGCTGGTACCTCTGTTCTGGCCCA

GGCCAACCAGGTTCCCCAAAATGTCCTCTCTCTGCTGAGATAAACCTGA*GCTAGC* hIL-12-Ipilimumab (NotI-NheI)

>SEQ ID NO: 13

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

-continued

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

GAGAGGATCCTCTGGAAGTGGAGCTACTAACTTCAGCCTGCTGAAGCAGGCTGG

AGATGTGGAGGAGAACCCTGGACCTATGGAGTTTGGGCTGAGCTGGGTTTTCCTT

GTTGCTCTTTTAAGAGGTGTCCAGTGTCAGGTGCAGTTGGTGGAGTCTGGGGGGG

GTGTGGTGCAGCCAGGGAGGTCACTGAGACTGAGTTGTGCAGCAAGTGGGTTTA

CATTTAGTAGTTATACAATGCATTGGGTTAGGCAAGCTCCAGGGAAGGGTCTGGA

GTGGGTGACTTTTATTTCTTATGATGGTAATAATAAATATTATGCAGATTCAGTTA

AGGGAAGGTTTACTATTAGTAGGGATAATTCAAAAAATACTCTGTATTTGCAGAT

GAATTCTCTGAGGGCTGAGGATACAGCTATTTATTATTGTGCTAGAACTGGTTGG

CTGGGTCCATTTGATTATTGGGGGCAGGGAACACTTGTGACAGTGTCATCAGCTT

CAACAAAAGGTCCATCTGTTTTTCCATTGGCTCCTTCTTCTAAGTCAACTTCTGGT

GGAACTGCAGCTCTGGGATGTCTGGTGAAGGATTATTTTCCAGAACCTGTGACTG

TTTCTTGGAATAGTGGTGCTCTGACTAGTGGAGTTCATACTTTTCCAGCTGTTCTG

CAGAGTTCTGGACTGTATTCTCTGAGTAGTGTGGTTACAGTTCCATCAAGTTCTCT

GGGTACTCAAACTTATATTTGTAATGTGAATCATAAGCCTTCAAATACAAAGGTG

GATAAAAGGGTGGAGCCAAAGTCATGTGATAAGACTCATACATGTCCTCCATGT

CCTGCTCCAGAGCTTCTGGGGGGGCCATCTGTTTTTCTGTTTCCACCAAAGCCTA

AGGATACTCTTATGATTAGTAGGACACCAGAAGTTACATGTGTGGTGGTTGATGT

GTCTCATGAAGATCCAGAGGTGAAGTTTAATTGGTATGTTGATGGGGTGGAGGTT

CATAATGCAAAGACAAAGCCTAGGGAGGAACAGTATAATAGTACATATAGAGTG

GTGTCTGTGCTGACTGTGCTGCATCAGGATTGGCTGAATGGAAAAGAGTATAAGT

-continued

GTAAAGTGTCAAATAAGGCTCTGCCTGCACCTATTGAAAAAACAATTTCAAAGG

CAAAAGGGCAGCCAAGGGAGCCTCAAGTTTATACTCTGCCACCTTCAAGGGATG

AACTTACAAAGAATCAAGTGAGTTTGACTTGTCTTGTGAAAGGATTTTATCCTTC

AGATATTGCTGTGGAGTGGGAGTCAAATGGTCAGCCTGAAAATAATTATAAGAC

TACTCCACCAGTGCTGGATAGTGATGGGTCTTTTTTTCTGTATAGTAAGCTGACTG

TGGATAAGTCTAGGTGGCAGCAGGGAAATGTGTTTTCTTGTAGTGTGATGCATGA

GGCTCTGCATAATCATTATACACAGAAGTCTCTGAGTTTGTCTCCTGGTAAAAGA

AGGAAGAGGGGAAGTGGAGAGGGCAGAGGAAGTCTGCTAACATGTGGTGATGT

GGAGGAGAATCCTGGACCTATGGACATGAGGGTCCCTGCTCAGCTCCTGGGGCT

CCTGCTGCTCTGGCTCTCAGGTGCCAGATGTGAGATTGTGCTGACACAATCTCCA

GGAACTTTGAGTCTGTCTCCAGGTGAGAGGGCTACACTGTCATGTAGGGCATCAC

AGTCTGTTGGAAGTTCTTATCTGGCTTGGTATCAACAAAAGCCTGGGCAGGCTCC

AAGACTGCTGATTTATGGTGCTTTTTCTAGAGCTACTGGAATTCCTGATAGGTTTA

GTGGGAGTGGGAGTGGAACAGATTTTACACTGACTATTTCTAGACTGGAACCAG

AAGATTTTGCAGTGTATTATTGTCAGCAGTATGGGTCTTCACCTTGGACTTTTGGT

CAGGGAACTAAAGTGGAAATTAAGAGAACTGTTGCTGCTCCTTCAGTTTTTATTT

TTCCACCTAGTGATGAGCAGCTGAAGAGTGGAACAGCATCTGTGGTGTGTCTTTT

GAATAATTTTTATCCTAGAGAAGCTAAGGTGCAGTGGAAAGTGGATAATGCATT

GCAGAGTGGAAATTCACAAGAATCAGTGACTGAGCAGGATTCAAAAGATAGTAC

ATATAGTCTTTCATCTACTTTGACACTGTCTAAGGCTGATTATGAGAAGCATAAA

GTGTATGCATGTGAGGTGACACATCAGGGGCTGTCTTCACCTGTGACAAAGTCTTTTAATA

GAGGGGAGTGTTGAACCTGA*GCTAGC* hIL-12-pembrolizumab (NotI-NheI)

>SEQ ID NO: 14

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

-continued
GTCTTCACAGACAAGACCTCAGCCACAGTCATCTGCAGGAAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

GAGAGGATCCTCTGGAAGTGGAGCTACTAACTTCAGCCTGCTGAAGCAGGCTGG

AGATGTGGAGGAGAACCCTGGACCTATGGAGTTTGGGCTGAGCTGGGTTTTCCTT

GTTGCTCTTTTAAGAGGTGTCCAGTGTCAGGTGCAGTTGGTGCAGTCTGGAGTTG

AAGTGAAAAAGCCTGGTGCTTCAGTGAAGGTGAGTTGTAAGGCTTCAGGGTATA

CATTTACTAATTATTATATGTATTGGGTGAGACAGGCTCCTGGTCAGGGACTTGA

GTGGATGGGTGGAATTAATCCTTCTAATGGTGGAACTAATTTTAATGAGAAGTTT

AAGAATAGAGTGACTCTGACTACAGATAGTTCTACTACTACTGCTTATATGGAGC

TGAAGTCTCTGCAGTTTGATGATACAGCTGTGTATTATTGTGCTAGAAGAGATTA

TAGATTTGATATGGGATTTGATTATTGGGGTCAGGGGACAACAGTTACAGTTAGT

TCAGCTTCTACTAAAGGACCATCAGTTTTTCCTCTGGCACCATGTTCTAGGAGTA

CATCAGAGTCTACTGCTGCACTTGGGTGTTTGGTGAAAGATTATTTTCCAGAACC

TGTTACAGTGAGTTGGAATAGTGGAGCTCTGACATCAGGGGTTCATACTTTTCCT

GCTGTGTTGCAGTCATCTGGGCTGTATTCTCTGTCATCTGTTGTGACAGTGCCAAG

TAGTTCATTGGGAACTAAAACTTATACATGTAATGTGGATCATAAGCCTTCTAAT

ACTAAAGTGGATAAGAGGGTGGAATCTAAGTATGGACCACCATGTCCTCCATGT

CCAGCACCTGAATTTCTGGGAGGACCATCTGTGTTTTTGTTTCCACCAAAACCAA

AAGATACATTGATGATTTCAAGGACACCAGAGGTGACATGTGTGGTGGTGGATG

TGAGTCAGGAAGATCCTGAAGTGCAATTTAATTGGTATGTGGATGGAGTGGAGG

TTCATAATGCTAAAACTAAGCCTAGGGAAGAGCAGTTTAATAGTACATATAGGG

TGGTGTCTGTGCTTACAGTTCTGCATCAAGATTGGCTGAATGGAAAAGAGTATAA

GTGTAAAGTTAGTAATAAAGGGCTGCCTTCTTCAATTGAGAAAACAATTAGTAAG

GCAAAGGGTCAGCCTAGAGAGCCTCAAGTTTATACATTGCCACCTTCTCAGGAA

GAGATGACAAAGAATCAGGTGTCTCTGACATGTTTGGTTAAGGGTTTTTATCCAT

CAGATATTGCTGTGGAGTGGGAGTCAAATGGTCAACCAGAGAATAATTATAAAA

CTACACCACCAGTGCTGGATTCAGATGGGTCATTTTTTCTGTATAGTAGACTGAC

TGTGGATAAATCAAGGTGGCAGGAGGGAAATGTGTTTTCTTGTTCTGTGATGCAT

GAAGCTCTGCATAATCATTATACACAGAAATCATTGAGTCTGTCATTGGGTAAGA

-continued

GAAGGAAGAGGGGAAGTGGAGAGGGCAGAGGAAGTCTGCTAACATGTGGTGAT

GTGGAGGAGAATCCTGGACCTATGGACATGAGGGTCCCTGCTCAGCTCCTGGGG

CTCCTGCTGCTCTGGCTCTCAGGTGCCAGATGTGAAATTGTGCTGACTCAGAGTC

CTGCTACACTGTCATTGAGTCCAGGGGAAAGAGCAACACTGTCTTGTAGGGCAA

GTAAGGGAGTTTCAACTTCTGGTTATTCATATCTGCATTGGTATCAGCAGAAACC

AGGGCAGGCACCTAGGTTGCTGATTTATCTGGCATCATATTTGGAGAGTGGGGTT

CCTGCAAGATTTTCTGGATCTGGGTCAGGAACAGATTTTACACTGACAATTTCAA

GTCTTGAGCCTGAGGATTTTGCAGTTTATTATTGTCAGCATTCAAGAGATCTGCCT

CTGACTTTTGGAGGAGGTACAAAGGTTGAGATTAAAAGAACTGTGGCAGCACCT

TCAGTGTTTATTTTTCCTCCTAGTGATGAGCAATTGAAAAGTGGTACAGCATCTGT

TGTGTGTCTGCTTAATAATTTTTATCCTAGAGAGGCAAAAGTTCAGTGGAAGGTT

GATAATGCATTGCAATCTGGGAATTCTCAAGAGAGTGTTACAGAACAGGATTCA

AAAGATTCTACTTATTCACTGTCATCAACTCTGACACTGTCAAAGGCAGATTATG

AGAAGCATAAAGTGTATGCTTGTGAGGTGACTCATCAAGGGCTTAGTTCTCCTGTTACTAA

AAGTTTTAATAGAGGTGAGTGTTGAACCTGA*GCTAGC* hIL12-nivolumab (NotI-NheI)

>SEQ ID NO: 15

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

-continued

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

GAGAGGATCCTCTGGAAGTGGAGCTACTAACTTCAGCCTGCTGAAGCAGGCTGG

AGATGTGGAGGAGAACCCTGGACCTATGGAGTTTGGGCTGAGCTGGGTTTTCCTT

GTTGCTCTTTTAAGAGGTGTCCAGTGTCAGGTGCAGCTGGTGGAGAGTGGTGGGG

GGGTGGTGCAACCTGGGAGGAGTCTGAGACTGGATTGTAAGGCTAGTGGGATTA

CTTTTTCAAATAGTGGAATGCATTGGGTGAGACAGGCTCCTGGGAAGGGGCTTGA

GTGGGTTGCTGTGATTTGGTATGATGGGTCTAAAAGGTATTATGCTGATAGTGTG

AAGGGTAGATTTACAATTTCTAGGGATAATAGTAAAAATACTCTGTTTCTTCAGA

TGAATTCTTTGAGAGCAGAGGATACAGCAGTTTATTATTGTGCAACAAATGATGA

TTATTGGGGGCAGGGTACTCTGGTTACTGTGTCTTCTGCTTCTACAAAGGGGCCA

TCAGTGTTTCCTCTGGCACCTTGTAGTAGATCAACTAGTGAGAGTACAGCTGCTC

TGGGGTGTCTTGTGAAAGATTATTTTCCTGAACCTGTGACTGTGTCTTGGAATTCT

GGAGCACTTACTTCAGGTGTTCATACATTTCCAGCAGTGCTGCAGAGTTCTGGGC

TGTATAGTCTGTCTTCAGTGGTGACAGTGCCTTCATCAAGTCTGGGAACAAAAAC

TTATACATGTAATGTGGATCATAAGCCATCAAATACTAAGGTGGATAAGAGAGT

GGAATCTAAGTATGGTCCACCATGTCCTCCTTGTCCAGCTCCTGAATTTCTGGGG

GGACCTAGTGTGTTTTTGTTTCCACCTAAGCCTAAGGATACACTTATGATTTCAAG

AACTCCTGAGGTTACTTGTGTGGTGGTGGATGTGTCTCAGGAAGATCCAGAAGTG

CAATTTAATTGGTATGTGGATGGGGTTGAAGTGCATAATGCAAAAACAAAACCA

AGGGAGGAGCAGTTTAATTCTACTTATAGGGTGGTGTCTGTGCTTACAGTGCTGC

ATCAAGATTGGTTGAATGGGAAAGAATATAAGTGTAAGGTTTCTAATAAGGGGT

TGCCTTCTAGTATTGAGAAGACTATTTCTAAGGCAAAGGGGCAGCCTAGAGAAC

CTCAAGTTTATACACTTCCTCCAAGTCAGGAGGAGATGACTAAAAATCAGGTTTC

ACTGACATGTCTGGTGAAAGGATTTTATCCATCAGATATTGCAGTTGAGTGGGAA

TCTAATGGGCAGCCTGAGAATAATTATAAGACTACACCACCTGTGCTTGATTCTG

ATGGAAGTTTTTTTCTGTATAGTAGACTGACAGTGGATAAAAGTAGATGGCAGGA

AGGTAATGTGTTTTCTTGTTCTGTGATGCATGAGGCACTGCATAATCATTATACTC

AAAAGAGTCTGTCTCTGTCTCTTGGAAAGAGAAGGAAGAGGGGAAGTGGAGAGG

GCAGAGGAAGTCTGCTAACATGTGGTGATGTGGAGGAGAATCCTGGACCTATGG

ACATGAGGGTCCCTGCTCAGCTCCTGGGGCTCCTGCTGCTCTGGCTCTCAGGTGC

CAGATGTGAGATTGTGCTGACACAGTCTCCTGCAACTCTGTCTCTGTCACCTGGG

GAGAGGGCTACTCTGTCATGTAGGGCTAGTCAGTCTGTGTCATCATATCTGGCAT

GGTATCAGCAAAAACCAGGTCAAGCTCCAAGGCTGCTGATTTATGATGCATCAA

ATAGGGCAACTGGTATTCCAGCAAGGTTTTCTGGGTCAGGAAGTGGAACAGATTT

TACACTGACTATTAGTTCTCTGGAGCCAGAGGATTTTGCAGTGTATTATTGTCAA

-continued

CAGAGTTCTAATTGGCCAAGAACATTTGGGCAGGGTACAAAAGTGGAGATTAAA

AGGACAGTGGCTGCTCCTTCTGTGTTTATTTTTCCACCTTCAGATGAACAACTTAA

AAGTGGTACAGCATCAGTGGTGTGTCTGTTGAATAATTTTTATCCAAGGGAAGCT

AAAGTTCAGTGGAAAGTTGATAATGCACTGCAGTCTGGGAATTCTCAGGAATCTG

TTACAGAACAGGATTCAAAAGATTCAACTTATTCTCTTTCTAGTACTCTGACATTG

TCTAAGGCTGATTATGAAAAGCATAAGGTGTATGCTTGTGAGGTGACACATCAG

GGACTTAGTTCACCAGTGACTAAATCTTTTAATAGGGGAGAGTGTTGAACCTGAG

*CTAGC* hIL12-bevacizumab (NotI-NheI)

>SEQ ID NO: 16

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

-continued

GAGAGGATCCTCTGGAAGTGGAGCTACTAACTTCAGCCTGCTGAAGCAGGCTGG

AGATGTGGAGGAGAACCCTGGACCTATGGAGTTTGGGCTGAGCTGGGTTTTCCTT

GTTGCTCTTTTAAGAGGTGTCCAGTGTGAAGTGCAGCTTGTGGAGTCAGGAGGGG

GGCTGGTGCAGCCTGGGGGGAGTCTGAGGCTGAGTTGTGCAGCAAGTGGTTATA

CTTTTACAAATTATGGAATGAATTGGGTGAGACAGGCTCCTGGTAAAGGGCTGG

AGTGGGTTGGGTGGATTAATACTTATACAGGGGAGCCAACATATGCTGCAGATTT

TAAAAGGAGGTTTACTTTTAGTCTGGATACATCTAAGTCAACAGCTTATCTTCAG

ATGAATTCTCTTAGGGCTGAGGATACAGCTGTTTATTATTGTGCAAAGTATCCTC

ATTATTATGGATCATCTCATTGGTATTTTGATGTGTGGGGTCAGGGAACACTGGT

GACTGTTAGTAGTGCTAGTACTAAAGGGCCTTCAGTGTTTCCACTTGCTCCATCA

AGTAAGTCAACATCTGGAGGGACTGCTGCACTGGGGTGTTTGGTGAAGGATTATT

TTCCAGAACCAGTGACTGTTTCTTGGAATTCTGGAGCACTTACTTCTGGTGTGCAT

ACATTTCCTGCAGTGTTGCAGTCATCAGGATTGTATTCACTGTCTTCTGTGGTGAC

TGTGCCATCAAGTTCACTGGGAACACAGACATATATTTGTAATGTTAATCATAAA

CCTTCTAATACAAAGGTGGATAAGAAGGTGGAACCTAAATCTTGTGATAAAACA

CATACTTGTCCACCTTGTCCAGCTCCAGAACTGCTTGGGGGTCCATCTGTGTTTCT

TTTTCCTCCTAAGCCTAAAGATACACTTATGATTTCTAGAACACCAGAAGTTACT

TGTGTGGTGGTGGATGTGAGTCATGAGGACCCAGAAGTTAAGTTTAATTGGTATG

TGGATGGGGTTGAAGTGCATAATGCTAAAACAAAGCCTAGAGAAGAACAGTATA

ATAGTACATATAGAGTGGTGTCTGTGCTGACTGTGCTGCATCAGGATTGGCTGAA

TGGAAAGGAATATAAATGTAAGGTGAGTAATAAAGCTCTTCCAGCTCCTATTGA

GAAGACAATTTCTAAGGCTAAGGGGCAACCAAGGGAACCACAAGTGTATACATT

GCCACCTTCAAGGGAGGAGATGACTAAGAATCAGGTGTCTCTGACTTGTCTTGTT

AAAGGGTTTTATCCTAGTGATATTGCTGTGGAGTGGGAGTCAAATGGACAGCCA

GAAAATAATTATAAAACAACACCACCTGTGCTGGATAGTGATGGAAGTTTTTTTC

TGTATTCTAAGCTGACAGTGGATAAGAGTAGATGGCAGCAGGGTAATGTGTTTA

GTTGTAGTGTTATGCATGAAGCACTGCATAATCATTATACACAGAAATCTCTTTC

TCTGTCACCAGGGAAAAGAAGGAAGAGGGGAAGTGGAGAGGGCAGAGGAAGTC

TGCTAACATGTGGTGATGTGGAGGAGAATCCTGGACCTATGGACATGAGGGTCC

CTGCTCAGCTCCTGGGGCTCCTGCTGCTCTGGCTCTCAGGTGCCAGATGTGATAT

TCAGATGACACAGTCACCAAGTTCTCTTAGTGCTTCTGTGGGGGATAGAGTTACA

ATTACTTGTTCAGCAAGTCAGGATATTAGTAATTATCTTAATTGGTATCAGCAGA

AGCCTGGAAAGGCTCCTAAGGTGTTGATTTATTTTACTAGTTCACTGCATTCTGGT

GTTCCTAGTAGGTTTAGTGGGTCTGGATCAGGAACAGATTTTACACTGACAATTT

CATCACTGCAGCCTGAAGATTTTGCTACTTATTATTGTCAGCAGTATAGTACTGTT

CCTTGGACATTTGGGCAGGGTACAAAGGTGGAGATTAAAAGAACTGTGGCTGCA

CCTAGTGTTTTTATTTTTCCTCCTTCAGATGAGCAGCTGAAATCTGGTACAGCATC

TGTTGTTTGTCTGCTTAATAATTTTTATCCTAGGGAGGCAAAGGTGCAATGGAAG

GTGGATAATGCACTGCAGAGTGGAAATTCTCAAGAATCAGTGACTGAGCAAGAT

TCTAAAGATTCAACTTATTCTCTGAGTTCAACTCTTACTCTGTCTAAGGCTGATTA

-continued

TGAAAAACATAAGGTTTATGCTTGTGAGGTGACTCATCAAGGACTTAGTAGTCCTGTGACA

AAGAGTTTTAATAGGGGGGAGTGTTGAACCTGA*GCTAGC* hIL12-blinatumomab (NotI-NheI)

>SEQ ID NO: 17

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

GAGAGGATCCTCTGGAAGTGGAGCTACTAACTTCAGCCTGCTGAAGCAGGCTGG

AGATGTGGAGGAGAACCCTGGACCTATGGACATGAGGGTCCCTGCTCAGCTCCT

GGGGCTCCTGCTGCTCTGGCTCTCAGGTGCCAGATGTGATATTCAGCTGACACAG

AGTCCTGCAAGTCTGGCTGTTAGTCTGGGGCAAAGAGCAACAATTAGTTGTAAG

GCTTCTCAGTCAGTGGATTATGATGGAGATAGTTATCTGAATTGGTATCAGCAGA

TTCCTGGGCAGCCTCCTAAGCTTCTGATTTATGATGCATCAAATCTTGTGTCAGG

AATTCCACCAAGGTTTTCTGGATCTGGAAGTGGAACTGATTTTACTCTGAATATT

-continued

CATCCTGTGGAAAAAGTGGATGCTGCAACATATCATTGTCAGCAGTCAACTGAG

GACCCTTGGACATTTGGAGGGGGGACAAAGCTTGAGATTAAGGGGGGGGGAGG

ATCAGGAGGGGGAGGTTCTGGAGGGGGAGGATCTCAGGTGCAGCTGCAGCAGTC

TGGGGCTGAGCTTGTTAGACCAGGATCTTCTGTGAAAATTTCATGTAAAGCATCA

GGGTATGCTTTTAGTTCTTATTGGATGAATTGGGTGAAACAGAGGCCTGGTCAGG

GACTGGAGTGGATTGGACAGATTTGGCCTGGGGATGGTGATACTAATTATAATG

GAAAGTTTAAAGGAAAAGCTACACTGACAGCAGATGAGTCTTCATCTACTGCAT

ATATGCAGCTTAGTTCTCTGGCAAGTGAGGATTCAGCAGTGTATTTTTGTGCAAG

AAGGGAGACTACAACAGTGGGAAGATATTATTATGCTATGGATTATTGGGGACA

AGGAACAACTGTGACAGTGTCTTCTGGGGGGGGTGGGTCTGATATTAAACTTCAG

CAATCAGGAGCAGAGCTTGCAAGGCCAGGTGCTTCAGTGAAAATGTCATGTAAG

ACTAGTGGGTATACATTTACTAGGTATACTATGCATTGGGTGAAACAAAGACCAG

GACAGGGGCTTGAGTGGATTGGATATATTAATCCAAGTAGGGGATATACAAATT

ATAATCAAAAGTTTAAAGATAAGGCTACTCTGACTACTGATAAGTCAAGTTCTAC

TGCTTATATGCAGCTTTCTTCTTTGACTTCAGAGGATTCAGCAGTGTATTATTGTG

CAAGATATTATGATGATCATTATTGTCTGGATTATTGGGGACAAGGAACAACACT

GACTGTGTCTTCTGTGGAGGGAGGGAGTGGAGGATCAGGTGGGTCAGGAGGTAG

TGGAGGGGTGGATGATATTCAACTGACACAGTCTCCAGCTATTATGAGTGCATCA

CCAGGGGAGAAGGTGACAATGACTTGTAGAGCATCAAGTTCTGTTTCTTATATGA

ATTGGTATCAGCAGAAGTCTGGGACAAGTCCTAAAAGATGGATTTATGATACTTC

TAAAGTGGCATCTGGAGTGCCTTATAGGTTTAGTGGATCTGGATCTGGAACATCT

TATTCATTGACTATTAGTAGTATGGAAGCAGAAGATGCAGCAACTTATTATTGTC

AGCAGTGGTCATCAAATCCTCTTACATTTGGAGCTGGGACTAAGTTGGAATTGAAACATCA

TCATCATCATCATTGAACCTGA*GCTAGC* hIL12-ranibizumab (NotI-NheI)

>SEQ ID NO: 18

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

-continued

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

GAGAGGATCCTCTGGAAGTGGAGCTACTAACTTCAGCCTGCTGAAGCAGGCTGG

AGATGTGGAGGAGAACCCTGGACCTATGGAGTTTGGGCTGAGCTGGGTTTTCCTT

GTTGCTCTTTTAAGAGGTGTCCAGTGTGAAGTGCAGCTTGTGGAGTCAGGAGGGG

GGCTGGTGCAGCCTGGGGGGAGTCTGAGGCTGAGTTGTGCAGCAAGTGGTTATA

CTTTTACAAATTATGGAATGAATTGGGTGAGACAGGCTCCTGGTAAAGGGCTGG

AGTGGGTTGGGTGGATTAATACTTATACAGGGGAGCCAACATATGCTGCAGATTT

TAAAAGGAGGTTTACTTTTAGTCTGGATACATCTAAGTCAACAGCTTATCTTCAG

ATGAATTCTCTTAGGGCTGAGGATACAGCTGTTTATTATTGTGCAAAGTATCCTC

ATTATTATGGATCATCTCATTGGTATTTTGATGTGTGGGGTCAGGGAACACTGGT

GACTGTTAGTAGTGCTAGTACTAAAGGGCCTTCAGTGTTTCCACTTGCTCCATCA

AGTAAGTCAACATCTGGAGGGACTGCTGCACTGGGGTGTTTGGTGAAGGATTATT

TTCCAGAACCAGTGACTGTTTCTTGGAATTCTGGAGCACTTACTTCTGGTGTGCAT

ACATTTCCTGCAGTGTTGCAGTCATCAGGATTGTATTCACTGTCTTCTGTGGTGAC

TGTGCCATCAAGTTCACTGGGAACACAGACATATATTTGTAATGTTAATCATAAA

CCTTCTAATACAAAGGTGGATAAGAAGGTGGAACCTAAATCTTGTGATAAAACA

CATACTCTGAGAAGGAAGAGGGGAAGTGGAGAGGGCAGAGGAAGTCTGCTAAC

ATGTGGTGATGTGGAGGAGAATCCTGGACCTATGGACATGAGGGTCCCTGCTCA

GCTCCTGGGGCTCCTGCTGCTCTGGCTCTCAGGTGCCAGATGTGATATTCAGCTG

ACACAGTCACCAAGTTCTCTTAGTGCTTCTGTGGGGGATAGAGTTACAATTACTT

GTTCAGCAAGTCAGGATATTAGTAATTATCTTAATTGGTATCAGCAGAAGCCTGG

AAAGGCTCCTAAGGTGTTGATTTATTTTACTAGTTCACTGCATTCTGGTGTTCCTA

GTAGGTTTAGTGGGTCTGGATCAGGAACAGATTTTACACTGACAATTTCATCACT

GCAGCCTGAAGATTTTGCTACTTATTATTGTCAGCAGTATAGTACTGTTCCTTGGA

CATTTGGGCAGGGTACAAAGGTGGAGATTAAAAGAACTGTGGCTGCACCTAGTG

TTTTTATTTTTCCTCCTTCAGATGAGCAGCTGAAATCTGGTACAGCATCTGTTGTT

-continued

TGTCTGCTTAATAATTTTTATCCTAGGGAGGCAAAGGTGCAATGGAAGGTGGATA

ATGCACTGCAGAGTGGAAATTCTCAAGAATCAGTGACTGAGCAAGATTCTAAAG

ATTCAACTTATTCTCTGAGTTCAACTCTTACTCTGTCTAAGGCTGATTATGAAAAA

CATAAGGTTTATGCTTGTGAGGTGACTCATCAAGGACTTAGTAGTCCTGTGACAAAGAGTT

TTAATAGGGGGGAGTGTTGAACCTGA*GCTAGC* mIL12-iTME (HindIII-NheI)

>SEQ ID NO: 19

*AAGCTT*GGCATTCCGGTACTGTTGGTAAAGCCACCATGTGTCCTCAGAAGCTCAC

CATCTCCTGGTTTGCCATTGTTTTGCTGGTGTCTCCACTCATGGCCATGTGGGAGC

TGGAGAAAGATGTTTATGTTGTGGAGGTGGACTGGACTCCTGATGCCCCTGGAGA

AACAGTGAACCTCACCTGTGACACCCCTGAAGAAGATGACATCACCTGGACCTC

AGACCAGAGACATGGAGTCATAGGCTCTGGAAAGACCCTGACCATCACTGTCAA

AGAGTTTCTGGATGCTGGCCAGTACACCTGCCACAAAGGAGGGGAGACTCTGAG

CCACTCACATCTGCTGCTCCACAAGAAGGAAAATGGAATTTGGTCCACTGAAATT

CTGAAAAATTTCAAAAACAAGACTTTCCTGAAGTGTGAAGCACCAAATTACTCTG

GAAGGTTCACCTGCTCATGGCTGGTGCAAAGAAACATGGACTTGAAGTTCAACA

TCAAGAGCAGTAGCAGTTCCCCTGACTCTAGGGCAGTGACATGTGGAATGGCCT

CTCTGTCTGCAGAGAAGGTCACACTGGACCAAAGGGACTATGAGAAGTATTCAG

TGTCCTGCCAGGAGGATGTCACCTGCCCAACTGCTGAGGAGACCCTGCCCATTGA

ACTGGCCTTGGAAGCAAGGCAGCAGAATAAATATGAGAACTACAGCACCAGCTT

CTTCATCAGGGACATCATCAAACCAGACCCTCCCAAGAACTTGCAGATGAAGCC

TTTGAAGAACTCACAGGTGGAGGTCAGCTGGGAGTACCCTGACTCCTGGAGCAC

TCCCCATTCCTACTTCTCCCTCAAGTTCTTTGTTAGAATCCAGAGGAAGAAAGAA

AAGATGAAGGAGACAGAGGAGGGGTGTAACCAGAAAGGTGCCTTCCTGGTGGA

GAAGACATCTACAGAAGTCCAATGCAAAGGAGGGAATGTCTGTGTGCAAGCTCA

GGATAGGTATTACAATTCCTCATGCAGCAAGTGGGCATGTGTTCCCTGCAGGGTC

AGATCTGGTGGAGGTGGAAGTGGAGGTGGTGGATCTGGGGGTGGAGGCAGCAG

GGTCATTCCAGTCTCTGGACCTGCCAGGTGTCTTAGCCAGTCCAGAAACCTGCTG

AAGACCACAGATGACATGGTGAAGACTGCCAGAGAAAAACTGAAACATTATTCC

TGCACTGCTGAAGACATTGATCATGAAGACATCACAAGGGACCAAACCAGCACA

TTGAAGACCTGTCTGCCACTGGAACTGCACAAGAATGAGAGTTGCCTGGCTACTA

GAGAGACTTCTTCCACAACAAGAGGGAGCTGCCTGCCCCCACAGAAGACCTCTT

TGATGATGACCCTGTGCCTTGGTAGCATCTATGAGGACTTGAAGATGTACCAGAC

AGAGTTCCAGGCCATCAATGCAGCACTTCAGAATCACAACCATCAGCAGATCAT

TCTGGACAAGGGCATGCTGGTGGCCATTGATGAGCTGATGCAGTCTCTGAATCAT

AATGGAGAGACTCTGAGACAGAAACCTCCTGTGGGAGAAGCAGACCCTTACAGA

GTGAAAATGAAGCTCTGCATCCTGCTTCATGCCTTCAGCACCAGAGTGGTGACCA

TCAACAGGGTGATGGGCTATCTGAGCTCTGCCAGAAGGAAGAGGGGATCCTCTG

GAAGTGGAGCTACTAACTTCAGCCTGCTGAAGCAGGCTGGAGATGTGGAGGAGA

ACCCTGGACCTATGATGGTGTTAAGTCTTCTGTACCTGTTGACAGCCCTTCCTGGT

ATCCTGTCAGAGGTGCAGCTGCAGGAGTCAGGACCAGGCCTGGTGAAACCTTCT

-continued

CAGAGTCTGTCCCTGACTTGTTCTGTCACTGGGTATTCAATTACATCTTCATATAG

ATGGAACTGGATCAGGAAGTTTCCAGGGAATAGGCTGGAGTGGATGGGGTACAT

AAATTCAGCTGGTATTTCTAATTACAATCCATCTCTGAAGAGAAGAATCTCCATC

ACAAGAGACACATCCAAAAACCAGTTCTTTCTGCAGGTTAATTCTGTGACTACTG

AGGATGCTGCCACATATTACTGTGCAAGAAGTGATAATATGGGGACAACACCTT

TTACTTATTGGGGTCAAGGGACATTGGTGACTGTGAGTTCTGCATCAACAACAGC

ACCATCTGTCTATCCACTGGCCCCTGTGTGTGGAGATACAACTGGCTCCTCAGTG

ACTCTGGGATGCCTGGTCAAGGGTTATTTCCCTGAGCCAGTGACCTTGACCTGGA

ACTCTGGCTCCCTGTCCAGTGGTGTGCACACCTTCCCAGCTGTCCTGCAGTCTGA

CCTCTACACCCTCAGCAGCTCAGTGACTGTAACCTCTAGCACCTGGCCCAGCCAG

TCCATCACCTGCAATGTGGCCCACCCAGCAAGCAGCACCAAGGTGGACAAGAAA

ATTGAGCCCAGAGGGCCCACAATCAAGCCCTGTCCTCCATGCAAATGCCCAGCA

CCTAATGCAGCTGGTGGACCATCTGTCTTCATCTTCCCTCCAAAGATCAAGGATG

TACTCATGATCTCCCTGAGCCCCATAGTCACATGTGTGGTGGTGGATGTGAGTGA

GGATGACCCAGATGTCCAGATCAGCTGGTTTGTGAACAATGTGGAAGTACACAC

AGCTCAGACACAAACCCATAGAGAGGATTACAACAGTACTCTCAGGGTGGTCAG

TGCCCTCCCCATCCAGCACCAGGACTGGATGAGTGGCAAGGAGTTCAAATGCAA

GGTCAACAACAAAGACCTGGGGGCACCCATTGAGAGAACCATCTCAAAACCCAA

AGGGTCAGTAAGAGCTCCACAGGTATATGTCTTGCCTCCACCAGAAGAAGAGAT

GACTAAGAAACAGGTCACTCTGACCTGCATGGTCACAGACTTCATGCCTGAAGA

CATTTATGTGGAGTGGACCAACAATGGGAAAACAGAGCTGAACTACAAGAACAC

TGAACCAGTCCTGGACTCTGATGGTTCTTACTTCATGTACAGCAAGCTGAGAGTG

GAAAAGAAGAACTGGGTGGAAAGAAATAGCTACTCCTGTTCAGTGGTCCATGAG

GGTCTGCACAATCACCACACAACTAAGAGCTTCTCTAGGACTCCAAGAAGGAAG

AGGGGAAGTGGAGAGGGCAGAGGAAGTCTGCTAACATGTGGTGATGTGGAGGA

GAATCCTGGACCTATGAGGTGCCTAGCTGAGTTCCTGGGGCTGCTTGTGCTCTGG

ATTCCTGGAGCCATTGGGGATATTGTGATGACTCAGGGTACTCTGCCTAATCCTG

TGCCAAGTGGGGAGTCTGTGTCTATTACATGTAGGAGTTCAAAGAGTCTTCTTTA

TTCAGATGGAAAAACATATCTGAATTGGTATCTGCAGAGACCTGGGCAGAGTCC

TCAGCTGCTGATTTATTGGATGTCTACTAGGGCATCTGGGGTGTCTGATAGATTTT

CTGGTAGTGGTAGTGGTACAGATTTTACATTGAAGATTTCTGGGGTGGAGGCTGA

AGATGTGGGTATTTATTATTGTCAGCAAGGTCTGGAGTTTCCAACATTTGGGGGA

GGTACTAAGCTGGAGCTGAAGAGAACTGATGCTGCACCAACTGTATCCATCTTCC

CACCATCCAGTGAGCAGCTGACATCTGGAGGTGCCTCAGTTGTGTGCTTCCTGAA

CAACTTCTACCCCAAAGACATCAATGTCAAGTGGAAGATTGATGGCAGTGAAAG

ACAAAATGGGGTCCTGAACAGTTGGACTGATCAGGACAGCAAAGACAGCACCTA

CAGCATGAGCAGCACCCTCACCCTGACCAAGGATGAGTATGAAAGACATAACAG

CTATACCTGTGAGGCCACTCACAAGACATCAACTTCACCCATTGTCAAGAGCTTC

AACAGGAATGAGTGTTGAACCTGA*GCTAGC*

-continued mIL2-mIL12 (HindIII-NheI)

>SEQ ID NO: 20

*AAGCTT*GGCATTCCGGTACTGTTGGTAAAGCCACCATGTACAGCATGCAGCTGGC

CTCCTGTGTGACACTGACACTGGTGCTGCTGGTGAACTCTGCACCCACTTCAAGC

TCCACCTCAAGCTCTACAGCTGAAGCCCAGCAGCAGCAGCAGCAGCAGCAGCAG

CAGCAGCAGCACCTGGAGCAGCTGCTGATGGACCTGCAGGAGCTGCTGAGCAGG

ATGGAGAATTACAGGAACCTGAAACTCCCCAGGATGCTGACCTTCAAATTTTACT

TGCCCAAGCAGGCCACAGAACTGAAGGATCTGCAGTGCCTGGAAGATGAACTTG

GACCTCTGAGGCATGTGCTGGATCTGACTCAAAGCAAGAGCTTTCAACTGGAAG

ATGCTGAGAATTTCATCAGCAATATCAGAGTGACTGTGGTCAAACTGAAGGGCT

CTGACAACACATTTGAGTGCCAATTTGATGATGAGTCAGCCACTGTGGTGGACTT

TCTGAGGAGATGGATTGCCTTCTGTCAAAGCATCATCTCAACAAGCCCTCAAAGA

AGGAAGAGGGGAAGTGGAGAGGGCAGAGGAAGTCTGCTAACATGTGGTGATGT

GGAGGAGAATCCTGGACCTATGTGTCCTCAGAAGCTCACCATCTCCTGGTTTGCC

ATTGTTTTGCTGGTGTCTCCACTCATGGCCATGTGGGAGCTGGAGAAAGATGTTT

ATGTTGTGGAGGTGGACTGGACTCCTGATGCCCCTGGAGAAACAGTGAACCTCA

CCTGTGACACCCCTGAAGAAGATGACATCACCTGGACCTCAGACCAGAGACATG

GAGTCATAGGCTCTGGAAAGACCCTGACCATCACTGTCAAAGAGTTTCTGGATGC

TGGCCAGTACACCTGCCACAAAGGAGGGGAGACTCTGAGCCACTCACATCTGCT

GCTCCACAAGAAGGAAAATGGAATTTGGTCCACTGAAATTCTGAAAAATTTCAA

AAACAAGACTTTCCTGAAGTGTGAAGCACCAAATTACTCTGGAAGGTTCACCTGC

TCATGGCTGGTGCAAAGAAACATGGACTTGAAGTTCAACATCAAGAGCAGTAGC

AGTTCCCCTGACTCTAGGGCAGTGACATGTGGAATGGCCTCTCTGTCTGCAGAGA

AGGTCACACTGGACCAAAGGGACTATGAGAAGTATTCAGTGTCCTGCCAGGAGG

ATGTCACCTGCCCAACTGCTGAGGAGACCCTGCCCATTGAACTGGCCTTGGAAGC

AAGGCAGCAGAATAAATATGAGAACTACAGCACCAGCTTCTTCATCAGGGACAT

CATCAAACCAGACCCTCCCAAGAACTTGCAGATGAAGCCTTTGAAGAACTCACA

GGTGGAGGTCAGCTGGGAGTACCCTGACTCCTGGAGCACTCCCCATTCCTACTTC

TCCCTCAAGTTCTTTGTTAGAATCCAGAGGAAGAAAGAAAAGATGAAGGAGACA

GAGGAGGGGTGTAACCAGAAAGGTGCCTTCCTGGTGGAGAAGACATCTACAGAA

GTCCAATGCAAAGGAGGGAATGTCTGTGTGCAAGCTCAGGATAGGTATTACAAT

TCCTCATGCAGCAAGTGGGCATGTGTTCCCTGCAGGGTCAGATCTGGTGGAGGTG

GAAGTGGAGGTGGTGGATCTGGGGGTGGAGGCAGCAGGGTCATTCCAGTCTCTG

GACCTGCCAGGTGTCTTAGCCAGTCCAGAAACCTGCTGAAGACCACAGATGACA

TGGTGAAGACTGCCAGAGAAAAACTGAAACATTATTCCTGCACTGCTGAAGACA

TTGATCATGAAGACATCACAAGGGACCAAACCAGCACATTGAAGACCTGTCTGC

CACTGGAACTGCACAAGAATGAGAGTTGCCTGGCTACTAGAGAGACTTCTTCCA

CAACAAGAGGGAGCTGCCTGCCCCCACAGAAGACCTCTTTGATGATGACCCTGT

GCCTTGGTAGCATCTATGAGGACTTGAAGATGTACCAGACAGAGTTCCAGGCCA

TCAATGCAGCACTTCAGAATCACAACCATCAGCAGATCATTCTGGACAAGGGCA

TGCTGGTGGCCATTGATGAGCTGATGCAGTCTCTGAATCATAATGGAGAGACTCT

GAGACAGAAACCTCCTGTGGGAGAAGCAGACCCTTACAGAGTGAAAATGAAGCT

-continued

CTGCATCCTGCTTCATGCCTTCAGCACCAGAGTGGTGACCATCAACAGGGTGATG

GGCTATCTGAGCTCTGCCTAAACCTGA*GCTAGC* hIL12-durvalumab (NotI-NheI)

>SEQ ID NO: 21

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

GAGAGGATCCTCTGGAAGTGGAGCTACTAACTTCAGCCTGCTGAAGCAGGCTGG

AGATGTGGAGGAGAACCCTGGACCTATGGAGTTTGGGCTGAGCTGGGTTTTCCTT

GTTGCTCTTTTAAGAGGTGTCCAGTGTGAGGTGCAGCTGGTGGAAAGTGGGGGG

GGACTTGTGCAGCCTGGGGGGTCACTTAGGCTTTCATGTGCTGCTTCTGGGTTTA

CATTTAGTAGATATTGGATGAGTTGGGTGAGGCAGGCACCAGGTAAGGGGCTGG

AGTGGGTGGCTAATATTAAGCAAGATGGTTCTGAGAAGTATTATGTGGATTCTGT

-continued

TAAGGGTAGGTTTACAATTTCTAGGGATAATGCTAAGAATAGTCTGTATCTGCAG

ATGAATTCACTTAGAGCAGAGGATACTGCAGTGTATTATTGTGCTAGAGAAGGG

GGTTGGTTTGGTGAATTGGCATTTGATTATTGGGGACAGGGGACTCTGGTTACAG

TGTCATCAGCAAGTACTAAGGGGCCATCTGTTTTTCCTCTGGCTCCTTCATCAAA

GAGTACAAGTGGAGGTACAGCTGCTCTTGGTTGTCTTGTGAAGGATTATTTTCCT

GAGCCTGTGACTGTGTCATGGAATTCAGGGGCTCTGACTAGTGGAGTGCATACTT

TTCCTGCTGTGCTGCAGAGTAGTGGACTGTATAGTCTGAGTTCTGTGGTGACAGT

GCCATCATCTAGTCTGGGAACACAAACATATATTTGTAATGTGAATCATAAACCA

TCTAATACAAAGGTTGATAAGAGAGTGGAGCCTAAAAGTTGTGATAAGACACAT

ACATGTCCACCATGTCCTGCTCCTGAATTTGAAGGTGGTCCAAGTGTTTTTCTGTT

TCCTCCTAAGCCTAAGGATACTCTTATGATTTCAAGGACTCCAGAAGTGACTTGT

GTGGTGGTTGATGTTAGTCATGAAGATCCTGAGGTTAAATTTAATTGGTATGTGG

ATGGAGTTGAAGTGCATAATGCAAAGACAAAACCAAGGGAAGAGCAGTATAATT

CTACATATAGGGTGGTTTCAGTGTTGACAGTGCTGCATCAAGATTGGCTGAATGG

AAAGGAATATAAATGTAAGGTTTCTAATAAAGCTCTGCCTGCTAGTATTGAAAAG

ACAATTTCAAAAGCAAAAGGACAACCAAGGGAACCACAGGTTTATACACTTCCT

CCTAGTAGGGAAGAAATGACAAAGAATCAGGTTAGTCTGACATGTCTGGTGAAA

GGGTTTTATCCTTCTGATATTGCAGTGGAATGGGAGTCAAATGGGCAGCCTGAAA

ATAATTATAAGACAACTCCACCAGTTCTTGATTCAGATGGATCTTTTTTTCTGTAT

AGTAAGCTGACAGTGGATAAATCTAGGTGGCAGCAAGGTAATGTGTTTAGTTGT

AGTGTTATGCATGAAGCACTGCATAATCATTATACTCAAAAGTCACTGAGTCTGT

CACCAGGGAAAAGAAGGAAGAGGGGAAGTGGAGAGGGCAGAGGAAGTCTGCTA

ACATGTGGTGATGTGGAGGAGAATCCTGGACCTATGGACATGAGGGTCCCTGCT

CAGCTCCTGGGGCTCCTGCTGCTCTGGCTCTCAGGTGCCAGATGTGAGATTGTTC

TGACACAGTCTCCTGGAACACTGTCACTGTCACCAGGAGAGAGGGCAACACTGT

CATGTAGAGCAAGTCAGAGGGTGAGTAGTAGTTATCTGGCTTGGTATCAGCAGA

AACCAGGGCAGGCACCTAGATTGCTTATTTATGATGCTTCAAGTAGGGCTACAGG

GATTCCTGATAGATTTTCAGGGAGTGGGTCAGGGACAGATTTTACATTGACAATT

AGTAGGTTGGAGCCTGAGGATTTTGCTGTGTATTATTGTCAGCAGTATGGATCTT

TGC CTTGGACATTTGGTCAGGGGACAAAAGTGGAGATTAAGAGGACAGTGGCAG

CTCCATCTGTGTTTATTTTTCCTCCTAGTGATGAGCAGCTTAAATCTGGGACAGCT

TCAGTGGTGTGTTTGCTTAATAATTTTTATCCAAGGGAGGCAAAGGTGCAGTGGA

AGGTTGATAATGCATTGCAGAGTGGAAATTCTCAGGAGAGTGTGACAGAGCAGG

ATTCTAAAGATTCAACATATTCTCTGTCTAGTACACTGACTCTGTCTAAGGCTGAT

TATGAAAAGCATAAGGTGTATGCATGTGAGGTTACACATCAAGGGCTGTCTTCTC

CTGTGACAAAATCATTTAATAGAGGAGAATGTTGAACCTGA*GCTAGC* hIL12-atezolizumab (NotI-NheI)

>SEQ ID NO: 22

*GCGGCCGC*TCGAGATCTGCGATCTAAGTAAGCTTGGCATTCCGGTACTGTTGGTA

AAGCCACCATGTGTCACCAGCAGTTGGTCATCTCTTGGTTTTCCCTGGTTTTTCTG

GCATCTCCCCTGGTGGCCATCTGGGAACTGAAGAAAGATGTTTATGTGGTGGAAT

TGGATTGGTATCCTGATGCCCCTGGAGAAATGGTGGTCCTCACCTGTGACACCCC

-continued

TGAAGAAGATGGTATCACCTGGACCTTGGACCAGAGCAGTGAGGTCCTGGGCTC

TGGCAAAACCCTGACCATCCAAGTCAAAGAGTTTGGAGATGCTGGCCAGTACAC

CTGTCACAAAGGAGGGGAGGTTCTGAGCCATTCCCTCCTGCTGCTTCACAAAAAG

GAAGATGGAATTTGGTCCACTGATATTCTGAAGGACCAGAAAGAACCCAAAAAT

AAGACCTTTCTGAGATGTGAGGCCAAGAATTATTCTGGAAGATTCACCTGCTGGT

GGCTGACCACAATCAGTACTGATTTGACATTCAGTGTCAAAAGCAGCAGAGGCT

CTTCTGACCCCCAAGGGGTGACCTGTGGAGCTGCTACACTCTCTGCAGAGAGAGT

CAGAGGGGACAACAAGGAGTATGAGTACTCAGTGGAGTGCCAGGAGGACAGTG

CCTGCCCAGCTGCTGAGGAGAGTCTGCCCATTGAGGTCATGGTGGATGCTGTTCA

CAAGCTCAAGTATGAAAACTACACCAGCAGCTTCTTCATCAGGGACATCATCAA

ACCTGACCCACCCAAGAACTTGCAGCTGAAGCCACTGAAGAATTCTAGGCAGGT

GGAGGTCAGCTGGGAGTACCCTGACACCTGGAGTACTCCACATTCCTACTTCTCC

CTGACATTCTGTGTTCAGGTCCAGGGCAAGAGCAAGAGAGAAAAGAAAGATAGA

GTCTTCACAGACAAGACCTCAGCCACAGTCATCTGCAGGAAAAATGCCAGCATT

AGTGTGAGGGCCCAGGACAGATACTATAGCTCATCTTGGAGTGAATGGGCATCT

GTGCCCTGCAGTGGTGGAGGTGGAAGTGGAGGTGGTGGATCTGGGGGTGGAGGC

AGCAGAAACCTCCCTGTGGCCACTCCAGACCCAGGAATGTTCCCATGCCTTCACC

ACTCCCAAAACCTGCTGAGGGCTGTCAGCAACATGCTCCAGAAGGCCAGACAAA

CTCTGGAATTTTACCCTTGCACTTCTGAAGAGATTGATCATGAAGATATCACAAA

AGATAAAACCAGCACAGTGGAGGCCTGTCTGCCATTGGAACTCACCAAGAATGA

GAGTTGCCTGAATTCCAGAGAGACCTCTTTCATCACTAATGGGAGTTGCCTGGCC

TCCAGAAAGACCTCTTTTATGATGGCCCTGTGCCTTAGTAGTATTTATGAAGACTT

GAAGATGTACCAGGTGGAGTTCAAGACCATGAATGCAAAGCTTCTGATGGACCC

TAAGAGGCAGATCTTTCTGGATCAAAACATGCTGGCAGTTATTGATGAGCTGATG

CAGGCCCTGAATTTCAACAGTGAGACTGTGCCACAAAAATCCTCCCTTGAAGAA

CCTGATTTTTATAAAACTAAAATCAAGCTCTGCATCCTTCTTCATGCTTTCAGAAT

TAGGGCAGTGACTATTGACAGAGTGATGAGCTATCTGAATGCTTCCAGGAGAAA

GAGAGGATCCTCTGGAAGTGGAGCTACTAACTTCAGCCTGCTGAAGCAGGCTGG

AGATGTGGAGGAGAACCCTGGACCTATGGAGTTTGGGCTGAGCTGGGTTTTCCTT

GTTGCTCTTTTAAGAGGTGTCCAGTGTGAGGTGCAGCTTGTGGAATCTGGGGGGG

GGCTGGTGCAGCCTGGTGGTAGTCTGAGACTGTCATGTGCTGCTAGTGGGTTTAC

ATTTTCAGATTCTTGGATTCATTGGGTGAGACAGGCACCTGGGAAAGGTCTGGAG

TGGGTGGCATGGATTTCACCTTATGGGGGATCTACATATTATGCTGATAGTGTGA

AGGGGAGGTTTACAATTTCTGCTGATACATCTAAGAATACAGCTTATCTTCAGAT

GAATTCTCTGAGAGCTGAAGATACTGCAGTGTATTATTGTGCTAGGAGGCATTGG

CCTGGAGGGTTTGATTATTGGGGTCAAGGTACACTGGTGACTGTTAGTAGTGCTA

GTACTAAAGGTCCTTCTGTGTTTCCACTGGCACCAAGTTCAAAGAGTACATCAGG

AGGGACTGCAGCTCTGGGTTGTTTGGTGAAAGATTATTTTCCTGAACCTGTGACA

GTTTCATGGAATTCTGGAGCACTGACTTCTGGAGTGCATACATTTCCTGCTGTGCT

GCAGTCTAGTGGGTTGTATTCATTGTCAAGTGTGGTTACAGTGCCTTCAAGTTCTC

-continued

TGGGTACACAGACTTATATTTGTAATGTGAATCATAAGCCAAGTAATACAAAAGT
GGATAAGAAAGTTGAGCCTAAATCATGTGATAAAACTCATACTTGTCCACCTTGT
CCTGCTCCAGAGCTGTTGGGTGGGCCTAGTGTTTTTCTTTTTCCACCAAAGCCAA
AAGATACTTTGATGATTTCAAGGACACCAGAAGTGACATGTGTGGTTGTTGATGT
TTCTCATGAAGATCCTGAGGTGAAGTTTAATTGGTATGTTGATGGGGTTGAGGTG
CATAATGCTAAGACAAAACCTAGGGAGGAACAGTATGCTTCTACATATAGAGTT
GTGTCAGTGTTGACAGTGCTGCATCAAGATTGGCTTAATGGGAAAGAATATAAGT
GTAAGGTTTCAAATAAGGCATTGCCAGCTCCAATTGAAAAGACAATTTCTAAGG
CTAAGGGTCAGCCTAGGGAGCCACAGGTGTATACTCTGCCACCTTCAAGAGAGG
AAATGACTAAGAATCAGGTGTCATTGACATGTTTGGTGAAAGGATTTTATCCTTC
AGATATTGCTGTGGAATGGGAATCTAATGGACAACCAGAGAATAATTATAAAAC
TACTCCTCCTGTGCTGGATAGTGATGGAAGTTTTTTTCTGTATTCTAAACTTACTG
TTGATAAAAGTAGATGGCAGCAAGGTAATGTTTTTTCTTGTTCTGTGATGCATGA
AGCTCTTCATAATCATTATACTCAGAAGAGTCTGAGTCTGTCTCCTGGAAAGAGA
AGGAAGAGGGGAAGTGGAGAGGGCAGAGGAAGTCTGCTAACATGTGGTGATGT
GGAGGAGAATCCTGGACCTATGGACATGAGGGTCCCTGCTCAGCTCCTGGGGCT
CCTGCTGCTCTGGCTCTCAGGTGCCAGATGTGATATTCAGATGACACAGAGTCCA
AGTTCACTGTCAGCTTCTGTTGGTGATAGAGTTACTATTACATGTAGAGCTTCTCA
GGATGTGAGTACTGCAGTGGCTTGGTATCAGCAGAAGCCAGGGAAGGCTCCAAA
GCTGCTGATTTATTCAGCATCATTTCTGTATTCAGGGGTGCCATCAAGATTTTCAG
GTTCTGGAAGTGGAACAGATTTTACTCTGACTATTTCATCTCTGCAACCAGAAGA
TTTTGCAACATATTATTGTCAGCAGTATCTGTATCATCCAGCAACATTTGGTCAGG
GTACTAAAGTGGAAATTAAAAGGACAGTGGCAGCACCATCAGTTTTTATTTTTCC
ACCTAGTGATGAACAGCTGAAAAGTGGGACAGCTTCAGTGGTGTGTCTGCTTAAT
AATTTTTATCCTAGAGAAGCAAAAGTGCAGTGGAAGGTGGATAATGCACTGCAA
AGTGGGAATTCACAGGAATCAGTGACAGAGCAAGATTCTAAGGATTCTACATAT
AGTCTGTCTTCTACATTGACTCTGTCTAAGGCAGATTATGAAAAGCATAAAGTTT
ATGCATGTGAGGTTACTCATCAGGGATTGTCATCACCTGTTACTAAAAGTTTTAA
TAGGGGTGAGTGTTGAACCTGA*GCTAGC* iTME (HindIII-NheI)

>SEQ ID NO: 23

*AAGCTT*GGCATTCCGGTACTGTTGGTAAAGCCACCATGATGGTGTTAAGTCTTCT
GTACCTGTTGACAGCCCTTCCTGGTATCCTGTCAGAGGTGCAGCTGCAGGAGTCA
GGACCAGGCCTGGTGAAACCTTCTCAGAGTCTGTCCCTGACTTGTTCTGTCACTG
GGTATTCAATTACATCTTCATATAGATGGAACTGGATCAGGAAGTTTCCAGGGAA
TAGGCTGGAGTGGATGGGGTACATAAATTCAGCTGGTATTTCTAATTACAATCCA
TCTCTGAAGAGAAGAATCTCCATCACAAGAGACACATCCAAAAACCAGTTCTTTC
TGCAGGTTAATTCTGTGACTACTGAGGATGCTGCCACATATTACTGTGCAAGAAG
TGATAATATGGGGACAACACCTTTTACTTATTGGGGTCAAGGGACATTGGTGACT
GTGAGTTCTGCATCAACAACAGCACCATCTGTCTATCCACTGGCCCCTGTGTGTG
GAGATACAACTGGCTCCTCAGTGACTCTGGGATGCCTGGTCAAGGGTTATTTCCC
TGAGCCAGTGACCTTGACCTGGAACTCTGGCTCCCTGTCCAGTGGTGTGCACACC

-continued

TTCCCAGCTGTCCTGCAGTCTGACCTCTACACCCTCAGCAGCTCAGTGACTGTAA

CCTCTAGCACCTGGCCCAGCCAGTCCATCACCTGCAATGTGGCCCACCCAGCAAG

CAGCACCAAGGTGGACAAGAAAATTGAGCCCAGAGGGCCCACAATCAAGCCCTG

TCCTCCATGCAAATGCCCAGCACCTAATGCAGCTGGTGGACCATCTGTCTTCATC

TTCCCTCCAAAGATCAAGGATGTACTCATGATCTCCCTGAGCCCCATAGTCACAT

GTGTGGTGGTGGATGTGAGTGAGGATGACCCAGATGTCCAGATCAGCTGGTTTGT

GAACAATGTGGAAGTACACACAGCTCAGACACAAACCCATAGAGAGGATTACAA

CAGTACTCTCAGGGTGGTCAGTGCCCTCCCCATCCAGCACCAGGACTGGATGAGT

GGCAAGGAGTTCAAATGCAAGGTCAACAACAAAGACCTGGGGGCACCCATTGAG

AGAACCATCTCAAAACCCAAAGGGTCAGTAAGAGCTCCACAGGTATATGTCTTG

CCTCCACCAGAAGAAGAGATGACTAAGAAACAGGTCACTCTGACCTGCATGGTC

ACAGACTTCATGCCTGAAGACATTTATGTGGAGTGGACCAACAATGGGAAAACA

GAGCTGAACTACAAGAACACTGAACCAGTCCTGGACTCTGATGGTTCTTACTTCA

TGTACAGCAAGCTGAGAGTGGAAAAGAAGAACTGGGTGGAAAGAAATAGCTAC

TCCTGTTCAGTGGTCCATGAGGGTCTGCACAATCACCACACAACTAAGAGCTTCT

CTAGGACTCCAAGAAGGAAGAGGGGAAGTGGAGAGGGCAGAGGAAGTCTGCTA

ACATGTGGTGATGTGGAGGAGAATCCTGGACCTATGAGGTGCCTAGCTGAGTTC

CTGGGGCTGCTTGTGCTCTGGATTCCTGGAGCCATTGGGGATATTGTGATGACTC

AGGGTACTCTGCCTAATCCTGTGCCAAGTGGGGAGTCTGTGTCTATTACATGTAG

GAGTTCAAAGAGTCTTCTTTATTCAGATGGAAAAACATATCTGAATTGGTATCTG

CAGAGACCTGGGCAGAGTCCTCAGCTGCTGATTTATTGGATGTCTACTAGGGCAT

CTGGGGTGTCTGATAGATTTTCTGGTAGTGGTAGTGGTACAGATTTTACATTGAA

GATTTCTGGGGTGGAGGCTGAAGATGTGGGTATTTATTATTGTCAGCAAGGTCTG

GAGTTTCCAACATTTGGGGGAGGTACTAAGCTGGAGCTGAAGAGAACTGATGCT

GCACCAACTGTATCCATCTTCCCACCATCCAGTGAGCAGCTGACATCTGGAGGTG

CCTCAGTTGTGTGCTTCCTGAACAACTTCTACCCCAAAGACATCAATGTCAAGTG

GAAGATTGATGGCAGTGAAAGACAAAATGGGGTCCTGAACAGTTGGACTGATCA

GGACAGCAAAGACAGCACCTACAGCATGAGCAGCACCCTCACCCTGACCAAGGA

TGAGTATGAAAGACATAACAGCTATACCTGTGAGGCCACTCACAAGACATCAAC

TTCACCCATTGTCAAGAGCTTCAACAGGAATGAGTGTTGAACCTGA*GCTAGC*

MVFTT (HindIII-NheI)

>SEQ ID NO: 24

*AAGCTT*GGCATTCCGGTACTGTTGGTAAAGCCACCATGCTGTCTGAGATTAAGGG

AGTGATTGTGCATAGGCTGGAGGGGGTGCCTATGGGCCTGCCTAATTCTGTGGAT

GATGCTCTGATTAATAGCACTAAGATTTATTCATATTTTCCATCTGTGCCAATGGG

ACTGCCCCAGTATATTAAGGCTAATAGTAAATTTATTGGCATTACTGAACTGTGAACCT

GA*GCTAGC* mIL12-MVFTT (HindIII-NheI)

>SEQ ID NO: 25

*AAGCTT*GGCATTCCGGTACTGTTGGTAAAGCCACCATGTGTCCTCAGAAGCTCAC

CATCTCCTGGTTTGCCATTGTTTTGCTGGTGTCTCCACTCATGGCCATGTGGGAGC

TGGAGAAAGATGTTTATGTTGTGGAGGTGGACTGGACTCCTGATGCCCCTGGAGA

-continued

AACAGTGAACCTCACCTGTGACACCCCTGAAGAAGATGACATCACCTGGACCTC

AGACCAGAGACATGGAGTCATAGGCTCTGGAAAGACCCTGACCATCACTGTCAA

AGAGTTTCTGGATGCTGGCCAGTACACCTGCCACAAAGGAGGGGAGACTCTGAG

CCACTCACATCTGCTGCTCCACAAGAAGGAAAATGGAATTTGGTCCACTGAAATT

CTGAAAAATTTCAAAAACAAGACTTTCCTGAAGTGTGAAGCACCAAATTACTCTG

GAAGGTTCACCTGCTCATGGCTGGTGCAAAGAAACATGGACTTGAAGTTCAACA

TCAAGAGCAGTAGCAGTTCCCCTGACTCTAGGGCAGTGACATGTGGAATGGCCT

CTCTGTCTGCAGAGAAGGTCACACTGGACCAAAGGGACTATGAGAAGTATTCAG

TGTCCTGCCAGGAGGATGTCACCTGCCCAACTGCTGAGGAGACCCTGCCCATTGA

ACTGGCCTTGGAAGCAAGGCAGCAGAATAAATATGAGAACTACAGCACCAGCTT

CTTCATCAGGGACATCATCAAACCAGACCCTCCCAAGAACTTGCAGATGAAGCC

TTTGAAGAACTCACAGGTGGAGGTCAGCTGGGAGTACCCTGACTCCTGGAGCAC

TCCCCATTCCTACTTCTCCCTCAAGTTCTTTGTTAGAATCCAGAGGAAGAAAGAA

AAGATGAAGGAGACAGAGGAGGGGTGTAACCAGAAAGGTGCCTTCCTGGTGGA

GAAGACATCTACAGAAGTCCAATGCAAAGGAGGGAATGTCTGTGTGCAAGCTCA

GGATAGGTATTACAATTCCTCATGCAGCAAGTGGGCATGTGTTCCCTGCAGGGTC

AGATCTGGTGGAGGTGGAAGTGGAGGTGGTGGATCTGGGGGTGGAGGCAGCAG

GGTCATTCCAGTCTCTGGACCTGCCAGGTGTCTTAGCCAGTCCAGAAACCTGCTG

AAGACCACAGATGACATGGTGAAGACTGCCAGAGAAAAACTGAAACATTATTCC

TGCACTGCTGAAGACATTGATCATGAAGACATCACAAGGGACCAAACCAGCACA

TTGAAGACCTGTCTGCCACTGGAACTGCACAAGAATGAGAGTTGCCTGGCTACTA

GAGAGACTTCTTCCACAACAAGAGGGAGCTGCCTGCCCCCACAGAAGACCTCTT

TGATGATGACCCTGTGCCTTGGTAGCATCTATGAGGACTTGAAGATGTACCAGAC

AGAGTTCCAGGCCATCAATGCAGCACTTCAGAATCACAACCATCAGCAGATCAT

TCTGGACAAGGGCATGCTGGTGGCCATTGATGAGCTGATGCAGTCTCTGAATCAT

AATGGAGAGACTCTGAGACAGAAACCTCCTGTGGGAGAAGCAGACCCTTACAGA

GTGAAAATGAAGCTCTGCATCCTGCTTCATGCCTTCAGCACCAGAGTGGTGACCA

TCAACAGGGTGATGGGCTATCTGAGCTCTGCCAGAAGGAAGAGGGGATCCTCTG

GAAGTGGAGCTACTAACTTCAGCCTGCTGAAGCAGGCTGGAGATGTGGAGGAGA

ACCCTGGACCTATGCTGTCTGAGATTAAGGGAGTGATTGTGCATAGGCTGGAGG

GGGTGCCTATGGGCCTGCCTAATTCTGTGGATGATGCTCTGATTAATAGCACTAA

GATTTATTCATATTTTCCATCTGTGCCAATGGGACTGCCCCAGTATATTAAGGCTA

ATAGTAAATTTATTGGCATTACTGAACTGTGAACCTGA*GCTAGC*

EGFRv3 (HindIII-NheI)

>SEQ ID NO: 26

*AAGCTT*GGCATTCCGGTACTGTTGGTAAAGCCACCATGAGACCATCTGGAACTGC

TGGAGCTGCCTTGCTGGCCCTGCTGGCTGCCCTTTGTCCTGCCTCAAGAGCTCTG

GAGGAGAAAAAGGGAAATTATGTGGTGACTGATCATGGTTCTTCTGTGAGAGCA

TGTGGGGCTGATTCTTATGAGATGGAGGAGGATGGGGTGAGGAAATGTAAGAAG

TGTGAGGGTCCTTGTAGGAAAGTGTGTAATGGAATTGGAATTGGAGAATTTAAA

GATTCTCTGAGTATTAATGCTACAAATATTAAGCATTTTAAAAATTGTACTTCTAT

TTCTGGAGATCTGCATATTCTTCCTGTGGCTTTTAGAGGAGATAGTTTTACTCATA

-continued

CTCCTCCTCTGGACCCACAGGAACTGGATATTCTGAAAACAGTGAAGGAAATTA

CAGGGTTTCTTCTTATTCAAGCCTGGCCAGAGAATAGGACAGATCTGCATGCATT

TGAGAATCTGGAGATTATTAGAGGTAGGACAAAGCAGCATGGTCAGTTTTCACT

GGCAGTGGTGAGTCTGAATATTACATCTCTGGGGCTGAGATCACTGAAGGAAATT

TCAGATGGTGATGTGATTATTTCTGGAAATAAGAATCTTTGTTATGCTAATACTAT

TAATTGGAAAAAACTGTTTGGTACTTCTGGACAAAAGACTAAGATTATTTCAAAT

AGGGGAGAGAATTCTTGTAAAGCTACAGGACAAGTGTGTCATGCTTTGTGTTCAC

CAGAGGGGTGTTGGGGTCCTGAGCCAAGAGATTGTGTGTCATGTAGGAATGTGT

CTAGGGGAAGGGAATGTGTGGATAAGTGTAATCTTCTGGAAGGGGAACCAAGGG

AATTTGTGGAAAATTCTGAATGTATTCAGTGTCATCCTGAGTGTCTGCCACAGGC

TATGAATATTACTTGTACTGGTAGGGGACCTGATAATTGTATTCAATGTGCTCATT

ATATTGATGGTCCTCATTGTGTAAAAACATGTCCTGCTGGAGTGATGGGAGAAAA

TAATACTCTTGTGTGGAAATATGCTGATGCTGGACATGTGTGTCATCTGTGTCATC

CAAATTGTACATATGGATGTACAGGGCCTGGTCTGGAAGGATGTCCTACTAATGG

GCCTAAGATTCCAGCTGTGGGCCAGGACACCCAGGAGGTCATTGTGGTGCCACA

CTCCTTGCCCTTTAAGGTGGTGGTGATCTCAGCCATCCTGGCCCTGGTGGTGCTC

ACCATCATCTCCCTTATCATCCTCATCATGCTTTGGCAGAAGAAGCCAAGATGAA

CCTGA*AAGCTT*

HERd4 (NcoI-NheI)

>SEQ ID NO: 27

*CCATGG*AGCTGGCAGCTCTTTGTAGGTGGGGGCTTCTGCTTGCACTGCTTCCTCC

AGGAGCAGCTTCAGCTTGTCATCAACTGTGTGCTAGGGGGCATTGTTGGGGACCA

GGACCAACTCAGTGTGTGAATTGTTCACAGTTTCTGAGGGGGCAGGAGTGTGTGG

AGGAGTGTAGGGTGCTGCAAGGACTGCCCAGGGAATATGTTAATGCTAGGCATT

GTCTGCCATGTCATCCAGAATGTCAGCCACAGAATGGTTCTGTGACATGTTTTGG

ACCTGAAGCTGATCAGTGTGTGGCATGTGCACATTATAAGGACCCACCTTTTTGT

GTGGCAAGGTGTCCTAGTGGAGTGAAACCTGATCTGTCTTATATGCCAATTTGGA

AGTTTCCAGATGAGGAAGGGGCTTGTCAGCCTTGTCCTATCAATTGTACACATAG

TTGTGTGGATCTGGATGATAAGGGGTGTCCAGCAGAGCAAAGGGCTTCTCCACT

GACAGCTGTGGGCCAGGACACCCAGGAGGTCATTGTGGTGCCACACTCCTTGCC

CTTTAAGGTGGTGGTGATCTCAGCCATCCTGGCCCTGGTGGTGCTCACCATCATC

TCCCTTATCATCCTCATCATGCTTTGGCAGAAGAAGCCAAGATGAACCTGA*GCTA*

*GC* mIL12-EGFRv3 (HindIII-NheI)

>SEQ ID NO: 28

*AAGCTT*GGCATTCCGGTACTGTTGGTAAAGCCACCATGTGTCCTCAGAAGCTCAC

CATCTCCTGGTTTGCCATTGTTTTGCTGGTGTCTCCACTCATGGCCATGTGGGAGC

TGGAGAAAGATGTTTATGTTGTGGAGGTGGACTGGACTCCTGATGCCCCTGGAGA

AACAGTGAACCTCACCTGTGACACCCCTGAAGAAGATGACATCACCTGGACCTC

AGACCAGAGACATGGAGTCATAGGCTCTGGAAAGACCCTGACCATCACTGTCAA

AGAGTTTCTGGATGCTGGCCAGTACACCTGCCACAAAGGAGGGGAGACTCTGAG

CCACTCACATCTGCTGCTCCACAAGAAGGAAAATGGAATTTGGTCCACTGAAATT

-continued

CTGAAAAAATTTCAAAAACAAGACTTTCCTGAAGTGTGAAGCACCAAATTACTCTG

GAAGGTTCACCTGCTCATGGCTGGTGCAAAGAAACATGGACTTGAAGTTCAACA

TCAAGAGCAGTAGCAGTTCCCCTGACTCTAGGGCAGTGACATGTGGAATGGCCT

CTCTGTCTGCAGAGAAGGTCACACTGGACCAAAGGGACTATGAGAAGTATTCAG

TGTCCTGCCAGGAGGATGTCACCTGCCCAACTGCTGAGGAGACCCTGCCCATTGA

ACTGGCCTTGGAAGCAAGGCAGCAGAATAAATATGAGAACTACAGCACCAGCTT

CTTCATCAGGGACATCATCAAACCAGACCCTCCCAAGAACTTGCAGATGAAGCC

TTTGAAGAACTCACAGGTGGAGGTCAGCTGGGAGTACCCTGACTCCTGGAGCAC

TCCCCATTCCTACTTCTCCCTCAAGTTCTTTGTTAGAATCCAGAGGAAGAAAGAA

AAGATGAAGGAGACAGAGGAGGGGTGTAACCAGAAAGGTGCCTTCCTGGTGGA

GAAGACATCTACAGAAGTCCAATGCAAAGGAGGGAATGTCTGTGTGCAAGCTCA

GGATAGGTATTACAATTCCTCATGCAGCAAGTGGGCATGTGTTCCCTGCAGGGTC

AGATCTGGTGGAGGTGGAAGTGGAGGTGGTGGATCTGGGGGTGGAGGCAGCAG

GGTCATTCCAGTCTCTGGACCTGCCAGGTGTCTTAGCCAGTCCAGAAACCTGCTG

AAGACCACAGATGACATGGTGAAGACTGCCAGAGAAAAACTGAAACATTATTCC

TGCACTGCTGAAGACATTGATCATGAAGACATCACAAGGGACCAAACCAGCACA

TTGAAGACCTGTCTGCCACTGGAACTGCACAAGAATGAGAGTTGCCTGGCTACTA

GAGAGACTTCTTCCACAACAAGAGGGAGCTGCCTGCCCCCACAGAAGACCTCTT

TGATGATGACCCTGTGCCTTGGTAGCATCTATGAGGACTTGAAGATGTACCAGAC

AGAGTTCCAGGCCATCAATGCAGCACTTCAGAATCACAACCATCAGCAGATCAT

TCTGGACAAGGGCATGCTGGTGGCCATTGATGAGCTGATGCAGTCTCTGAATCAT

AATGGAGAGACTCTGAGACAGAAACCTCCTGTGGGAGAAGCAGACCCTTACAGA

GTGAAAATGAAGCTCTGCATCCTGCTTCATGCCTTCAGCACCAGAGTGGTGACCA

TCAACAGGGTGATGGGCTATCTGAGCTCTGCCAGAAGGAAGAGGGGATCCTCTG

GAAGTGGAGCTACTAACTTCAGCCTGCTGAAGCAGGCTGGAGATGTGGAGGAGA

ACCCTGGACCTATGAGACCATCTGGAACTGCTGGAGCTGCCTTGCTGGCCCTGCT

GGCTGCCCTTTGTCCTGCCTCAAGAGCTCTGGAGGAGAAAAAGGGAAATTATGT

GGTGACTGATCATGGTTCTTCTGTGAGAGCATGTGGGGCTGATTCTTATGAGATG

GAGGAGGATGGGGTGAGGAAATGTAAGAAGTGTGAGGGTCCTTGTAGGAAAGT

GTGTAATGGAATTGGAATTGGAGAATTTAAAGATTCTCTGAGTATTAATGCTACA

AATATTAAGCATTTTAAAAATTGTACTTCTATTTCTGGAGATCTGCATATTCTTCC

TGTGGCTTTTAGAGGAGATAGTTTTACTCATACTCCTCCTCTGGACCCACAGGAA

CTGGATATTCTGAAAACAGTGAAGGAAATTACAGGGTTTCTTCTTATTCAAGCCT

GGCCAGAGAATAGGACAGATCTGCATGCATTTGAGAATCTGGAGATTATTAGAG

GTAGGACAAAGCAGCATGGTCAGTTTTCACTGGCAGTGGTGAGTCTGAATATTAC

ATCTCTGGGGCTGAGATCACTGAAGGAAATTTCAGATGGTGATGTGATTATTTCT

GGAAATAAGAATCTTTGTTATGCTAATACTATTAATTGGAAAAAACTGTTTGGTA

CTTCTGGACAAAAGACTAAGATTATTTCAAATAGGGGAGAGAATTCTTGTAAAG

CTACAGGACAAGTGTGTCATGCTTTGTGTTCACCAGAGGGGTGTTGGGGTCCTGA

GCCAAGAGATTGTGTGTCATGTAGGAATGTGTCTAGGGGAAGGGAATGTGTGGA

TAAGTGTAATCTTCTGGAAGGGGAACCAAGGGAATTTGTGGAAAATTCTGAATG

-continued

TATTCAGTGTCATCCTGAGTGTCTGCCACAGGCTATGAATATTACTTGTACTGGTA

GGGGACCTGATAATTGTATTCAATGTGCTCATTATATTGATGGTCCTCATTGTGTA

AAAACATGTCCTGCTGGAGTGATGGGAGAAAATAATACTCTTGTGTGGAAATAT

GCTGATGCTGGACATGTGTGTCATCTGTGTCATCCAAATTGTACATATGGATGTA

CAGGGCCTGGTCTGGAAGGATGTCCTACTAATGGGCCTAAGATTCCAGCTGTGG

GCCAGGACACCCAGGAGGTCATTGTGGTGCCACACTCCTTGCCCTTTAAGGTGGT

GGTGATCTCAGCCATCCTGGCCCTGGTGGTGCTCACCATCATCTCCCTTATCATCC

TCATCATGCTTTGGCAGAAGAAGCCAAGATGAACCTGA*GCTAGC* mIL12-HERd4 (HindIII-NheI)

>SEQ ID NO: 29

*AAGCTT*GGCATTCCGGTACTGTTGGTAAAGCCACCATGTGTCCTCAGAAGCTCAC

CATCTCCTGGTTTGCCATTGTTTTGCTGGTGTCTCCACTCATGGCCATGTGGGAGC

TGGAGAAAGATGTTTATGTTGTGGAGGTGGACTGGACTCCTGATGCCCCTGGAGA

AACAGTGAACCTCACCTGTGACACCCCTGAAGAAGATGACATCACCTGGACCTC

AGACCAGAGACATGGAGTCATAGGCTCTGGAAAGACCCTGACCATCACTGTCAA

AGAGTTTCTGGATGCTGGCCAGTACACCTGCCACAAAGGAGGGGAGACTCTGAG

CCACTCACATCTGCTGCTCCACAAGAAGGAAAATGGAATTTGGTCCACTGAAATT

CTGAAAAATTTCAAAAACAAGACTTTCCTGAAGTGTGAAGCACCAAATTACTCTG

GAAGGTTCACCTGCTCATGGCTGGTGCAAAGAAACATGGACTTGAAGTTCAACA

TCAAGAGCAGTAGCAGTTCCCCTGACTCTAGGGCAGTGACATGTGGAATGGCCT

CTCTGTCTGCAGAGAAGGTCACACTGGACCAAAGGGACTATGAGAAGTATTCAG

TGTCCTGCCAGGAGGATGTCACCTGCCCAACTGCTGAGGAGACCCTGCCCATTGA

ACTGGCCTTGGAAGCAAGGCAGCAGAATAAATATGAGAACTACAGCACCAGCTT

CTTCATCAGGGACATCATCAAACCAGACCCTCCCAAGAACTTGCAGATGAAGCC

TTTGAAGAACTCACAGGTGGAGGTCAGCTGGGAGTACCCTGACTCCTGGAGCAC

TCCCCATTCCTACTTCTCCCTCAAGTTCTTTGTTAGAATCCAGAGGAAGAAAGAA

AAGATGAAGGAGACAGAGGAGGGGTGTAACCAGAAAGGTGCCTTCCTGGTGGA

GAAGACATCTACAGAAGTCCAATGCAAAGGAGGGAATGTCTGTGTGCAAGCTCA

GGATAGGTATTACAATTCCTCATGCAGCAAGTGGGCATGTGTTCCCTGCAGGGTC

AGATCTGGTGGAGGTGGAAGTGGAGGTGGTGGATCTGGGGGTGGAGGCAGCAG

GGTCATTCCAGTCTCTGGACCTGCCAGGTGTCTTAGCCAGTCCAGAAACCTGCTG

AAGACCACAGATGACATGGTGAAGACTGCCAGAGAAAAACTGAAACATTATTCC

TGCACTGCTGAAGACATTGATCATGAAGACATCACAAGGGACCAAACCAGCACA

TTGAAGACCTGTCTGCCACTGGAACTGCACAAGAATGAGAGTTGCCTGGCTACTA

GAGAGACTTCTTCCACAACAAGAGGGAGCTGCCTGCCCCCACAGAAGACCTCTT

TGATGATGACCCTGTGCCTTGGTAGCATCTATGAGGACTTGAAGATGTACCAGAC

AGAGTTCCAGGCCATCAATGCAGCACTTCAGAATCACAACCATCAGCAGATCAT

TCTGGACAAGGGCATGCTGGTGGCCATTGATGAGCTGATGCAGTCTCTGAATCAT

AATGGAGAGACTCTGAGACAGAAACCTCCTGTGGGAGAAGCAGACCCTTACAGA

GTGAAAATGAAGCTCTGCATCCTGCTTCATGCCTTCAGCACCAGAGTGGTGACCA

TCAACAGGGTGATGGGCTATCTGAGCTCTGCCAGAAGGAAGAGGGGATCCTCTG

-continued

```
GAAGTGGAGCTACTAACTTCAGCCTGCTGAAGCAGGCTGGAGATGTGGAGGAGA

ACCCTGGACCTATGGAGCTGGCAGCTCTTTGTAGGTGGGGGCTTCTGCTTGCACT

GCTTCCTCCAGGAGCAGCTTCAGCTTGTCATCAACTGTGTGCTAGGGGGCATTGT

TGGGGACCAGGACCAACTCAGTGTGTGAATTGTTCACAGTTTCTGAGGGGGCAG

GAGTGTGTGGAGGAGTGTAGGGTGCTGCAAGGACTGCCCAGGGAATATGTTAAT

GCTAGGCATTGTCTGCCATGTCATCCAGAATGTCAGCCACAGAATGGTTCTGTGA

CATGTTTTGGACCTGAAGCTGATCAGTGTGTGGCATGTGCACATTATAAGGACCC

ACCTTTTTGTGTGGCAAGGTGTCCTAGTGGAGTGAAACCTGATCTGTCTTATATG

CCAATTTGGAAGTTTCCAGATGAGGAAGGGGCTTGTCAGCCTTGTCCTATCAATT

GTACACATAGTTGTGTGGATCTGGATGATAAGGGGTGTCCAGCAGAGCAAAGGG

CTTCTCCACTGACAGCTGTGGGCCAGGACACCCAGGAGGTCATTGTGGTGCCACA

CTCCTTGCCCTTTAAGGTGGTGGTGATCTCAGCCATCCTGGCCCTGGTGGTGCTC

ACCATCATCTCCCTTATCATCCTCATCATGCTTTGGCAGAAGAAGCCAAGATGAA

CCTGAGCTAGC
```

We claim:

1. A nucleic acid construct for the treatment of cancer comprising an expression cassette, wherein the expression cassette comprises a cancer-specific promoter and nucleic acid sequences encoding one or more tumor antigens, wherein the nucleic acid sequences encoding the one or more tumor antigens are engineered to have a reduced CpG content compared to their wild-type counterparts, the nucleic acid construct comprises a CpG-free plasmid backbone, or a combination thereof.

2. The nucleic acid construct of claim 1, wherein the cancer-specific promoter is the PEG-3 promoter or a functional derivative thereof.

3. The nucleic acid construct of claim 1, wherein the one or more tumor antigens is selected from the group consisting of WT1, MUC1, LMP2, HPV E6 E7, EGFRvIII, HER-2/neu, MAGE A3, p53, NY-ESO-1, PSMA, CEA, MelanA/MART1, Ras mutant, gp100, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, MYCN, RhoC, TRP-2, Mesothelin, PSCA, MAGE A1, CYP1B1, PLAC1, BORIS, ErbB2, Fibroblast activation protein alpha, FR-α, GPC3, IL13-Rα2, Mesothelin, MUC16, PSMA, ROR1, VEGFR2, αvβ6 integrin.

4. The nucleic acid construct of claim 1, wherein if multiple tumor antigens are encoded, tumor antigen sequences are separated by a picornavirus 2A ribosome skipping sequence, optionally wherein the picornavirus ribosome skipping sequence is P2A or T2A.

5. The nucleic acid construct of claim 1, wherein the nucleic acid sequences encoding one or more tumor antigens are engineered to have a reduced CpG content compared to their wild-type counterparts and a CpG-free plasmid backbone.

6. A composition for the treatment of cancer comprising the nucleic acid construct of claim 1.

7. The nucleic acid construct of claim 1, wherein the expression cassette further comprises one or more therapeutic genes.

8. The nucleic acid construct of claim 7, wherein the one or more therapeutic genes is a cytokine, a thymidine kinase optionally wherein the thymidine kinase is HSV1-TK or SR39, a toxin, a pathogen-associated molecular pattern (PAMP) optionally wherein the PAMP is flagellin (FliC), a danger-associated molecular pattern (DAMP), an immune checkpoint inhibitor gene, or any combination thereof.

9. The nucleic acid construct of claim 7, wherein if multiple therapeutic genes are present, the multiple therapeutic genes are separated by a picornavirus 2A ribosome skipping sequence, optionally wherein the picornavirus ribosome skipping sequence is P2A or T2A.

10. The nucleic acid construct of claim 7, wherein the one or more therapeutic genes is engineered to have a reduced CpG content compared to its wild-type counterpart.

11. The nucleic acid construct of claim 8, wherein the immune checkpoint inhibitor gene encodes a monoclonal antibody selected from the group consisting of an anti-PD-1 antibody, an anti-PD-L1 antibody, and an anti-CTLA-4 antibody, optionally wherein the immune checkpoint inhibitor gene encodes an immune checkpoint inhibitor fusion protein comprising a PD-1 fusion protein, optionally wherein the PD-1 fusion protein comprises a fusion of PD-1 and an immunoglobulin Fc region.

12. The nucleic acid construct of claim 8, wherein the cytokine is selected from the group consisting of IL-12, IL-24, IL-2, IL-15, and GM-CSF.

13. The nucleic acid construct of claim 8, wherein the cytokine is a single chain variant of IL-12 (scIL-12), optionally comprising the amino acid sequence encoded by SEQ ID NO:5.

14. The composition of claim 6, wherein the nucleic acid construct is formulated into nanoparticles with a cationic polymer, optionally wherein the cationic polymer is linear polyethylenimine.

15. The composition of claim 14, wherein the nanoparticles are prepared at a N/P ratio of 4 or 6.

16. The composition of claim 14, wherein the nanoparticles are lyophilized.

17. A method for treating cancer in a subject in need thereof, comprising administering to the subject the nucleic acid construct of claim 1.

18. The method of claim 17, wherein the cancer is selected from the group consisting of breast cancer, melanoma, carcinoma of unknown primary (CUP), neuroblastoma, malignant glioma, cervical cancer, colon cancer, hepatocarcinoma, ovarian cancer, lung cancer, pancreatic cancer, and prostate cancer.

19. The method of claim 17, wherein the nucleic acid construct is delivered systemically.

20. The method of claim 17 wherein the nucleic acid construct is administered in conjunction with one or more additional therapeutic agents, optionally wherein the additional therapeutic agent(s) comprise a therapeutic monoclonal antibody or a one more CAR T cells.

* * * * *